(12) United States Patent
Sessa et al.

(10) Patent No.: US 8,084,228 B2
(45) Date of Patent: Dec. 27, 2011

(54) NOGO-B RECEPTOR ANTAGONISTS

(75) Inventors: William C. Sessa, Madison, CT (US); Quing Miao, New Berlin, WI (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 12/087,435

(22) PCT Filed: Jan. 12, 2007

(86) PCT No.: PCT/US2007/000863
§ 371 (c)(1), (2), (4) Date: Apr. 9, 2009

(87) PCT Pub. No.: WO2007/084388
PCT Pub. Date: Jul. 26, 2007

(65) Prior Publication Data
US 2009/0305971 A1    Dec. 10, 2009

Related U.S. Application Data

(60) Provisional application No. 60/759,226, filed on Jan. 12, 2006.

(51) Int. Cl.
*C07K 14/435* (2006.01)
*C07H 21/04* (2006.01)
*C12N 5/00* (2006.01)
*C12N 7/01* (2006.01)
*C12N 15/09* (2006.01)
*C12P 21/02* (2006.01)

(52) U.S. Cl. ............. 435/69.1; 435/70.1; 435/235.1; 435/320.1; 435/325; 530/300; 530/350; 536/23.5

(58) Field of Classification Search ............... None
See application file for complete search history.

(56) References Cited

U.S. PATENT DOCUMENTS 5,284,933 A * 2/1994 Dobeli et al. ............. 530/350
7,390,882 B2 * 6/2008 Cairns et al. ............. 530/350
7,585,953 B2 * 9/2009 Chen et al. ............. 530/387.9

FOREIGN PATENT DOCUMENTS

WO  WO-2003000113 A3 * 1/2003
WO  WO-2004096846 A2 * 11/2004
WO  WO-2005000099 A2 * 1/2005

OTHER PUBLICATIONS

Miao et al. Identification of a receptor necessary for Nogo-B stimulated chemotaxis and morphogenesis of endothelial cells. Proc Acad Sci USA 103(29): 10997-11002, 2006.*
Acevedo et al. A new role for Nogo as a regulator of vascular remodeling. Nature Med 10(4): 382-388, 2008.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*

* cited by examiner

*Primary Examiner* — Bridget E Bunner
(74) *Attorney, Agent, or Firm* — Riverside Law LLP

(57) ABSTRACT

Nogo-B receptors bind to Nogo-B and mediate its biological function. We have discovered that Nogo-B receptor is a component of endothelial cells, and is highly expressed in intact blood vessels. The present invention provides compositions comprising the Nogo-B receptor and fragments and fusion proteins thereof. The present invention also relates to nucleic acids encoding the Nogo-B receptor and fragments and fusion proteins thereof, as well as vectors and cells comprising such nucleic acids. The present invention also relates to antibodies specific for the Nogo-B receptor and fragments and fusion proteins thereof. The present invention also provides methods for preventing, detecting and treating Nogo-B receptor-related diseases, disorders and conditions.

12 Claims, 50 Drawing Sheets

MTGLYELVWRVLHALLCLHRTLT
SWLRVRFGTWNWIWRRCCRAAS
AAVLAPLGFTLRKPPAVGRNRRH
HRHPRGGSCLAAAHHRMRWRAD
GRSLEKLPVHMGLVITEVEQEPS
FSDIASLVVWCMAVGISYISVYD
HQGIFKRNNSRLMDEILKQQQEL
LGLDCSKYSPEFANSNDKDDQVL
NCHLAVKVLSPEDGKADIVRAAQ
DFCQLVAQKQKRPTDLDVDTLAS
LLSSNGCPDPDLVLKFGPVDSTL
GFLPWHIRLTEIVSLPSHLNISYE
DFFSALRQYAACEQRLGK

SEQUENCE LISTING

<160> NUMBER OF SEQ ID NOS: 18

<210> SEQ ID NO 1
<211> LENGTH: 293
<212> TYPE: PRT
<213> ORGANISM: Homo sapiens

<400> SEQUENCE: 1

```
Met Thr Gly Leu Tyr Glu Leu Val Trp Arg Val Leu His Ala Leu Leu
 1               5                  10                  15

Cys Leu His Arg Thr Leu Thr Ser Trp Leu Arg Val Arg Phe Gly Thr
             20                  25                  30

Trp Asn Trp Ile Trp Arg Arg Cys Cys Arg Ala Ala Ser Ala Ala Val
         35                  40                  45

Leu Ala Pro Leu Gly Phe Thr Leu Arg Lys Pro Pro Ala Val Gly Arg
     50                  55                  60

Asn Arg Arg His His Arg His Pro Arg Gly Gly Ser Cys Leu Ala Ala
 65                  70                  75                  80

Ala His His Arg Met Arg Trp Arg Ala Asp Gly Arg Ser Leu Glu Lys
                 85                  90                  95

Leu Pro Val His Met Gly Leu Val Ile Thr Glu Val Glu Gln Glu Pro
            100                 105                 110

Ser Phe Ser Asp Ile Ala Ser Leu Val Val Trp Cys Met Ala Val Gly
        115                 120                 125

Ile Ser Tyr Ile Ser Val Tyr Asp His Gln Gly Ile Phe Lys Arg Asn
    130                 135                 140

Asn Ser Arg Leu Met Asp Glu Ile Leu Lys Gln Gln Gln Glu Leu Leu
145                 150                 155                 160

Gly Leu Asp Cys Ser Lys Tyr Ser Pro Glu Phe Ala Asn Ser Asn Asp
                165                 170                 175

Lys Asp Asp Gln Val Leu Asn Cys His Leu Ala Val Lys Val Leu Ser
            180                 185                 190

Pro Glu Asp Gly Lys Ala Asp Ile Val Arg Ala Ala Gln Asp Phe Cys
        195                 200                 205

Gln Leu Val Ala Gln Lys Gln Lys Arg Pro Thr Asp Leu Asp Val Asp
    210                 215                 220

Thr Leu Ala Ser Leu Leu Ser Ser Asn Gly Cys Pro Asp Pro Asp Leu
225                 230                 235                 240

Val Leu Lys Phe Gly Pro Val Asp Ser Thr Leu Gly Phe Leu Pro Trp
                245                 250                 255

His Ile Arg Leu Thr Glu Ile Val Ser Leu Pro Ser His Leu Asn Ile
            260                 265                 270

Ser Tyr Glu Asp Phe Phe Ser Ala Leu Arg Gln Tyr Ala Ala Cys Glu
        275                 280                 285

Gln Arg Leu Gly Lys
    290
```

<210> SEQ ID NO 2
<211> LENGTH: 19
<212> TYPE: RNA
<213> ORGANISM: Artificial Sequence
<220> FEATURE:
<223> OTHER INFORMATION: short interfering RNA targeting Nogo-B receptor mRNA

<400> SEQUENCE: 2

```
ccagaauuug caaauagua                                          19

<210> SEQ ID NO 3
<211> LENGTH: 19
<212> TYPE: RNA
<213> ORGANISM: Artificial Sequence
<220> FEATURE:
<223> OTHER INFORMATION: short interfering RNA targeting Nogo-B receptor
      mRNA

<400> SEQUENCE: 3
uacuauuugc aaauucugg                                          19

<210> SEQ ID NO 4
<211> LENGTH: 19
<212> TYPE: RNA
<213> ORGANISM: Artificial Sequence
<220> FEATURE:
<223> OTHER INFORMATION: short interfering RNA targeting Nogo-B receptor
      mRNA

<400> SEQUENCE: 4
ggaaauacau agaccuaca                                          19

<210> SEQ ID NO 5
<211> LENGTH: 19
<212> TYPE: RNA
<213> ORGANISM: Artificial Sequence
<220> FEATURE:
<223> OTHER INFORMATION: short interfering RNA targeting Nogo-B receptor
      mRNA

<400> SEQUENCE: 5
uguaggucua uguauuucc                                          19

<210> SEQ ID NO 6
<211> LENGTH: 12
<212> TYPE: PRT
<213> ORGANISM: Artificial Sequence
<220> FEATURE:
<223> OTHER INFORMATION: peptide fragment used to generate antibody to
      NgBR

<400> SEQUENCE: 6

Cys Arg Asn Arg Arg His His Arg His Pro Arg Gly
  1               5                  10

<210> SEQ ID NO 7
<211> LENGTH: 19
<212> TYPE: RNA
<213> ORGANISM: Artificial Sequence
<220> FEATURE:
<223> OTHER INFORMATION: nonsilencing siRNA

<400> SEQUENCE: 7
uucuccgaac gugucacgu                                          19

<210> SEQ ID NO 8
<211> LENGTH: 19
<212> TYPE: RNA
<213> ORGANISM: Artificial Sequence
<220> FEATURE:
<223> OTHER INFORMATION: nonsilencing siRNA

<400> SEQUENCE: 8
acgugacacg uucggagaa                                          19
```

-continued

```
<210> SEQ ID NO 9
<211> LENGTH: 24
<212> TYPE: DNA
<213> ORGANISM: Artificial Sequence
<220> FEATURE:
<223> OTHER INFORMATION: primer for NgBR

<400> SEQUENCE: 9
tgccagttag tagcccagaa gcaa                                              24

<210> SEQ ID NO 10
<211> LENGTH: 24
<212> TYPE: DNA
<213> ORGANISM: Artificial Sequence
<220> FEATURE:
<223> OTHER INFORMATION: primer for NgBR

<400> SEQUENCE: 10
tgatgtgcca gggaagaaag ccta                                              24

<210> SEQ ID NO 11
<211> LENGTH: 20
<212> TYPE: DNA
<213> ORGANISM: Artificial Sequence
<220> FEATURE:
<223> OTHER INFORMATION: primer for NgBR

<400> SEQUENCE: 11
cggcgacgac ccattcgaac                                                   20

<210> SEQ ID NO 12
<211> LENGTH: 23
<212> TYPE: DNA
<213> ORGANISM: Artificial Sequence
<220> FEATURE:
<223> OTHER INFORMATION: primer for NgBR

<400> SEQUENCE: 12
gaatcgaacc ctgattcccc gtc                                               23

<210> SEQ ID NO 13
<211> LENGTH: 30
<212> TYPE: PRT
<213> ORGANISM: Homo sapiens

<400> SEQUENCE: 13

Ser Trp Leu Arg Val Arg Phe Gly Thr Trp Asn Trp Ile Trp Arg Arg
  1               5                  10                  15

Cys Cys Arg Ala Ala Ser Ala Ala Val Leu Ala Pro Leu Gly
             20                  25                  30

<210> SEQ ID NO 14
<211> LENGTH: 30
<212> TYPE: PRT
<213> ORGANISM: Homo sapiens

<400> SEQUENCE: 14

Leu Ala Pro Leu Gly Phe Thr Leu Arg Lys Pro Pro Ala Val Gly Arg
  1               5                  10                  15

Asn Arg Arg His His Arg His Pro Arg Gly Gly Ser Cys Leu
             20                  25                  30

<210> SEQ ID NO 15
<211> LENGTH: 30
<212> TYPE: PRT
<213> ORGANISM: Homo sapiens
```

-continued

```
<400> SEQUENCE: 15

Gly Gly Ser Cys Leu Ala Ala His His Arg Met Arg Trp Arg Ala
1               5                   10                  15

Asp Gly Arg Ser Leu Glu Lys Leu Pro Val His Met Gly Leu
            20                  25                  30

<210> SEQ ID NO 16
<211> LENGTH: 28
<212> TYPE: PRT
<213> ORGANISM: Homo sapiens

<400> SEQUENCE: 16

Ala Asp Gly Arg Ser Leu Glu Lys Leu Pro Val His Met Gly Leu Val
1               5                   10                  15

Ile Thr Glu Val Glu Gln Glu Pro Ser Phe Ser Asp
            20                  25

<210> SEQ ID NO 17
<211> LENGTH: 30
<212> TYPE: PRT
<213> ORGANISM: Artificial Sequence
<220> FEATURE:
<223> OTHER INFORMATION: scrambled version of SEQ ID NO: 14

<400> SEQUENCE: 17

Pro Gly Arg His Leu Lys Pro Ser Arg Phe Asn Ala Arg Leu His Gly
1               5                   10                  15

Pro Cys Arg Val Leu Arg Ala His Gly Pro Leu Thr Arg Gly
            20                  25                  30

<210> SEQ ID NO 18
<211> LENGTH: 20
<212> TYPE: PRT
<213> ORGANISM: Homo sapiens

<400> SEQUENCE: 18

Thr Leu Arg Lys Pro Pro Ala Val Gly Arg Asn Arg Arg His His Arg
1               5                   10                  15

His Pro Arg Gly
            20
```

NOGO-B RECEPTOR ANTAGONISTS

RELATED APPLICATION

This application is a national stage filing under 35 U.S.C. 371 of International Application PCT/US2007/000863, filed Jan. 12, 2007, which claims the priority benefit of U.S. Provisional Application Ser. No. 60/759,226, filed Jan. 12, 2006, the contents of which are incorporated by reference in their entirety. International Application PCT/US2007/000863 was published under PCT Article 21(2) in English.

GOVERNMENT SUPPORT

The invention was supported, in whole or in part, by grant Nos. HL064793, HL061371, HL057665 and HL081190 from the National Institutes of Health. The Government has certain rights in the invention.

BACKGROUND

Nogo is the fourth member of the Reticulon family of proteins to be identified, and therefore is sometimes referred to as Reticulon 4 (RTN4). Nogo has three known expressed isoforms called Nogo-A, Nogo-B, and Nogo-C, which all arise from a common nogo gene either through alternative splicing (Nogo-A and Nogo-B) or alternative promoter usage (Nogo-C). See Oertle et al., J. Mol. Biol. 325:299-323 (2003) ("Oertle"). Nogo-A is the full length isoform, which contains 1192 amino acids. Nogo-B is a shorter splice variant. There are two forms of Nogo-B. Nogo-B1 is 373 amino acids in length, and is missing residues 186-1004 of Nogo-A. Nogo-B2 is a minor splice variant that contains an extra 19 amino acids within the amino terminus; however, its protein expression remains undetected (see Oertle). Nogo-C is the shortest isoform, 199 amino acids long, with the first 11 residues being specific to this isoform. All three isoforms contain a conserved reticulon homology domain (RHD). A 66 amino acid residue loop termed Nogo-66 in the RHD can interact with a glycosylphosphatidylinositol-linked cell-surface Nogo-66 receptor, which is believed to partially mediate the inhibitory function of Nogo-A on neuronal outgrowth.

Nogo-A and Nogo-C are highly expressed in the central nervous system (CNS), with Nogo-C additionally found in skeletal muscle, while Nogo-B is found in most tissues.

In contrast to the inhibitory action of Nogo-A on cell adhesion and axonal sprouting, the amino terminus of Nogo-B promotes the adhesion, spreading and migration of endothelial cells. Nogo-B is highly expressed in intact blood vessels and plays a role in vascular homeostasis and vascular remodeling. Vascular injury in Nogo-A/B-deficient (knockout) mice promotes exaggerated neointimal proliferation, and adenoviral-mediated gene transfer of Nogo-B rescues the abnormal vascular expansion in those knockout mice. Thus, Nogo-B is a regulator of vascular homeostasis and remodeling.

However, it is not known how Nogo-B exerts its function. Unlike Nogo-66 found in all Nogo isoforms that can interact with a neural-specific Nogo-66 receptor, the receptor for the amino terminus of Nogo-B that mediates vascular function is unknown. Identification of a receptor for the vascular functions of Nogo-B would be therefore be useful in identifying a therapeutic target.

SUMMARY OF THE INVENTION

A receptor for Nogo-B has now been discovered, along with several methods of mediating the function or the expression of the receptor. For example, compositions (e.g., fusion proteins) including a fragment of a Nogo-B receptor that inhibit tumor cell growth have been discovered.

In one embodiment, the Invention includes a composition comprising Nogo-B receptor or a fragment of the Nogo-B receptor that retains a biological activity of Nogo-B receptor. The composition may comprise full-length Nogo-B receptor.

The composition may comprise Nogo-B receptor or a fragment thereof from any animal, particularly from a mammal. In a preferred embodiment, the composition comprises human Nogo-B receptor.

In other embodiments, the invention includes a composition comprising a Nogo-B receptor fragment, where the composition inhibits Nogo-B receptor biological activity. In some embodiments, the Nogo-B receptor binds Nogo-B.

In certain embodiments, the composition comprises Nogo-B receptor or a fragment thereof and at least one pharmaceutically acceptable carrier.

In certain embodiments, the composition comprises Nogo-B receptor or a fragment thereof and at least one other component, including, but not limited to, an excipient, a therapeutic agent, a diagnostic agent, a Nogo-B agonist, a Nogo-B antagonist, a Nogo-B receptor agonist and a Nogo-B receptor antagonist.

In certain embodiments, the Nogo-B receptor or fragment of Nogo-B according to this invention is detectably labelled.

In another embodiment, the invention includes a composition comprising a Nogo-B receptor agonist or antagonist.

In yet another embodiment the Invention provides fusion proteins comprising Nogo-B or a fragment thereof and a heterologous protein component.

In other embodiments, this invention provides nucleic acid molecules that encode Nogo-B receptor, fragments of Nogo-B receptor or Nogo-B receptor fusion proteins (including fused fragments of the receptor) and vectors including such nucleic acid molecules. In certain embodiments, the nucleic acid molecules according to this invention are operably linked to an expression control sequence that facilitates expression of the Nogo-B receptor, receptor fragment or fusion protein.

In certain embodiments, the nucleic acid molecule encoding Nogo-B receptor, fragments of Nogo-B receptor or Nogo-B receptor fusion proteins are linked to an expression vector.

In some embodiments, the expression vector is a viral expression vector.

In another embodiment, this invention provides host cells comprising nucleic acids encoding Nogo-B receptor or a fragment or fusion protein thereof. In other embodiments, this invention provides host cells comprising a vector according to this invention.

The present invention also provides antibodies or antigen-binding antibody fragments specific for Nogo-B receptor. The antibodies may be polyclonal or monoclonal. The antibodies may be human, humanized or chimeric. In addition, the antibodies may act as agonists or antagonists of Nogo-B receptor activity. The invention further includes immunogenic fragments of Nogo-B receptor for generating antibodies, particularly fragments of the ectodomain.

The present invention also provides methods for producing Nogo-B receptor or fragments or fusion proteins thereof, compositions comprising Nogo-B receptor or fragments or fusion proteins thereof, and antibodies specific for Nogo-B receptor or fragments or fusion proteins thereof.

The present invention also provides methods for the detection of Nogo-B receptor expression and of identifying subjects in need of Nogo-B receptor-related treatment.

The present invention also provides methods for promoting or inhibiting angiogenesis in subjects in need thereof. The invention additionally provides methods for treating or preventing a condition characterized by undesired angiogenesis.

The present invention also provides methods of diagnosing, preventing or treating Nogo-B receptor-related diseases, conditions or disorders, of promoting Nogo-B receptor-facilitated quiescence or homeostasis, of reducing, preventing, inhibiting or treating neointima formation in subjects in need thereof, of reducing, preventing, inhibiting or treating Nogo-B receptor-mediated vascular injury in subjects in need thereof, of reducing, preventing, inhibiting or treating Nogo-B receptor-mediated vascular injury-induced ischemia, vascular narrowing or occlusion in subjects in need thereof and for promoting or inhibiting endothelial cell spreading, adhesion or migration in subjects in need thereof and/or for promoting or inhibiting vascular smooth muscle cell migration in subjects in need thereof.

In addition, the invention provides methods of detecting angiogenesis (e.g., by determining whether there is express and/or activation of NgBR) and methods of screening for compound that inhibit Nogo-B binding to NgBR and/or attenuation of NgBR-mediated biological activities (e.g., migration of endothelial cells or cell engineered to express Nogo-B).

BRIEF DESCRIPTION OF THE DRAWINGS

FIG. 33 also shows the sequence of 1-116 of NgBR (SEQ ID NO: 1).

DETAILED DESCRIPTION OF THE INVENTION

Nogo-B is a component of CEM/LR domains in cultured endothelial cells. In contrast to the inhibitory action of Nogo-A on cell adhesion and axonal sprouting, the amino terminus of Nogo-B promotes the adhesion, spreading and migration of endothelial cells. As discussed in WO 2004/096846, the contents of which are incorporated herein by reference, Nogo-B is highly expressed in intact blood vessels and plays a role in vascular homeostasis and vascular remodeling. Vascular injury in Nogo-A/B-deficient (knockout) mice promotes exaggerated neointimal proliferation, and adenoviral-mediated gene transfer of Nogo-B rescues the abnormal vascular expansion in those knockout mice. Thus, Nogo-B is a regulator of vascular homeostasis and remodeling.

The term Nogo-B refers to a 373 amino acid isoform of Nogo. Nogo-B polypeptides include those encoded by nucleic acids having GenBank accession numbers: (1) human Nogo-B: GenBank accession number AY102277 (Oertle et al., J. Mol. Biol. 325(2):299-323 (2003); mouse Nogo-B: AY102281 (Oertle et al., J. Mol. Biol. 325(2):299-323 (2003); Human Nogo-B2 AY102278 (Oertle et al., J. Mol. Biol. 325(2):299-323 (2003); and Mouse Nogo-B2: AY102284 (Oertle et al., J. Mol. Biol. 325(2):299-323 (2003) as well as species homologs of these polypeptides. Nogo-B polypeptides include those having the amino acid sequence set forth in GenBank accession numbers: (1) human Nogo-B: AAM64246 (Oertle et al., J. Mol. Biol. 325(2):299-323 (2003); and mouse Nogo-B: AAM77069 (Jin, et al., Unpublished (2002)) and species homologs of said polypeptides. The above-mentioned GenBank sequence submissions and the Oertle et al. reference are hereby incorporated by reference in their entirety.

In some embodiments, the term Nogo-B receptor (NgBR) refers to a polypeptide that binds to a purified alkaline phosphatase (AP) fusion protein with residues 1-200 at the amino terminus of Nogo-B (Am-Nogo-B, taken collectively as AP-Am-Nogo-B), but does not bind to AP or a AP-Nogo-66 (where Nogo-66 is a 66 amino acid residue loop in the RHD, as described above) fusion protein. Typically, NgBR is highly expressed in heart, liver, kidney and/or pancreas. As described herein, an isolated cDNA encoding NgBR is 2,636 base pairs encoding an open reading frame of 293 amino acids. The deduced amino acid sequence in this example includes, from amino to carboxy terminus, a signal peptide sequence of 23 amino acid residues, an ectodomain of 93 amino acid residues, a Type 1A transmembrane domain of 19 amino acid residues and a cytoplasmic domain of 158 amino acid residues. The topography of the receptor was confirmed to be in accord with the predicted topography by fluorescence-activated cell sorting analysis, where the N-terminal domain was found to be on the exterior of a cell.

Figures 1, 2:
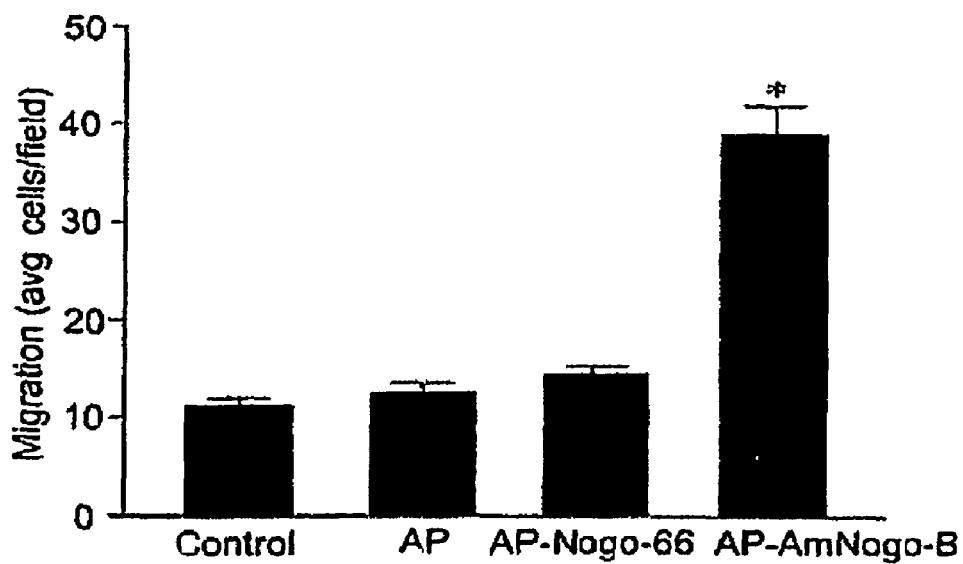
FIG. 1 shows the sequence of a human Nogo-B receptor (NgBR); SEQ ID NO:1.
FIG. 2 shows a comparison of fusion proteins on HUVEC migration.

The amino acid sequence of a Nogo-B receptor is provided in FIG. 1 as SEQ ID NO:1. In addition, the present invention includes proteins or peptides comprising an amino acid sequence having at least 80%, at least 85%, at least 90%, at least 95%, at least 97%, at least 98 or at least 99% identity to SEQ ID NO:1 or a functional fragment thereof. In some embodiments, a functional fragment comprises amino acid residues 14-293, 14-116 or 52-116 of SEQ ID NO:1.

The exemplary cDNA and translation product represented by SEQ ID NO:1 have 100% identity to a full-length sequence listed as BC013026.2 or NM138459.2 found on human chromosome 6q 22.31, with orthologs in mice, chicken and zebrafish. While this sequence has a 49% degree of similarity to the cis-prenyltransferase family of lipid-modifying enzymes (e.g., human cis-isoprenyltransferase, bacterial undecaprenyl phosphate synthase), this particular NgBR had no lipid transferase activity in a direct assay. While Applicants do not wish to be bound by theory, it is believed that NgBR may serve as a scaffold for the binding of isoprenyl ligands and/or prenylated proteins. Accordingly, it is believed the NgBR may signal via the recruitment or sequestration of prenylated proteins, such as Ras, similar to prenylated Ras binding to galectin-1 or cGMP phosphodiesterase 6 and prenylated Cdc42 or Rac2 interacting with RhoGDI.

All blood vessels contain a similar organization consisting of three layers: the tunica intima, media, and adventitia.

The tunica intima ("intima") is the innermost layer of the vessel. The intima contains primarily endothelial cells. Endothelial cells are the main regulators of vascular homeostasis because they form an interface between blood and tissue, interacting with both circulating cells and cells of the vascular wall. As an interface, they are susceptible to changes in blood composition and blood flow; therefore, endothelial cells are the main responders to these changes and play a critical role in the mechanisms underlying the development of vascular disorders.

The medial layer is called the tunica media ("media"). The media contains primarily vascular smooth muscle cells. Vascular smooth muscle cells are the effector cells of the vessel, contracting or relaxing to alter the diameter of a blood vessel in response to various agents.

The outermost layer of a blood vessel is the tunica adventitia ("adventitia").

These three layers are continuously working together to respond acutely to any changes in blood flow as well as adaptive responses to sustained alterations in flow through vessel remodeling.

Blood vessels undergo alterations due to various phenomenon, e.g., injury or disease. These alterations are accomplished by either outward or inward remodeling of the vessel. Outward remodeling increases the vessel diameter, while inward remodeling decreases lumen diameter. Remodeling also occurs under pathological conditions such as hypertension and in response to injury as in atherosclerosis (an inflammatory process by which the intima becomes thickened with lipid rich gruel and connective tissue), restenosis (a re-narrowing of the vessel lumen), and luminal stenosis after transplant vasculopathy. Nogo-B is an Important regulator of inward remodeling of blood vessels.

In certain embodiments, the invention includes a composition comprising Nogo-B receptor or a Nogo-B receptor fragment that retains Nogo-B receptor biological activity that includes, but is not limited to: (1) promoting, in a vascular endothelial cell, cellular adhesion, cellular spreading, cellular migration and/or proliferation; (2) inhibiting in a vascular smooth muscle cell migration; (3) reducing pathological vascular remodeling; (4) reducing neointima formation in a blood vessel; (5) promoting angiogenesis; (6) maintaining vascular homeostasis; and (7) promoting wound healing.

In certain embodiments, the invention includes a composition comprising a Nogo-B receptor fragment that inhibits one or more Nogo-B receptor biological activities.

In certain embodiments, the fragment in a composition inhibiting NgBR biological activity corresponds to the NgBR ectodomain, such as amino acid residues 52-116 of SEQ ID NO:1, or a sequence at least 80%, at least 85%, at least 90%, at least 95%, at least 97%, at least 98% or at least 99% identical to the NgBR ectomain or its fragment. In certain embodiments, the fragment or substantially similar sequence is taken from 10-93 consecutive amino acid residues within the NgBR ectodomain. For example, the fragment may include 10-70, such as 10-20, 15-25, 20-30, 25-35, 3040, 35-45, 40-50, 45-55, 55-60 or 60-70 amino acid residues that represent a fragment of or a sequence substantially similar to (e.g., having the identity levels described above) a fragment of the NgBR ectodomain. In preferred embodiments, the fragment or substantially similar sequence includes all or part of amino acid residues 40-85 or 45-85, such as 40-69, 41-70, 42-71, 43-72, 44-73, 45-74, 46-75, 47-76, 48-77, 49-78, 50-79, 51-80, 52-81, 53-82, 54-83, 55-84, 56-85, 57-86, 58-87, 59-88 or 60-89 of SEQ ID NO:1.

The term "identity," as known in the art, refers to a relationship between the sequences of two or more polypeptide molecules or two or more nucleic acid molecules, as determined by comparing the sequences. In the art, "identity" also means the degree of sequence relatedness between polypeptides or nucleic acid molecules, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms"). Typical methods to determine identity are designed to give the largest match between the sequences tested. Methods to determine identity are described in publicly available computer programs. Suitable computer program methods to determine identity and similarity between two sequences include, but are not limited to, the GCG program package, including GAP (Devereux et al., 1984, Nucleic Acids Res. 12:387; Genetics Computer Group, University of Wisconsin, Madison, Wis.), BLASTP, and FASTA (Altschul et al., 1990, J. Mol. Biol. 215:403-10). The BLASTX program is publicly available from the National Center for Biotechnology Information (NCBI) and other sources (Altschul et al., BLAST Manual (NCB NLM NIH, Bethesda, Md.); Altschul et al., 1990, supra). The well-known Smith Waterman algorithm may also be used to determine identity.

In certain embodiments, the composition comprises Nogo-B receptor or a fragment thereof and at least one pharmaceutically acceptable carrier.

In another embodiment, the composition comprises Nogo-B receptor or a fragment thereof and at least one other component including, but not limited to, an excipient, a therapeutic agent, a diagnostic agent, a Nogo-B agonist and a Nogo-B antagonist. Such compositions are suitable for use in the methods described herein.

Excipients according to this invention include, but are not limited to those excipients that are described in the *Handbook of Pharmaceutical Excipients*, published jointly by the American Pharmaceutical Association and the Pharmaceutical Society of Great Britain.

Therapeutic agents according to this invention include, but are not limited to anti-cancer agents, anti-inflammatory agents, anti-coagulant agents, anti-fibrotic agents, anti-hypertensives, lipid-lowering agents and immunosuppressive agents.

Anti-cancer agents have anti-cancer activity (e.g., compounds that induce apoptosis, compounds that reduce lifespan or compounds that render cells sensitive to stress) and include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These anti-cancer agents may be categorized by their mechanism of action into, for example, following groups: anti-metabolites, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenotate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disrupters.

These anti-cancer agents may be used by themselves and/or in combination with other anti-cancer agents. Many combinatorial therapies have been developed, including but not limited to those listed in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAP | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |

TABLE 1-continued

Exemplary combinatorial therapies for the treatment of cancer.

| Name | Therapeutic agents |
| --- | --- |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/ Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChIVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisone |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |

TABLE 1-continued

Exemplary combinatorial therapies for the treatment of cancer.

| Name | Therapeutic agents |
|---|---|
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VeIP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |

TABLE 1-continued

Exemplary combinatorial therapies for the treatment of cancer.

| Name | Therapeutic agents |
|---|---|
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

Combination therapies comprising a composition of the invention and a conventional anti-cancer agent may be advantageous over combination therapies known in the art because the combination allows the conventional chemotherapeutic agent to exert greater effect at lower dosage. In a preferred embodiment, the effective dose ($ED_{50}$) for an anti-cancer agent, or combination of conventional anti-cancer agents, when used in combination with a composition of the invention is at least 2 fold less than the $ED_{50}$ for the anti-cancer agent alone, and even more preferably at 5 fold, 10 fold or even 25 fold less. Conversely, the therapeutic index (TI) for such anti-cancer agent or combination of such anti-cancer agent when used in combination with a composition of the invention can be at least 2 fold greater than the TI for conventional anti-cancer regimen alone, and even more preferably at 5 fold, 10 fold or even 25 fold greater.

Exemplary anti-inflammatory agents include, for example, steroids (e.g., cortisol, cortisone, fludrocortisone, prednisone, 6-alpha-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide).

Examples of anti-coagulant agents include heparins (such as heparin sodium, heparin potassium, dalteparin sodium, dalteparin calcium, heparin calcium, parnaparin sodium, reviparin sodium, and danaparoid sodium), warfarin, enoxaparin, argatroban, batroxobin, and sodium citrate.

An anti-fibrotic agent is an agent that can reduce or inhibit the production of extracellular matrix components including but not limited to fibronectin, proteoglycan, collagen, and elastin. Examples of anti-fibrotic agents include, but are not limited to, antagonists of TGF-beta and CTGF, such as rapamycin, 5-fluorouracil, mitomycin, methotrexate and paclitaxel.

Examples of anti-hypertensive agents include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline), □-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranotol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), □-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine.

Examples of the lipid lowering agents include atorvastatin, simvastatin, pravastatin sodium, fluvastatin sodium, clinofibrate, clofibrate, simfibrate, fenofibrate, bezafibrate, colestimide, and colestyramine.

Examples of immunosuppressant agents include azathioprine, mizoribine, cyclosporine, tacrolimus, gusperimus, and methotrexate.

In other embodiments, the Nogo-B receptor or fragment of Nogo-B receptor is detectably labelled. Detectable labels suitable for use herein include, but are not limited to, radiolabels, enzyme labels, toxins, magnetic agents and drug conjugates. Detectable labels according to this invention include, but are not limited to, the following substances: enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{3}H$, $^{14}C$, $^{15}N$, $^{35}S$, $^{90}Y$, $^{99}Tc$, $^{111}In$, $^{125}I$, and $^{131}I$.

In yet another embodiment, a composition according to this invention includes a Nogo-B receptor antagonist. Examples of antagonists according to this invention include, but are not limited to, antibodies, including monoclonal and polyclonal antibodies, siRNA, antisense nucleic acids, ribozymes, aptamers, small molecule antagonists, including soluble peptides, and peptide mimetics. In certain embodiments, a composition of the invention includes a Nogo-B receptor antagonist and at least one pharmaceutically acceptable carrier, such as where the Nogo-B antagonist is detectably labelled.

Antibodies to the Nogo-B receptor specifically bind to the ectodomain of the receptor or a sequence at least 80%, 85%, 90%, 95%, 97%, 98% or even 99% identical to the ectodomain, particularly residues 52-116 of SEQ ID NO:1. Such antibodies preferably recognize Nogo-B receptor even when the cytoplasmic domain of the receptor (e.g., amino acid residues 181-293) is not present.

Exemplary siRNAs of the invention reduce the expression of NgBR in cells, such as by targeting the coding region of NgBR mRNA, the 3'-untranslated region or the 5'-untranslated region. In one embodiment, the siRNA for targeting the coding region, known as "S1," has the following forward and reverse sequences:

```
                                            (SEQ ID NO: 2)
Forward: CCAGAAUUUGCAAAUAGUA
                                            (SEQ ID NO: 3)
Reverse: UACUAUUUGCAAAUUCUGG.
```

In another embodiment, an siRNA for targeting the 3' untranslated region, known as "S2," has the following forward and reverse sequences:

```
                                            (SEQ ID NO: 4)
Forward: GGAAAUACAUAGACCUACA
                                            (SEQ ID NO: 5)
Reverse: UGUAGGUCUAUGUAUUUCC.
```

An aptamer, as used herein, is a nucleic acid (e.g., a non-naturally occurring nucleic acid) having a desirable action on a target (e.g., NgBR). A desirable action includes, but is not limited to, binding of the target, catalytically changing the target, reacting with the target in a way which modifies or alters the target or the functional activity of the target, covalently attaching to the target as in a suicide inhibitor, and facilitating the reaction between the target and another molecule. In certain embodiments, the desirable action is specific binding to a target molecule, such target molecule being a three dimensional chemical structure other than a polynucleotide (e.g., NgBR) that binds to the nucleic acid ligand through a mechanism which predominantly depends on Watson-Crick base pairing or triple helix binding, wherein the nucleic acid ligand is not a nucleic acid having the known physiological function of being bound by the target molecule. For the purposes of this invention, a preferred aptamer is a nucleic acid ligand having specific binding affinity for an epitope on the ectodomain of NgBR.

In yet another embodiment, the invention provides fusion proteins comprising the NgBR, a fragment thereof (e.g., the ectodomain, such as amino acid residues 52-116 of SEQ ID NO:1) or a sequence at least 80%, at least 85%, at least 90%, at least 95%, at least 97%, at least 98% or at least 99% identical to the NgBR or its fragment and a heterologous protein component (including fragments of the heterologous component). In certain embodiments, the fragment or substantially similar sequence is taken from 10-93 consecutive amino acid residues within the NgBR ectodomain. For example, fusion proteins of the invention may include 10-70, such as 10-20, 15-25, 20-30, 25-35, 30-40, 35-45, 40-50, 45-55, 55-60 or 60-70 amino acid residues that represent a fragment of or a sequence substantially similar to (e.g., having the identity levels described above) a fragment of the NgBR ectodomain. In preferred embodiments, the fragment or substantially similar sequence includes all of part of amino acid residues 40-69, 41-70, 42-71, 43-72, 44-73, 45-74, 46-75, 47-76, 48-77, 49-78, 50-79, 51-80, 52-81, 53-82, 54-83, 55-84, 56-85, 57-86, 58-87, 59-88 or 60-89 of SEQ ID NO:1.

Examples of heterologous protein components of a fusion protein according to this invention include, but are not limited to, one or more of targeting agents (e.g., agents that target the fusion protein to vasculature, endothelial cells, or vascular smooth muscle cells), imaging agents, tags (e.g., hemagglutinin (HA), multiple histidines), glutathione-S-transferase (GST), alkaline phosphatase (AP), immunoglobulin Fc portions and cell permeable peptides.

An exemplary fusion protein includes the NgBR, fragment thereof or substantially similar sequence, along with the Fc portion of IgG, HA and multiple histidines, such as in the following arrangement:

Optional signal peptide-Fc-NgBR/fragment/similar sequence-HA-histidines.

Preferably, such proteins are recognized by an anti-NgBR antibody.

In another embodiment, this invention provides nucleic acid molecules that encode fragments of Nogo-B receptor or Nogo-B receptor fusion proteins. In some embodiments, the fragment may be used as a probe to identify and/or isolate a nucleic acid encoding Nogo-B receptor. In some embodiments, the fragment encodes a Nogo-B receptor fragment or fusion protein that retains or inhibits a biological activity of Nogo-B receptor. The nucleic acid molecule can be RNA or DNA. If the nucleic acid is DNA, the nucleic acid can be cDNA or genomic DNA.

The nucleic acid probes may comprise a label group attached thereto, e.g., a radioisotope, a fluorescent compound, an enzyme, or an enzyme co-factor. Such probes can be used as a part of a diagnostic kit for identifying cells or tissues expressing Nogo-B receptor.

Nucleic acid fragments of at least 6 nucleotides (e.g., at least 7, 8, 9 or 10) in length can be used as primers in PCR, primer extension and the like. Of course, larger fragments having at least 25, 30, 35, 40, 45, 50, 100, 150, 200, 250, 300, 350, 400, 450, 500 or more nucleotides are also useful, and at times preferred, as will be appreciated by the skilled worker.

The nucleic acid molecules according to this invention may be operably linked to an expression control sequence that facilitates expression of the Nogo-B receptor fragment or fusion protein.

In yet another embodiment, the present invention provides vectors that comprise nucleic acid molecules of the invention. The recombinant nucleic acid molecules and more particularly, the expression vectors of this invention may be used to express Nogo-B receptor protein or fragments or fusion proteins thereof.

Nucleic acid sequences may be expressed by operatively linking them to an expression control sequence in an appropriate expression vector and employing that expression vector to transform an appropriate unicellular host. Expression control sequences are sequences which control the transcription, post-transcriptional events and translation of nucleic acid sequences. Such operative linking of a nucleic sequence of this invention to an expression control sequence, of course, includes, if not already part of the nucleic acid sequence, the provision of a translation Initiation codon, ATG or GTG, in the correct reading frame upstream of the nucleic acid sequence.

A wide variety of host/expression vector combinations may be employed in expressing the nucleic acid sequences of this invention. Useful expression vectors, for example, may consist of segments of chromosomal, non-chromosomal and synthetic nucleic acid sequences. Useful expression vectors for bacterial and eukaryotic host cells, such as yeast, insect or mammalian cells, may be used and are well known in the art. Exemplary prokaryotic host cells include *E. coli* (e.g., HB101, DH5-alpha, DH10, and MC1061), *B. subtilis*, *Pseudomonas* spp., other *Bacillus* spp. and *Streptomyces* spp. Exemplary eukaryotic host cells include CHO, CHO DHFR (−), BHK, HEK 293 or 293T, 3T3, NSO, CV-1, neuroblastoma N2A, HeLa, mouse L-929, HaK, COS-1 and COS-7 cells. Expression in mammalian cells, for example, can be achieved using a variety of plasmids, including pSV2, pBC12BI, and p91023, as well as lytic virus vectors (e.g., vaccinia virus, adeno virus, and baculovirus), episomal virus vectors (e.g., bovine papillomavirus), and retroviral vectors (e.g., murine retroviruses). Useful vectors for insect cells include baculoviral vectors and pVL941.

In addition, any of a wide variety of expression control sequences may be used in these vectors to express the DNA sequences of this invention. A multitude of expression control sequences are available in the art and may be selected to direct appropriate expression of the nucleic acids and/or polypeptides of the invention. For instance, any of a wide variety of expression control sequences, sequences that control the expression of a DNA sequence when operatively linked to it, may be used in vectors to express sequences encoding the polypeptides of this invention. Expression control sequences that control transcription include promoters, enhancers and transcription termination sites. Expression control sequences in eukaryotic cells that control post-transcriptional events include splice donor and acceptor sites and sequences that modify the half-life of the transcribed RNA, e.g., sequences that direct poly(A) addition or binding sites for RNA-binding proteins. Expression control sequences that control translation include ribosome binding sites, sequences which direct targeted expression of the polypeptide to or within particular cellular compartments, and sequences in the 5' and 3' untranslated regions that modify the rate or efficiency of translation and/or mRNA degradation.

Many examples of useful expression control sequences, including constitutive, inducible and tissue-specific promoter and/or enhancer sequences, are known to control the expression of genes of prokaryotic or eukaryotic cells and their viruses. Promoters suitable for use with prokaryotic hosts include the regulated beta-lactamase, lactose, tryptophan (trp) and lambda phage promoter systems, alkaline phosphatase, and hybrid promoters such as the tac promoter. Promoters for use in bacterial systems will preferably contain a Shine-Dalgarno (S.D.) sequence operably linked to the DNA encoding the polypeptide of interest. Examples of suitable promoters for use in yeast hosts include the promoters for 3-phosphoglycerate kinase or other glycolytic enzymes. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Transcription from vectors in mammalian host cells may be controlled, for example, by promoters obtained from the genomes of viruses such as polyoma virus, fowlpox virus, adenovirus (such as Adenovirus 2 or 5), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems. Other useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage 1, the control regions for fd coat protein, the promoter for 3-phosphoglycerate kinase or other glycolytic enzymes, the promoters of acid phosphatase, e.g., Pho5, the promoters of the yeast a-mating factors, the polyhedron promoter of the baculovirus system and other sequences known to control the expression of genes of prokaryotic or eukaryotic cells or their viruses, and various combinations thereof. The nucleic acid molecule encoding fragments of Nogo-B receptor or Nogo-B receptor fusion proteins, may be linked to an expression vector. Such vectors are useful, e.g., for amplifying the polynucleotides in host cells to create useful quantities thereof. In other embodiments, the vector is an expression vector wherein the polynucleotide of the invention is operatively linked to a polynucleotide comprising an expression control sequence. Such vectors are useful for recombinant production of polypeptides of the invention. In an alternative embodiment, the expression vector may be a viral expression vector. Examples of viral expression vectors according to this invention include, but are not limited to: AAV (adeno-associated virus), lentivirus, adenovirus, retrovirus, and Herpes virus vectors.

In another embodiment, this invention provides host cells comprising nucleic acids encoding Nogo-B receptor or a fragment or fusion protein thereof. An alternative embodiment of this invention provides host cells comprising a vector according to this invention. Such host cells are useful for amplifying the nucleic acids and also for expressing Nogo-B receptor or a fragment thereof encoded by the nucleic acids.

The invention provides antibodies that bind, preferably specifically, to Nogo-B receptor. The antibodies can be specific for linear epitopes, discontinuous epitopes, or conformational epitopes of Nogo-B, either as present on the polypeptide in its native conformation or, in some cases, as present on the polypeptides as denatured, as, e.g., by solubilization in SDS.

An antibody of this invention refers to a full antibody, e.g., an antibody comprising two heavy chains and two light chains, or to an antigen-binding fragment of a full antibody. Such fragments include, but are not limited to, those produced by digestion with various proteases, those produced by chemical cleavage and/or chemical dissociation, and those produced recombinantly, so long as the fragment remains capable of specific binding to an antigen. Among these fragments are Fab, Fab', F(ab')$_2$, Fv, single chain Fv, Fd, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide.

An antibody of this invention can be a murine or hamster antibody or a homolog thereof, or a fully human antibody. An antibody of this invention can also be a humanized antibody, a chimeric antibody, an antibody fusion, an diabody, an intrabody, or a single-chain antibody. An antibody of this invention can be of any suitable isotype and subtype, for example, IgA (e.g., IgA1 and IgA2), IgG (e.g., IgG1, IgG2, IgG3 and IgG4), IgE, IgD, IgM, wherein the light chains of the immunoglobulin may be of type kappa or lambda. While the useful antibodies are generally monoclonal, polyclonal antibodies, such as those from mice, rabbits, turkeys, or sheep, may also be used.

In a preferred embodiment, all of the variable and constant domains are derived from human immunoglobulin sequences (a fully human antibody). These antibodies may be prepared in a variety of ways, as will be appreciated by the skilled worker.

A humanized antibody comprises sequences derived from a non-human species and human immunoglobulin sequences. In some embodiments, certain amino acids in the framework and/or constant domains of heavy and light chains of non-human origin have been mutated so as to avoid or abrogate an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293, the contents of which are incorporated herein by reference. In still further embodiments, the CDRs from a non-human sequence antibody are grafted into a human sequence framework.

The term "chimeric antibody" refers to an antibody that contains one or more regions from one antibody and one or more regions from one or more other antibodies.

Methods of making antibodies, including monoclonal antibodies, are well-known in the art. The antibodies of the invention may be made by any such methods including but not limited to immunizing a non-human animal with Nogo-B receptor or an immunogenic fragment thereof and recovering the antibody, in vitro immunization of B cells immortalization technology (including hybridoma technology), phage display and the like. Nucleic acid molecules encoding the heavy and light chains of antibodies of the invention may be isolated according to methods well known in the art and expressed recombinantly in a host cell under suitable conditions, using an appropriate vector (such as those described above).

As a response to vascular injury to the luminal surface of a vessel, either through mechanical injury (balloon angioplasty leading to restenosis) or endothelial dysfunction (atherosclerosis), the intima expands and thickens. This neointima becomes a complex milieu containing extracellular matrix, vascular smooth muscle that expand out from the underlying tunica media, inflammatory cells invading from the circulation, and bone marrow-derived progenitor cells recruited to the site of injury.

Neointima formation begins immediately after injury. Neointima formation involves numerous types of cells, including vascular smooth muscle cells and endothelial cells. After injury, vascular smooth muscle cells begin to proliferate and migrate into the lumen of the vessel. Smooth muscle cells are seen in the intima within 8 days of injury. By 4 weeks their migration and proliferation into the intima has peaked.

The endothelium also plays a role in response to vascular injury as neointimal thickness is correlated to the rate of re-endothelialization after injury.

Residues 1-200 of Nogo-B, which make up the amino terminus, is a functional domain of Nogo-B. This domain is referred to herein as Am-Nogo-B. Am-Nogo-B enhances endothelial cell spreading. Am-Nogo-B also dose-dependently increases endothelial and vascular smooth muscle cell adhesion. Am-Nogo-B functions as a chemoattractant for endothelial cells by dose-dependently enhancing their migration. Am-Nogo-B inhibits migration of vascular smooth muscle cells.

Cell spreading and adhesion are critical events in maintaining homeostasis, because they are important for the assembly of cells into three dimensional structures and the maintenance of these structures through either cell-cell or cell-substrate interactions. Specifically within the vasculature, adhesion and spreading are important not only for laying the foundation for new vessels, but also for vessel maturation. Therefore, Nogo-B functions in maintaining vessel structure (homeostasis) by promoting vascular cell adhesion and spreading.

Furthermore, the migration of vascular cells is one of the key mechanisms involved in arterial remodeling. Accordingly, Nogo-B also functions in vascular remodeling. Thus, Nogo-B functions to maintain vessel integrity after injury, since it inhibits smooth muscle cell chemotaxis, while also facilitating repair of the injured vessel, in its role promoting endothelial cell chemotaxis.

Thus, Nogo-B is a regulator of vascular cell spreading, adhesion, and migration. The Nogo-B receptor similar mediates the role of Nogo-B. Cells stably transfected with cDNA for the Nogo-B receptor bind Am-Nogo-B or a related fusion protein (e.g., AP-Am-Nogo-B) and have a chemotactic response to Am-Nogo-B or a functional equivalent. As demonstrated herein, treatment with siRNA targeting NgBR (e.g., siRNA targeting the coding region or the 3'-untranslated region of NgBR) reduces the expression of NgBR mRNA, NgBR protein, binding of Nogo-B, fragments thereof and fusion proteins containing Nogo-B or a fragment (e.g., AP-Am-Nogo-B) and partially or completely reduces Nogo-B-mediated chemotaxis (e.g., of endothelial cells).

Likewise, incubation of endothelial cells with one of the above-mentioned fragments of the NgBR ectodomain or fusion proteins including a fragment of the NgBR ectodomain or a sequence having sufficient homology thereto, as described above, inhibits binding of Nogo-B (or a functional equivalent) to the NgBR and inhibits migration of endothelial cells treated with Am-Nogo-B or a functional equivalent (e.g., as a competitive antagonist).

Nogo-B also has a role as a mediator of vascular remodeling. A lack of Nogo-B correlates with increased neointimal expansion. After vascular injury in normal mice, there is a dramatic loss of Nogo-B expression in the media at 10 days, which continues up to 21 days where there is little Nogo-8 detected in the media as well as neointima. Furthermore, there is a significant increase in neointima formation in injured vessels from Nogo-A/B (−/−) mice. In some vessels the neointima expansion was so severe that the vessel became occluded. The toes of Nogo-A/B (−/−) mice were black, consistent with a decrease of blood flow to the lower limb due to a narrowing of the vessel lumen. The role of Nogo-B in neointimal formation is further established by the correction of the enhanced neointimal phenotype of Nogo-A/B (−/−) mice when injured vessels are adenovirally transduced with Nogo-B.

The increased neointima formation observed in Nogo-A/B (−/−) injured arteries may be due to enhanced vascular smooth muscle cell migration and/or proliferation as well as impaired endothelial cell migration and/or proliferation. Therefore, Nogo-B functions as a negative regulator by placing a brake on the migration of vascular smooth muscle cells that comprise the growing neointima.

Although the mechanisms of Nogo-B function in vessel remodeling remain to be completely elucidated, the role of Nogo-B in neointima formation provides a new therapeutic target for vascular diseases involving luminal remodeling, such as restenosis after percutaneous transluminal angioplasty.

Nogo-B also plays a role in vessel remodeling, as its expression is regulated during neointima formation, and the loss of Nogo-A/B results in a greatly enhanced intimal expansion; moreover, reconstitution of vessels with Nogo-B abolished the enhanced neointimal phenotype seen in Nogo-A/B (−/−) mice. Therefore, removal of the Nogo-B constraint leads to enhanced neointima and in some cases occlusion of the vessel. Providing further evidence for Nogo-B in this response, adenoviral reconstitution of vessels from Nogo-A/B (−/−) mice with Nogo-B abolished the enhanced neointimal phenotype seen in these knockout mice.

Adenoviral overexpression of Nogo-B within the vessel wall in wild-type mice reduces intimal expansion after vascular injury.

Nogo-B can also act as a negative regulator by promoting the migration of endothelial cells back into the site of injury since re-endothelialization leads to a cessation of neointimal progression. Conversely, Nogo-B can halt intimal expansion by decreasing the migration of vascular smooth muscle into the lumen.

Thus, Nogo-B functions as a chemoattractant for endothelial cells by dose-dependently increasing their migration. But Nogo-B functions in the opposite way with vascular smooth muscle cells because it inhibits the migration of vascular smooth muscle cells.

Nogo-B inhibits vascular smooth muscle cell migration as it relates to cell proliferation.

Because Am-Nogo-B is a positive regulator of endothelial cell migration, Nogo-B functions in angiogenesis as well. During angiogenesis, vessels endothelial cells need to proliferate and migrate to lay the foundation for neo-vessels. As demonstrated herein, inhibition of function or expression of the NgBR (e.g., using siRNA) attenuates formation of tubes such as blood vessels.

A further embodiment of the invention relates to the role of Nogo-B receptor as a therapeutic target for vascular disease, wound healing and cancer. The role of Nogo-B and its receptor as a mediator of luminal vessel remodeling makes the Nogo-B receptor a novel therapeutic target for clinically relevant vascular diseases such as restenosis, stenosis after transplant vasculopathy, and atherosclerosis. Since Nogo-B functions as a brake, augmenting the expression of the Nogo-B receptor in cells may decelerate the luminal remodeling and neointima formation that occurs in these diseases of vessel injury. Restenosis, or a renarrowing of the lumen, occurs in 30% to 60% of patients where a successful angioplasty has been performed. Luminal stenosis in transplant vasculopathy is the most common cause of graft failure and death after heart transplantation. It is characterized by diffuse angiographic luminal narrowing that is not amenable to revascularization after transplant. See Ward et al., Circulation 102:1186-1191 (2000). Both of these conditions lead to inward or constrictive remodeling within the vessel marked by neointimal thickening. See Van Belle et al., Textbook of Cardiovascular Medicine, E. J. Topol, ed. (Philadelphia, Pa., Lippincott Williams & Williams) (2002). Atherosclerosis is an inflammatory process by which the intima becomes thickened due to lipid rich gruel, an aggregation of macrophages and T-lymphocytes, which eventually forms a fibrous plaque that protrudes into the lumen of the vessel hampering blood flow. It is the principal cause of myocardial and cerebrovascular infarction in hypertensive patients (leading causes of death in the Western world), as well as gangrene in the lower extremities of diabetic patients. See Ross, Nature 362:801-809 (1993).

Increasing Nogo-B receptor activity vis a vis endothelial cells and vascular smooth muscle cells, is useful to maintain vascular health and integrity, repair vascular injury, and promote vascular proliferation. Accordingly, in another aspect, the invention provides a method for promoting angiogenesis in a subject in need thereof. Enhanced angiogenesis is desired, for example, in connection with wound healing, in diabetes that is characterized by peripheral vascular disease (i.e., insufficient peripheral vasculature), and in coronary artery disease (to by-pass blockages in blood vessels).

According to another aspect of the invention, increasing Nogo-B receptor activity prevents or reduces undesirable vascular remodeling such as neo-intima formation in injured blood vessels. Such pathological intima formation narrows the lumen of the blood vessel and may even cause complete occlusion of the vessel. Such vascular neo-intima formation often follows procedures such as angioplasty, myocardial infarction and in tissue and organ transplantation. Injury to blood vessels leads to decreased levels of Nogo-B in the blood vessel cells. Also, contacting such blood vessels with Nogo-B promotes healing and reduced or inhibited neo-intima formation. Increasing Nogo-B receptor activity and/or expression in relevant cells are useful to treat conditions including hypertension, restinosis, transplant vasculopathy, arteriosclerosis, ischemia, hypertension, pulmonary hypertension, asthma, vascular infarctions including myocardial infarction, and other conditions characterized by Nogo-B mediated undesirable vascular remodeling.

Nogo-B receptor and Nogo-B have been found in two models of angiogenesis, intradermal injection of adenoviral VEGF into the ear and healing of full-thickness wounds, where the peptide and receptor are present in both endothelial cells and pericytes in a subset of growing and more mature angiogenic vessels. In a different model of angiogenesis, Nogo-B and Nogo-B receptor colocalize with PECAM-1-positive endothelial cells after 10 days of wound healing.

In some conditions, such as cancer, retinopathy, rheumatoid arthritis, atherosclerosis and arteriosclerosis, it is desirable to inhibit or suppress angiogenesis (e.g., to slow tumor growth). In such conditions, it would be desirable to inhibit Nogo-B mediated effects on blood vessels either by inhibiting the expression level or one or more biological activities of Nogo-B receptor. Accordingly, in a further aspect, the invention provides a Nogo-B receptor antagonist or a Nogo-B receptor mimic that competes with the Nogo-B receptor for Nogo-B (or Am-Nogo-B or a functional equivalent) binding and thereby reduces Nogo-B receptor activity, such as those described above.

Antagonists may include any Nogo-B receptor binding partner, preferably a binding partner that specifically binds Nogo-B receptor and inhibits one or more Nogo-B receptor activities. Antagonist binding partners include but are not limited to antibodies, small molecules, peptides, aptamers and the like. In certain embodiments, a binding partner has a $K_d$ for Nogo-B receptor of less than about 20 nM, less than about 10 nM, less than about 5 nM, less than about 3 nM, less than about 2 nM, less than about 1 nM, less than about 0.5 nM, less than about 0.3 nM or even less than about 0.1 nM. Exemplary binding partners include a sequence at least 80%, at least 85%, at least 90%, at least 95% or 100% identical to all or a fragment of amino acid residues 180-200 of Nogo-B and do not activate or minimally activate NgBR. Preferably, such exemplary binding partners include sufficient additional amino acid residues to permit the binding partner to have a secondary and/or tertiary structure substantially resembling that of Receptor mimics may include any Nogo-B binding partner, preferably a binding partner that specifically binds Nogo-B and inhibits one or more Nogo-B receptor activities, such as through preventing activation of Nogo-B receptor. Receptor mimics include but are not limited to antibodies, small molecules, peptides, and the like. In certain embodiments, a receptor mimic has a $K_d$ for Nogo-B of less than about 20 nM, less than about 10 nM, less than about 5 nM, less than about 3 nM, less than about 2 nM, less than about 1 nM, less than about 0.5 nM, less than about 0.3 nM or even less than about 0.1 nM. An exemplary receptor mimic is a fusion protein or antibody that includes all or a fragment of the Nogo-B receptor ectodomain (e.g., amino acid residues 52-116 of SEQ ID NO:1), or a sequence at least 80%, 85%, 90%, 95%, 97%, 98% or 99% identical to all or a fragment of the ectodomain.

Alternatively, it may be desirable to reduce expression of Nogo-B receptor at the level of transcription, translation or post-translation processing. Such inhibition of Nogo-B receptor expression may be accomplished by any means known in the art, including but not limited to siRNA (e.g., those described above), antisense nucleic acids and/or ribozymes.

In certain embodiments, methods of the invention include a combination or an adjunct therapy such as surgery, radiation, a diagnostic or therapeutic agent (e.g., an anti-cancer agent) or a combination thereof.

In certain embodiments, compositions of the invention are administered to subjects or cells. Administration is preferably in a "therapeutically effective amount", this being sufficient to show benefit to a subject or cell. Such benefit is, for example, amelioration of at least one symptom. The actual amount administered, and rate and time-course of administration, will depend on the nature and severity of the condition treated and the size and/or age of the subject or cell population. Appropriate doses of compositions of the invention can be determined by a skilled artisan.

The precise dose will depend upon a number of factors, including whether the composition is for diagnosis or for treatment, the size and location of the area to be treated, the precise nature of the therapeutic compound (e.g. nucleic acid, whole protein, fragment or fusion protein), and the nature of any detectable label or other molecule attached to the compound. A typical dose will be in the range 100 μg to 1 gm for systemic applications, and 1 μg to 1 mg for topical applications and for cells in vitro. The doses above are ranges for a typical 70 kg adult human, may be proportionally adjusted for based upon the size and species of the subject, and also adjusted for other formats in proportion to molecular weight. Treatments may be repeated at daily, twice-weekly, weekly or monthly intervals, at the discretion of the physician. In certain embodiments of the present invention, treatment is periodic, and the period between administrations is about two weeks or more, preferably about three weeks or more, more preferably about four weeks or more, or about once a month.

For purposes of the present invention, treating is defined as totally or partially ameliorating one or more symptoms of a disease or condition. Prevention is definition herein as completely or partially delaying the onset of symptoms of a disease or condition and/or completely or partially reducing the severity of symptoms of a disease or condition.

A subject is defined herein as a animal treated by a method described herein. Typically, a subject is a mammal, particularly a human. Subjects also include domestic and barnyard animals, such as horses, cows, sheep, goats, pigs, cats, dogs, rats and mice.

The composition may be administered, for example, via an oral, mucosal, buccal, intranasal, inhalable, intravenous, subcutaneous, intramuscular, parenteral, intratumor, transdermal or topical route. The composition can also be administered continuously via a minipump.

In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are generally known to those skilled in the art. See, e.g., *Sustained and Controlled Release Drug Delivery Systems* (J. R. Robinson, ed., Marcel Dekker, Inc., New York, 1978).

In certain embodiments, a composition of the invention is orally administered, for example, with an inert diluent or an assimilable edible carrier. The compound (and other ingredients, if desired) can also be enclosed in a hard or soft shell gelatin capsule, compressed into tablets, or incorporated directly into the subject's diet. For oral therapeutic administration, the active compound can be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Additional active compounds, such as those described above, also can be incorporated into the compositions. In certain embodiments, Nogo-B is co-formulated with and/or co-administered with one or more additional therapeutic agents. Co-administration includes administration in the same formulation, at the same time (but in different formulations), sequentially, or during the course of therapy (but at different times, such as offset by one or more hours or on different days). Compositions of the invention can also be used during the course of a therapeutic regimen including other treatments.

Throughout this specification and claims, the word "comprise," or variations such as "comprises" or "comprising," will be understood to imply the inclusion of a stated integer or group of integers but not the exclusion of any other integer or group of integers.

In order that this invention may be better understood, the following examples are set forth. These examples are for the purpose of illustration only and are not to be construed as limiting the scope of the invention in any manner.

EXAMPLES

Example 1

Identification and Characterization of a Nogo-B Receptor

The migratory response of human umbilical vein endothelial cells (HUVEC) in response to a gradient of recombinant, purified alkaline phosphatase (AP) fusion protein expressing Am-Nogo-B or a recombinant purified Am-Nogo-B was examined. HUVEC were cultured in M199 with 20% FBS and endothelial cell growth supplement (ECGS).

To express Am-Nogo-B, the human Nogo-B cDNA of residues 1-200 was ligated into pcSecTag2-HygroC (Invitrogen) by using the Ig κ-chain signal peptide of pSecTag2 with an in-frame Myc-His tag or pcAP-5 in frame with the signal sequence, His tag, and placental coding region. The resultant plasmid DNA was transfected into HEK293T cells (cultured in high-glucose DMEM with 10% FBS), and secreted Am-Nogo-B or AP-Am-Nogo-B was purified with Ni-affinity chromatography.

Cell migration was examined in modified Boyden chambers using 10 nM each of purified recombinant AP, AP fusion of Nogo-66 (AP-Nogo-66) or Am-Nogo-B. The transwell inserts (Costar transwell inserts; Corning) were coated with a solution of 0.1% gelatin (Sigma) in PBS at 4° C. overnight and then air-dried. VEGF at 50 ng/mL (1.1 nM) or recombinant Am-Nogo-B at various concentrations dissolved in medium 199 containing 0.1% BSA was added in the bottom chamber of the Boyden apparatus. HUVEC (200,000 cells) suspended in a 100 μL aliquot of medium 199 containing 0.1% BSA was added to the upper chamber. After 5 hours incubation, cells on both sides of the membrane were fixed and stained with a Diff-Quik staining kit (Baxter Healthcare, Miami, Fla.). The average number of cells from five randomly chosen high-power (×400) fields on the lower side of the membrane was counted.

To detect AP-Am-Nogo-B binding, cultures were washed with Hanks' balanced salt solution (HBSS) containing 20 mM HEPES, pH 7.5, and 1 mg/mL BSA (HBH). The plates were then incubated with AP-Am-Nogo-B in DMEM containing 20 mM Hepes, pH 7.5, and 1 mg/mL BSA for 2 hours at 4° C. The bound AP-Am-Nogo-B was detected by using the Blue Substrate kit (Vector Laboratories). The blue staining was examined by using the ODYSSEY Infrared Imaging System (Li-Cor, Lincoln, Nebr.) and confirmed by microscopy. Alternatively, the bound AP-Am-Nogo-B was extracted with Triton X-100, and AP activity was colorimetrically quantified by using p-nitrophenyl phosphate (Sigma) as substrate after heat inactivation of endogenous AP. Non-specific binding was determined by measuring binding in the presence of a 100-fold molar excess of recombinant Am-Nogo-B lacking the AP fusion protein. Specific binding was determined by subtracting the non-specific binding from total binding. For determination of apparent $K_d$, the binding of AP-Am-Nogo-B was measured in triplicate as described above and the $K_d$ value was quantified by using the Scatchard plot program of GraphPad PRISM (one-site binding, linear regression) using the ratio of bound ligand to free ligand as the y axis and bound ligand (pM) as the x axis.

Figure 3:
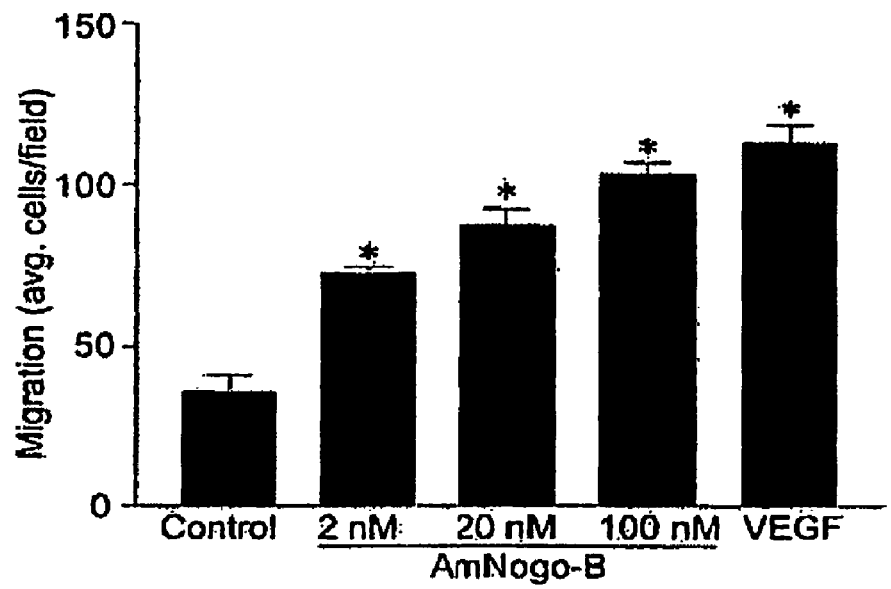
FIG. 3 shows the dose-dependent migration of HUVEC in response to purified recombinant Am-Nogo-B or VEGF.
Figure 4:
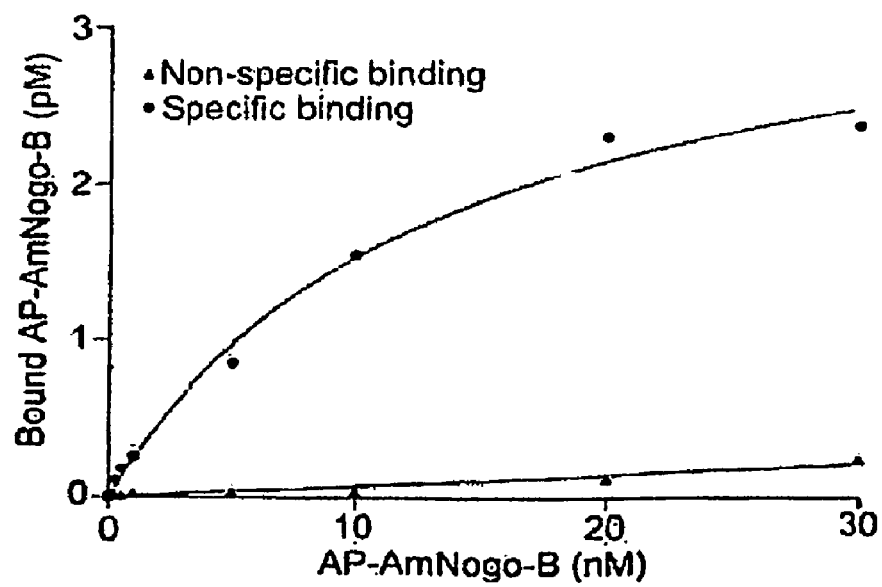
FIG. 4 shows the binding of Am-Nogo-B to the surface of native HUVEC.
Figure 5:
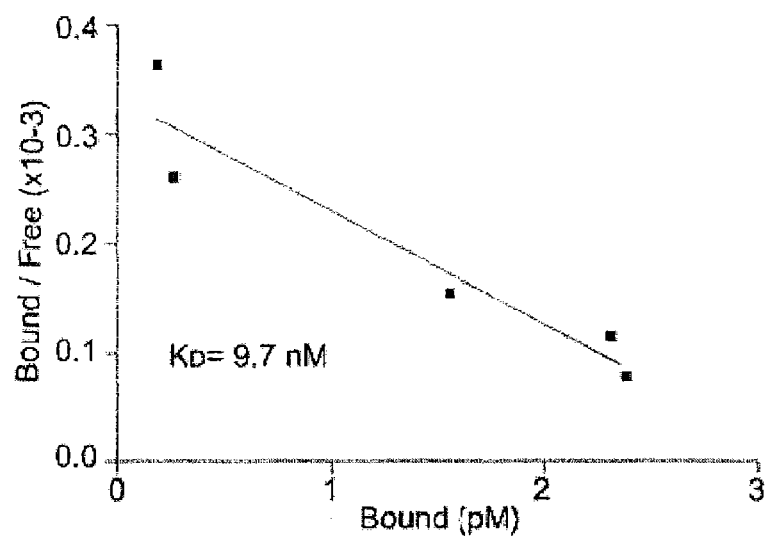
FIG. 5 shows a Scatchard plot of the data from FIG. 4.

As shown in FIGS. 2 and 3, AP alone or an AP-Nogo-66 does not promote HUVEC migration, but Am-Nogo-B dose-dependently increases migration of endothelial cells, similarly in magnitude to 1.1 nM VEGF. As shown in FIGS. 4 and 5, AP-Am-Nogo-B binds to a specific, saturable, high-affinity binding site on endothelial cells with an estimated $K_d$ of 9.7 nM. These results suggest that Am-Nogo-B interacts with a unique receptor.

A recombinant AP-Am-Nogo-B fusion protein was used to screen a cDNA expression library from human heart (500,000 independent clones) transfected into COS or CHO cells using Lipofectamine 2000 (Invitrogen). COS-7 cells were cultured in high-glucose DMEM with 10% FBS. CHO cells were cultured in MEM-α with 5% FBS.

Figure 6:
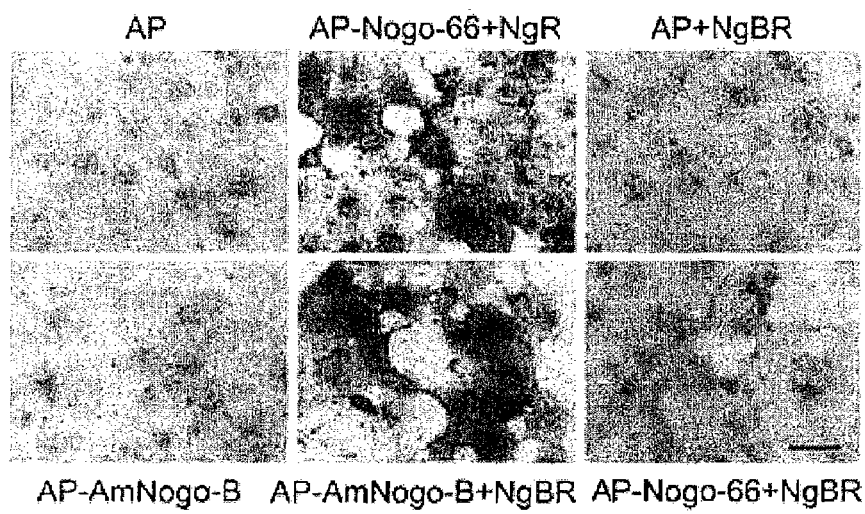
FIG. 6 shows binding of AP, AP-Am-Nogo-B and AP-Nogo-66 to COS-7 cells transfected with an expression vector encoding human NgBR or Nogo receptor.

For expression cloning of Am-Nogo-B receptor, pools of 5,000 arrayed clones from a human heart cDNA library (OriGene Technologies, Rockville, Md.) were transfected into COS-7 cells, and AP-Am-Nogo-B binding was assessed by using AP versus AP-Am-Nogo-B binding and detection of the AP product by near-infrared cell imaging (Li-Cor, Lincoln, Nebr.) or AP activity assays. As shown in FIG. 6, first column of wells, upper and lower, COS cells do not bind AP or AP-Am-Nogo-B but selectively bind AP-Nogo-66 when transfected with cDNA encoding the Nogo receptor (upper, second column).

Single NgBR cDNA clones were isolated by sib selection and sequenced. A NgBR-HA was created in pIRESneo vector (BD, Palo Alto, Calif.), with the HA tag at the carboxy terminus. To access the physical interaction of NgBR with Am-Nogo-B, 50 μg of solubilized extracts of CHO cells expressing control vector (pIRESneo) or NgBR-HA was incubated with 25 μg of purified Am-Nogo-B or buffer for 2 hours at room temperature. The HA-tagged NgBR was immunoisolated with anti-HA immunobeads (Roche, Indianapolis, Ind.) and associated proteins analyzed by Western blotting. For the Western blots, expression of NgBR-HA was detected by using anti-HA (Roche) and NgBR (Imgenex), respectively, and beta-actin (Sigma) or Hsp90 (BD Biosciences-Pharmingen) was used to control for loading.

As shown in FIG. 6, after several rounds of screening, amplification and sib selection, a single cDNA was isolated and, when transfected into COS cells, afforded the binding of Am-Nogo-B (lower, second column) but not AP (upper, third column) or AP-Nogo-66 (lower, third column). The deduced sequence of the peptide sequence from this cDNA is shown in FIG. 1.

Figure 7:
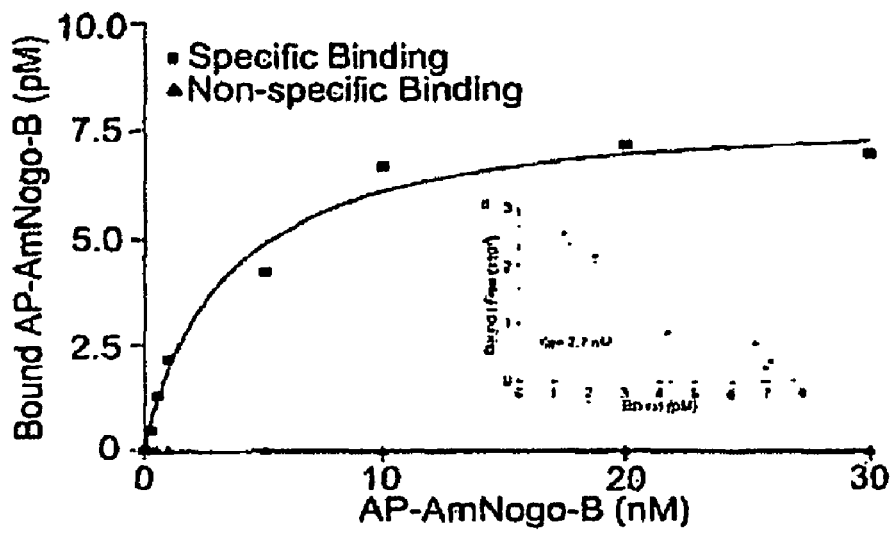
FIG. 7 shows binding of AP-Am-Nogo-B to the surface of CHO cells expressing NgBR and the related Scatchard plot.
Figure 8:
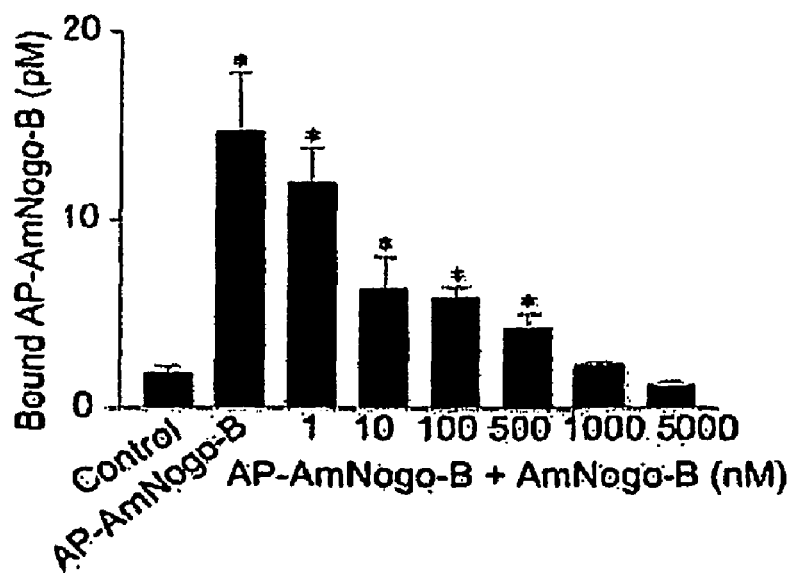
FIG. 8 shows the binding of AP-Am-Nogo-B to CHO cells expressing NgBR and competition by increasing concentrations of purified Am-Nogo-B.

Transient transfection of the NgBR cDNA into CHO cells allowed for the specific, saturable, high-affinity binding similar to that seen in the endothelial cells. The estimated $K_d$ was 2.74 nM (FIG. 7). As shown in FIG. 8, purified Am-Nogo-B dose-dependently displaced the binding of 10 nM AP-Am-Nogo-B from the transfected CHO cells, which suggests that these ligands compete for the same binding site.

Figure 9:
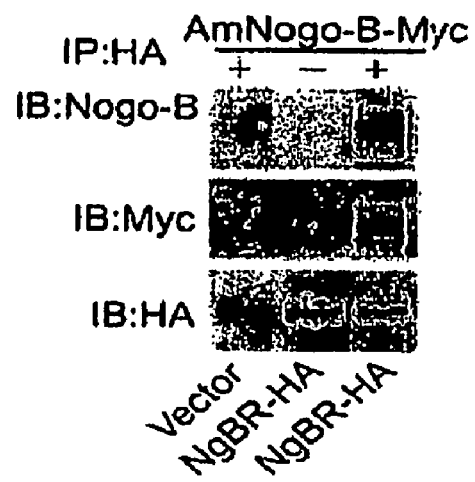
FIG. 9 shows extracts of CHO cells expressing control vector or NgBR-HA incubated with or without purified Am-Nogo-B (+ or −) and then immunoprecipitated with anti-HA matrix.
Figure 10:
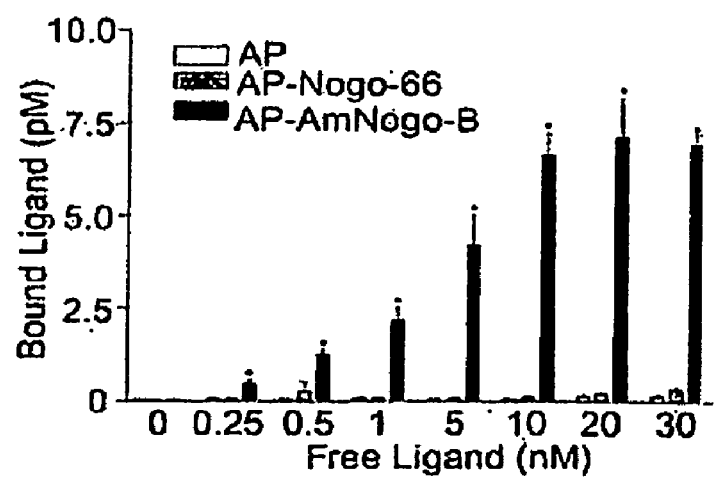
FIG. 10 shows the preferential binding of AP-Am-Nogo-B to CHO cells expressing NgBR, as compared to AP and AP-Nogo-66.

Lysates prepared from vector or Ng-BR-HA-transfected CHO cells were mixed with purified Am-Nogo-B-myc and HA-tagged receptor immunopurified. As shown in FIG. 9, Am-Nogo-B, detected with Nogo-B and anti-myc antisera, interacted with lysates only when the receptor was expressed (compare lane 1 with lane 3). As shown in FIG. 10, where increasing concentrations of recombinant AP, AP-Nogo-66 or AP-Am-Nogo-B were incubated with CHO cells expressing NgBR for 2 hours at 4° C., stable expression of the receptor in CHO cells permits the binding of AP-Am-Nogo-B but not AP or AP-Nogo-66.

Example 2

Characterization of Regions of Nogo-B Responsible for Binding to NgBR

Figure 11:
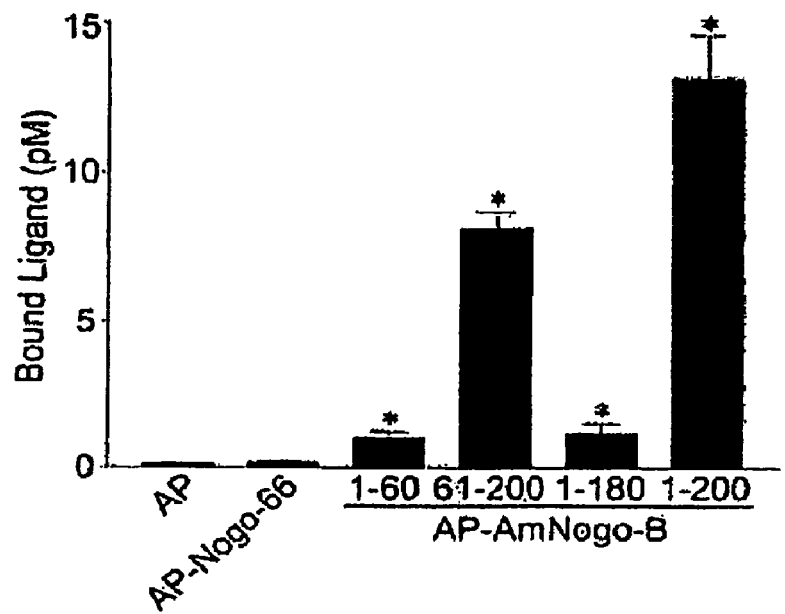
FIG. 11 shows surface binding of AP-Am-Nogo-B domains to CHO cells expressing NgBR.
Figure 12:
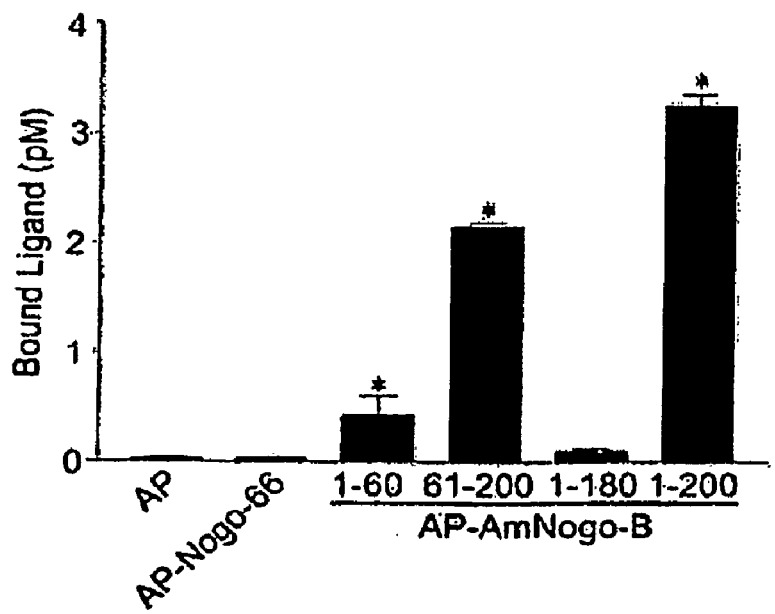
FIG. 12 shows surface binding of AP-Am-Nogo-B domains to HUVEC.
Figure 13:
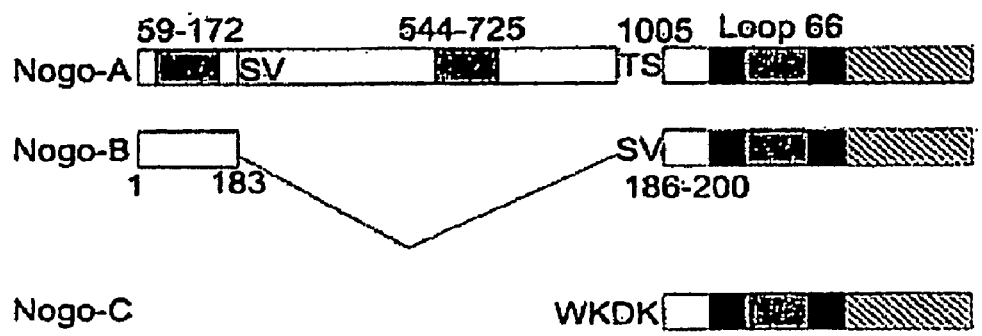
FIG. 13 shows alignments of three Nogo isoforms, Nogo-A, Nogo-B and Nogo-C.
Figure 14:
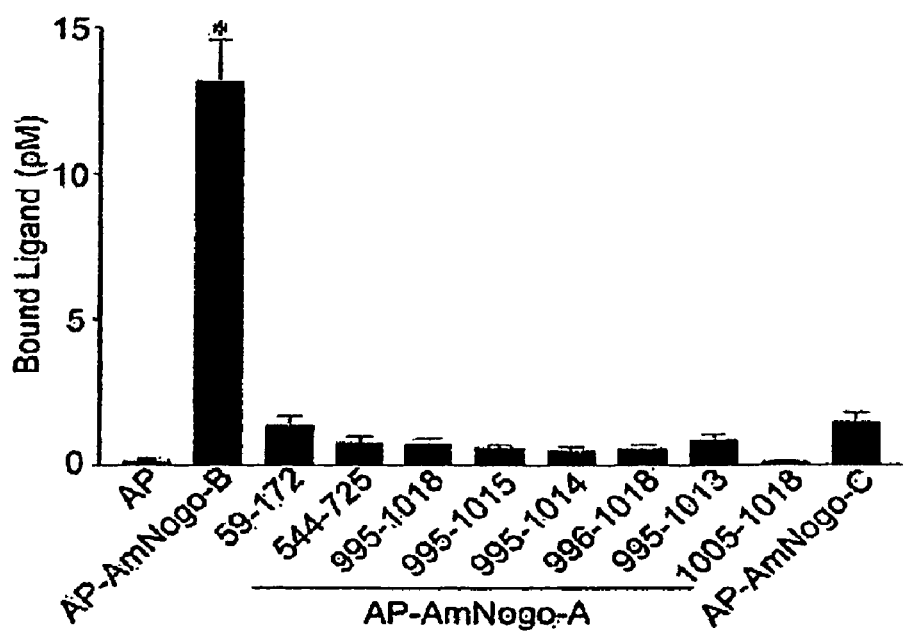
FIG. 14 shows surface binding of AP-Am-Nogo-A domains or Am-Nogo-C to CHO cells expressing NgBR.
Figure 15:
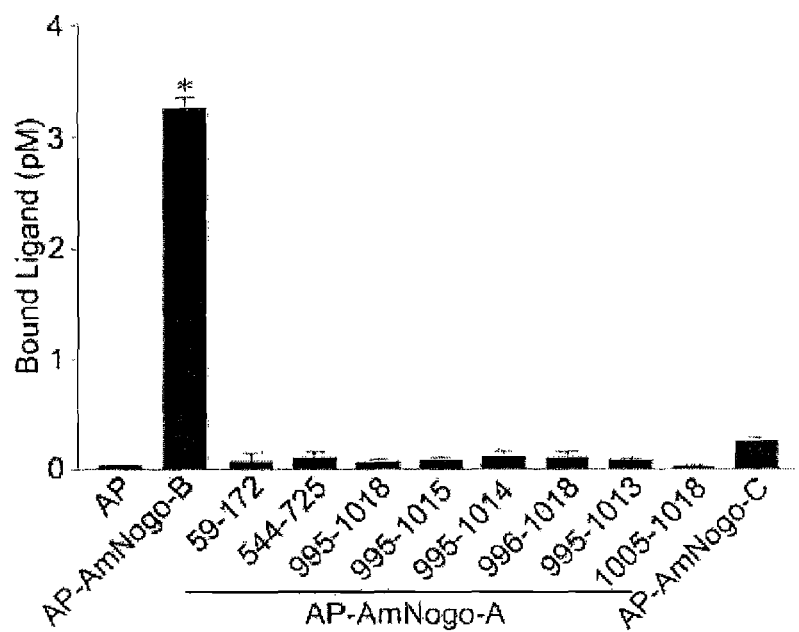
FIG. 15 shows surface binding of AP-Am-Nogo-A domains or Am-Nogo-C to HUVEC.

As shown in FIGS. 11 and 12, AP, AP-Nogo-66 and AP-Nogo-B (amino acids 1-180) did not bind to the receptor, whereas constructs expressing Ap-Nogo-B (61-200) or full-length AP-Am-Nogo-B did. This suggests that amino acids between 180 and 200 were critical for binding in NgBR-expressing cells (FIG. 11) and HUVEC (FIG. 12). However, the stretch of aspartates and glutamates from amino acids 32-51 found in Am-Nogo-A and -B are not believed to be critical based upon these results. FIG. 13 illustrates that amino acids 1-183 are identical in Nogo-A and Nogo-B. In addition, amino acids 1005-1019 in Nogo-A are identical to amino acids 186-200 in Nogo-B and amino acids 12-26 in Nogo-C. However, as shown in FIGS. 14 and 15 (in NgBR-expressing cells and HUVEC, respectively), biologically active domains AP-Nogo-A (59-172) and AP-Nogo-A (544-725) did not bind to NgBR, suggesting that these ligands probably bind to a unique, unidentified receptor. In addition, constructs expressing several regions of Nogo-A overlapping with regions of identity in Nogo-B, as well as the amino terminus of Nogo-C (amino acids 1-26), do not bind to NgBR strongly, suggesting that the cloned receptor expressed in HUVEC is specific for Am-Nogo-B as a ligand. However, it is possible that NgBR may serve as a coreceptor for native full-length Nogo-A.

Example 3

Antibody to NgBR

The peptide CRNRRHHRHPRG (SEQ ID NO:6) was used to immunize rabbits. The antiserum was purified by using the same peptide-conjugated SulfoLink Coupling Gel (Pierce) to obtain a polyclonal antibody. The antibody was diluted 1:500 for immunoblots.

Figure 16:
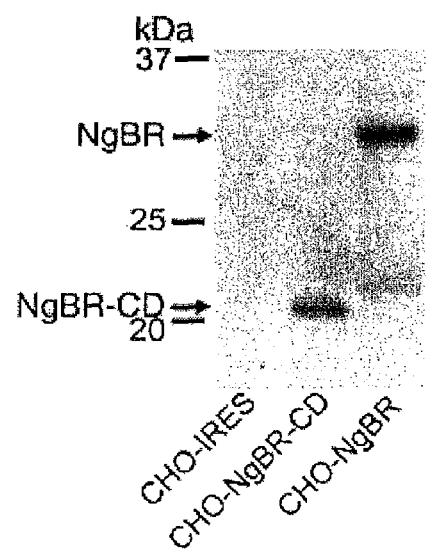
FIG. 16 shows that a polyclonal antibody to NgBR binds both NgBR and NgBR lacking the cytoplasmic domain.
Figure 17:
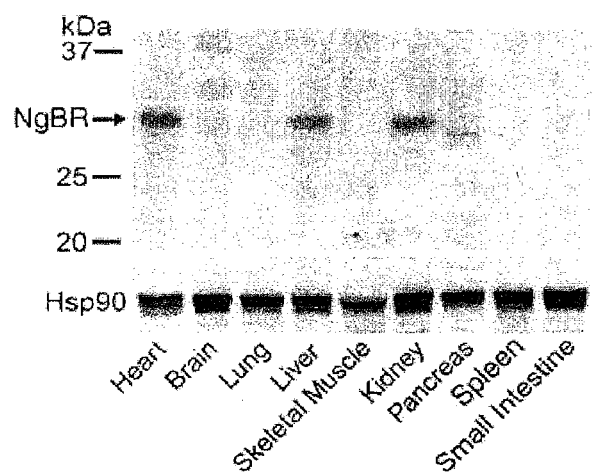
FIG. 17 shows the distribution of NgBR protein in mouse tissues.

CHO cells transfected with vector alone did not exhibit immunoreactivity to the antibody, whereas CHO cells expressing a truncated form of NgBR lacking the cytoplasmic domain (amino acid residues 181-293) and wild-type NgBR yielded the predicted molecular masses of 21 and 30 kDa, respectively (FIG. 16). As shown in FIG. 17, NgBR protein is highly expressed in mouse heart, liver, kidney and pancreas.

Example 4

Role of Nogo-B and NgBR in Angiogenesis

Adenovirus encoding murine VEGF-A 164 ($10^9$ viral particles) were injected intradermally into the right ears of CD1 mice. The left ears were injected with the same amount of control virus encoding beta-gal. At the different time points, animals were killed and the ears removed and embedded in optimal cutting temperature compound (Tissue-Tek, Sakura, Torrance, Calif.). A full-thickness wound about 5 mm in diameter was created by excising the skin and the underlying panniculus carnosus in C57B16 mice. At 10 days after wounding, skin biopsy specimens from six mice were collected for immunohistochemistry analysis. Frozen sections (7 μm) were immunostained with goat polyclonal anti-Nogo-B (Imgenex, San Diego, Calif.) and rat monoclonal anti-mouse PECAM-1 (BD Biosciences-Pharmigen) primary antibodies and Alexa Fluor 568 donkey anti-goat-, Alexa Fluor 488 donkey anti-rabbit- and Alexa Fluor 647 chicken anti-rat-conjugated secondary antibodies (Invitrogen).

Angiogenesis was also investigated in a model where adenoviral VEGF (Ad-VEGF) was intradermally injected into the ear.

Figure 18:
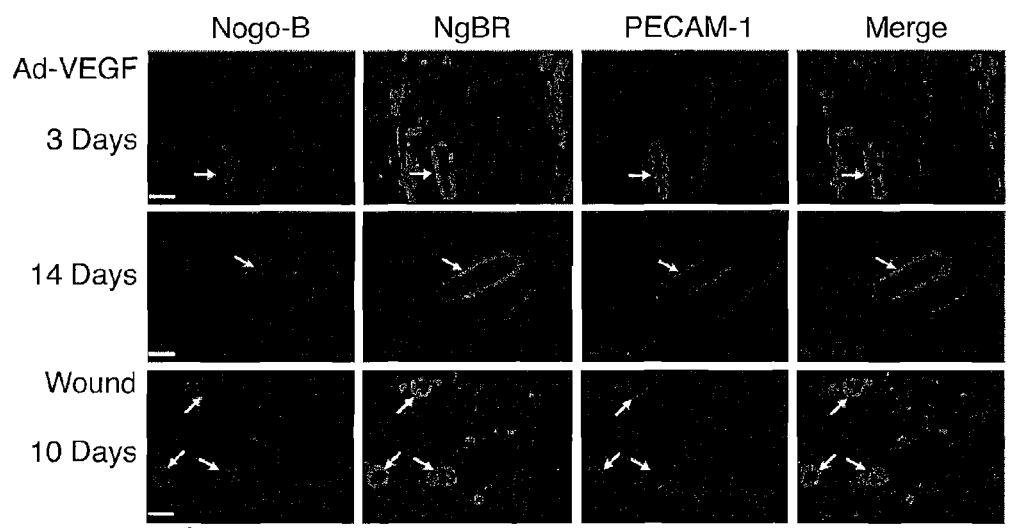
FIG. 18 shows the localization of Nogo-B, NgBR and PECAM-1 in angiogenic blood vessels.

As shown in FIG. 18, Nogo-B and NgBR are present in both endothelial cells and pericytes in a subset of growing (day 3) and more mature (day 14) angiogenic vessels. Immunoreactive Nogo-B and NgBR were found in a subset of PECAM-1-positive endothelial cells at both time points.

In the wound healing model, Nogo-B and NgBR colocalized with PECAM-1-positive endothelial cells after 10 days of wound healing (FIG. 18).

Example 5

Topography of NgBR

Figure 19:
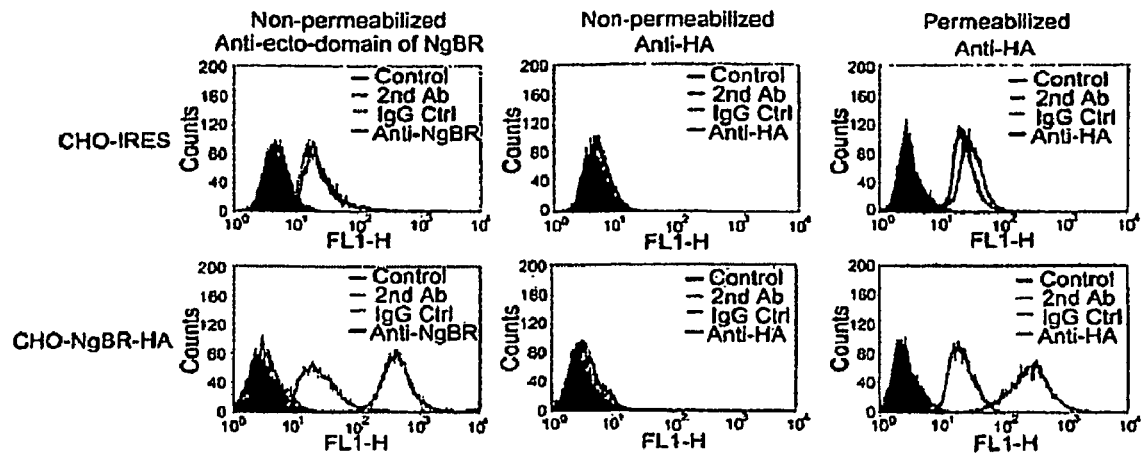
FIG. 19 shows surface immunostaining of NgBR by flow cytometry and sorted by fluorescence-activated cell sorting.

Fluorescence-activated cell sorting analysis of CHO cells expressing vector alone [CHO-internal ribosomal entry site (IRES)] or CHO cells stably expressing full-length NgBR with a C-terminal HA tag (CHO-NgBR-HA) was performed. As shown in the upper portion of FIG. 19, there was non-specific labeling with all antibodies tested in both nonpermeabilized and permeabilized CHO-IRES cells. In contrast, as shown in the lower portion of FIG. 19, in non-permeabilized cells expressing NgBR-HA, anti-NgBR detected a surface epitope and labeling with anti-HA was identical to nonimmune IgG control antisera, defining the N-terminal epitope on the cell surface. Permeabilization of the cells permitted detection of the C-terminal HA epitope. These results are consistent with the predicted topography of the cloned cDNA with the N-terminus extracellular and the C-terminus intracellular.

Example 6

Function of NgBR

Chemotaxis

Figure 20:
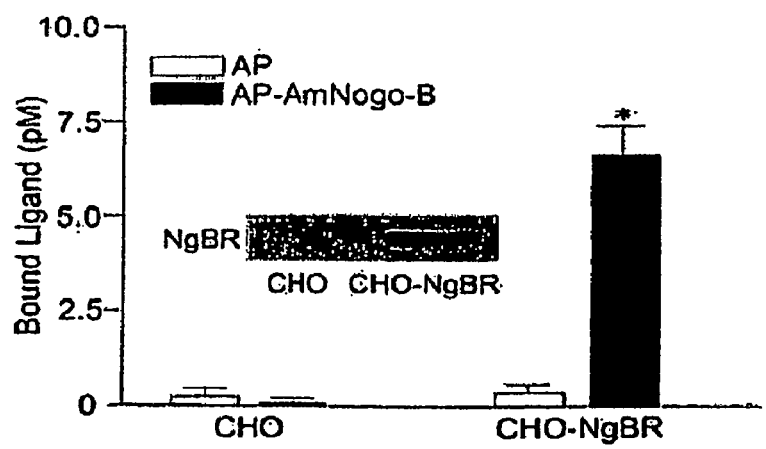
FIG. 20 shows the establishment of stable CHO cell lines expressing NgBR and the levels of NgBR protein determined by Western blotting.
Figure 21:
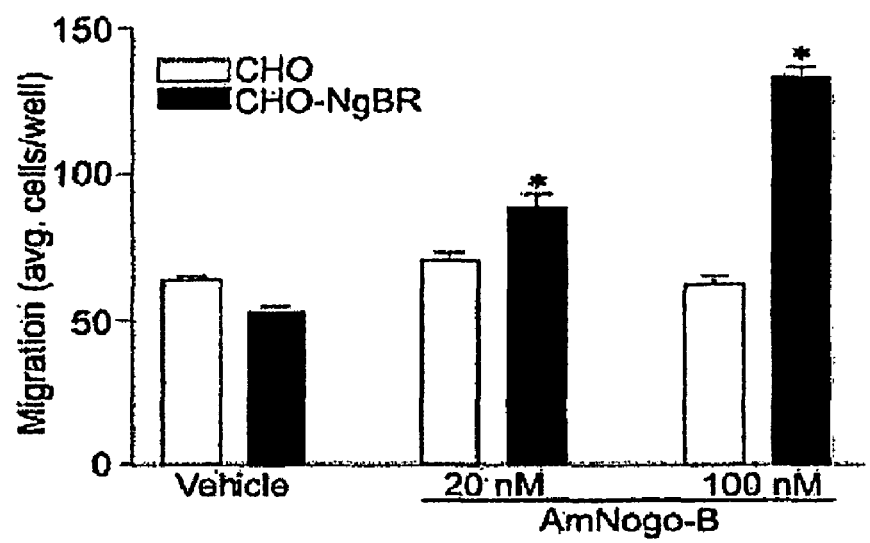
FIG. 21 shows Am-Nogo-B induced chemotaxis in CHO cells expressing NgBR.

There was minimal binding of AP and AP-Am-Nogo-B to CHO cells. CHO cells stably transfected with the cDNA for NgBR permitted binding of AP-Am-Nogo-B (FIG. 20). Using the method described above, CHO cells and CHO cells expressing NgBR were placed into a Boyden chamber and the chemotactic response to soluble Am-Nogo-B was examined. As shown in FIG. 21, transfection of NgBR was required for Am-Nogo-B-mediated chemotaxis. While Applicants do not wish to be bound by theory, this suggests that the cloned receptor is essential for ligand binding and signal transduction.

siRNA

NgBR siRNA oligonucleotides (SEQ ID NOS:2-5) with 3' dTdT overhangs were synthesized by Qiagen. Control siRNA in experiments refers to a nonsilencing (NS) siRNA (NS forward: UUCUCCGAACGUGUCACGU, SEQ ID NO:7; NS reverse: ACGUGACACGUUCGGAGAA, SEQ ID NO:8) designed and synthesized by Qiagen. HUVEC and CHO stable cell lines were transfected with siRNA by using Oligofectamine. Quantification of NgBR mRNA and protein, ligand binding assay, and migration assay were performed at 72 hours after transfection.

Total RNA from cells was isolated by using the RNeasy kit (Qiagen). Reverse transcription was then performed by using 100 ng of RNA and the Superscript First-Strand Synthesis System kit (Invitrogen). Real-time PCR analysis was done with the iCycler iQ detection system using the iQ SYBR green Supermix kit (Bio-Rad). The NgBR mRNA level was normalized by housekeeping gene 18S. The following primers were used for NgBR: forward, 5'-TGCCAGTTAGTAGC-CCAGAAGCAA-3' (SEQ ID NO:9) and reverse, 5'-TGAT-GTGCCAGGGAAGAAAGCCTA-3' (SEQ ID NO:10). The following primers were used for 18S: forward, 5'-CGGC-GACGACCCATTCGAAC-3' (SEQ ID NO:11) and reverse, 5'-GAATCGAACCCTGATTCCCCGTC-3' (SEQ ID NO:12).

Figure 22:
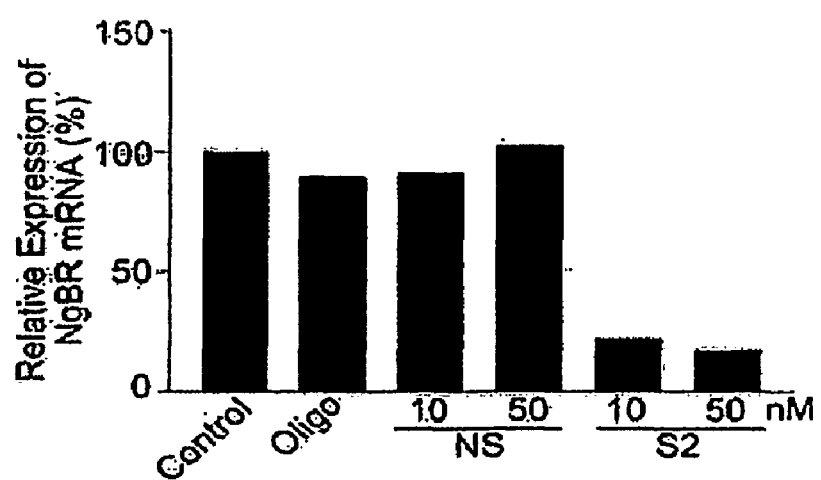
FIG. 22 shows that S2 siRNA downregulates NgBR mRNA levels.
Figure 23:
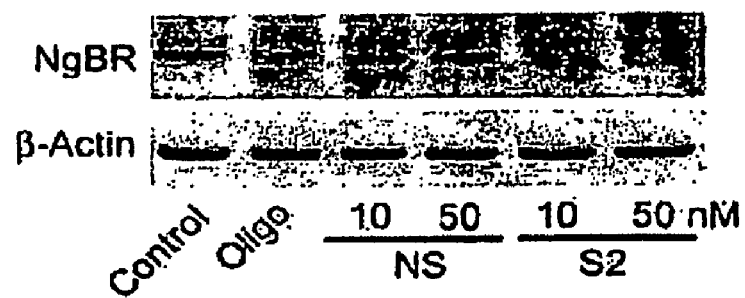
FIG. 23 shows that S2 siRNA downregulates NgBR protein levels.
Figure 24:
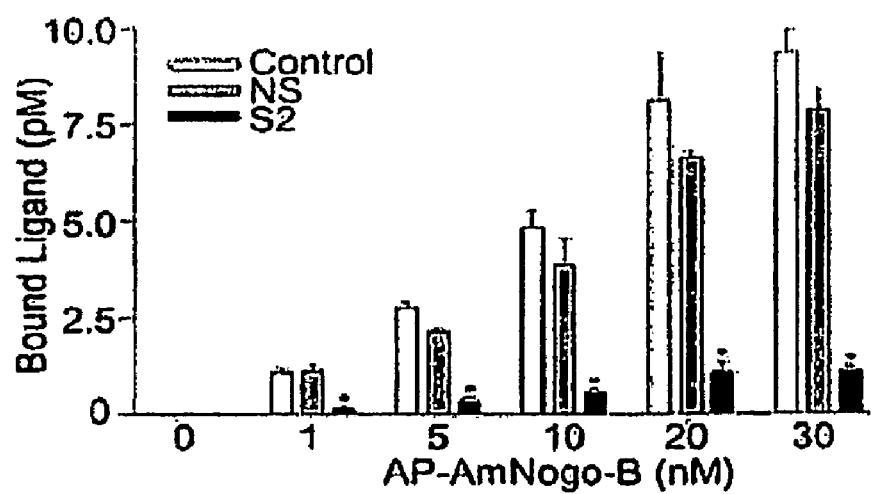
FIG. 24 shows that S2 siRNA abolishes AP-Am-Nogo-B binding to HUVEC.
Figure 25:
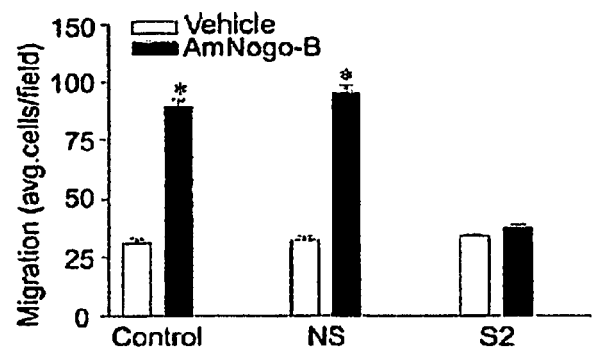
FIG. 25 shows that S2 siRNA abolishes AP-Am-Nogo-B-mediated chemotaxis in HUVEC.
Figure 26:
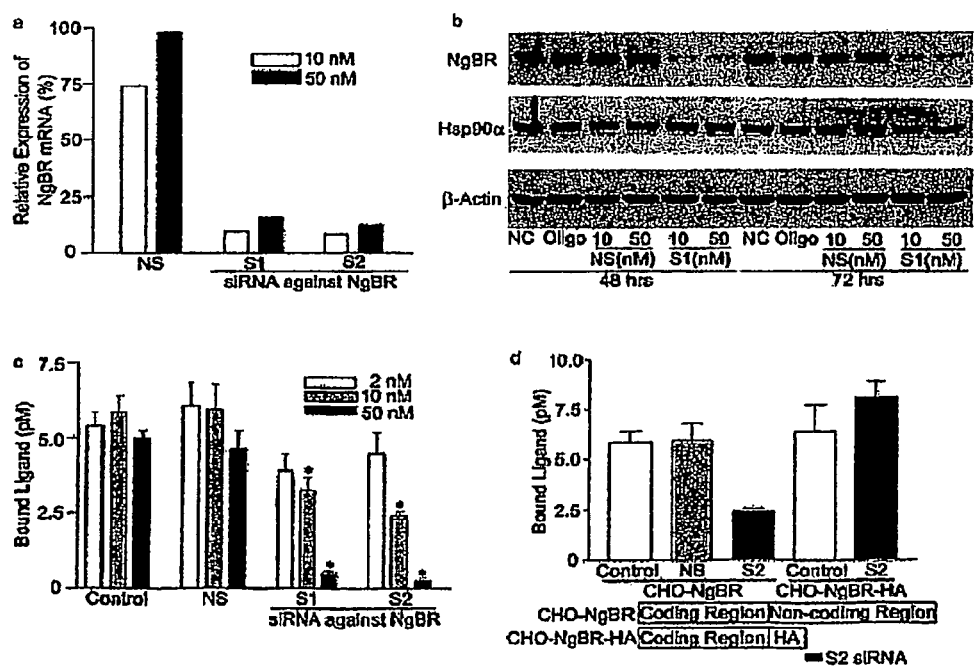
FIG. 26A-C shows that S1 siRNA downregulates NgBR mRNA levels, down-regulates NgBR mRNA protein levels and reduces AP-Am-Nogo-B binding to HUVEC.
FIG. 26D shows that S2 siRNA reduces the binding of AP-Am-Nogo-B in cells expressing the full-length NgBR, but not the HA-tagged form lacking the 3'-untranslated region.

S1 targets the coding region of the mRNA and S2 targets the 3'-untranslated region. The sequences of S1 and S2 are shown above. Treatment of HUVEC with S2 siRNA but not nonsilencing RNA, reduced the level of NgBR mRNA as determined by quantitative PCR (FIG. 22), NgBR protein (FIG. 23) and the binding of AP-Am-Nogo-B (FIG. 24) and abolished Am-Nogo-B-mediated chemotaxis of HUVEC (FIG. 25). S1 has similar effects (FIG. 26A-C). In addition, S2 is specific in its Interactions, as S2 reduced the binding of AP-Am-Nogo-B in cells expressing the full-length NgBR, but not the HA-tagged form lacking the -UTR.

Tubulogenesis

HUVEC were resuspended (final concentration of $1\times10^6$) in a mixture containing rat tail type I collagen (1.5 mg/mL) 1/10 volume of 10×M199 and 1 M Hepes, neutralized with NaOH. Droplets (0.1 mL each) of the cell/collagen mixture were placed in cell culture dishes and allowed to polymerize for 15 minutes at 37° C. Growth medium containing either vehicle or agonist was then added to each well. HUVEC were allowed to form tube-like structures for 1-2 days. To evaluate tube formation in 3-D cultures, cells were photographed using the program OPENLAB (Improvision) and total-network length, defined as an elongation of cell into tube-like structures typically seen in 3-D cultures, was quantified in five fields for each replicate per experiment by using the measurement tools provided with OPENLAB.

Figure 27:
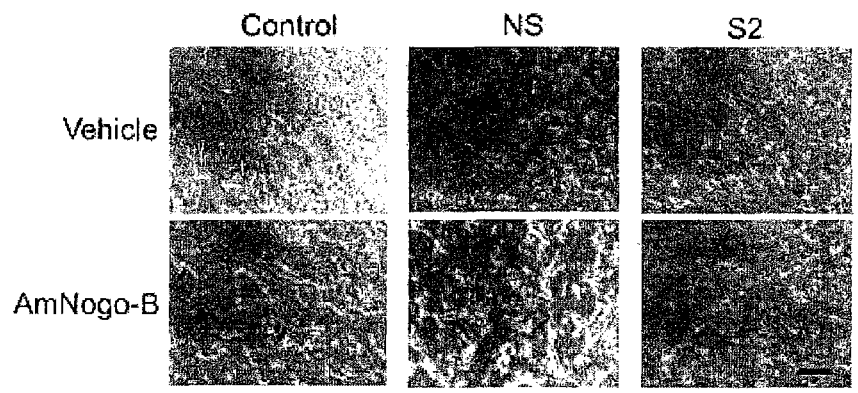
FIG. 27 shows photographs of tube growth in HUVEC treated with NS RNA or S2 siRNA and then vehicle or Am-Nogo-B.
Figure 28:
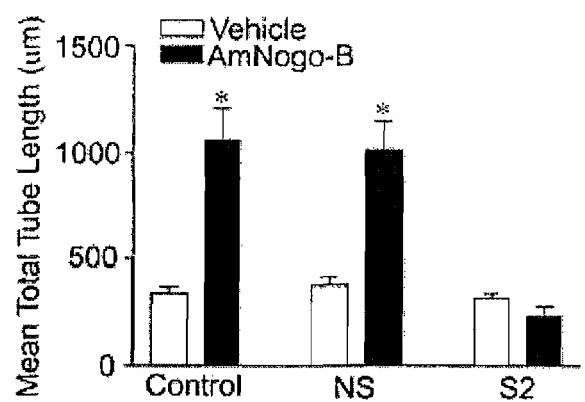
FIG. 28 shows the total network length of HUVEC treated with NS RNA or S2 siRNA and then vehicle or Am-Nogo-B.

Am-Nogo-B (80 nM) stimulated an increase in tube formation, as shown in the phase-contrast images in FIG. 27 and quantified in FIG. 28. The increase in tube formation was attenuated by siRNA S2. It is believed that these data demonstrate that endogenous NgBR is required for the in vitro angiogenic actions of Am-Nogo-B in endothelial cells.

Example 7

Lipid Transferase Activity

NgBR and NgBR lacking the cytoplasmic domain (NgBR-CD) was immunoisolated from CHO cells expressing NgBR-HA or NgBR-CD by using anti-HA matrix beads. Lipid transferase activity was measured by determining the amount of [1-$^{14}$C]IPP (isopentenyl pyrophosphate) incorporated into butanol-extractable polyprenyl diphosphates. The activity was assayed in a 50 µL reaction containing 50 mM Hepes, pH 7.5, 2 mM MgCl$_2$, 5 mM KF, 1 mM DTT, 0.5% CHAPS, 50 µM [1-$^{14}$C]IPP (0.15 µCi per reaction) and 50 µM allylic isoprenoid diphosphate (farnesyl diphosphate, geranylgeranyl diphosphate). The reaction was started by the addition of 1 µg of protein and allowed to proceed for 20 minutes at 37° C. Mouse liver extract (1 µg) was used as a positive control for the assay. The reaction was stopped by the addition of 0.5 mL of 1-butanol saturated with water, followed by the addition of 0.5 of 1-butanol saturated with water, followed by the addition of 0.5 mL of 2 M KCl. An aliquot of the butanol phase was removed for scintillation counting using SafeScint scintillation (American Bioanalytic, Natick, Mass.).

Figure 29:
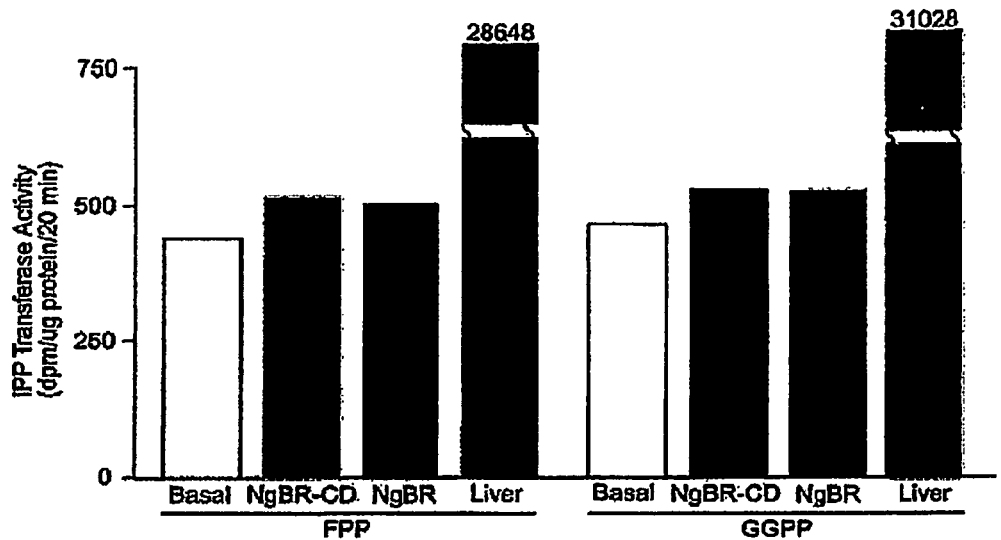
FIG. 29 shows isoprenyl lipid transferase activity of NgBR and NgBR lacking the cytoplasmic domain.

As shown in FIG. 29, direct assays for lipid transferase activity were negative. These results suggest that NgBR may act as a scaffold for the binding of isoprenyl ligands and/or prenylated proteins.

Example 8

Characterization of Peptides Derived from the Ectodomain of NgBR

Figure 30:
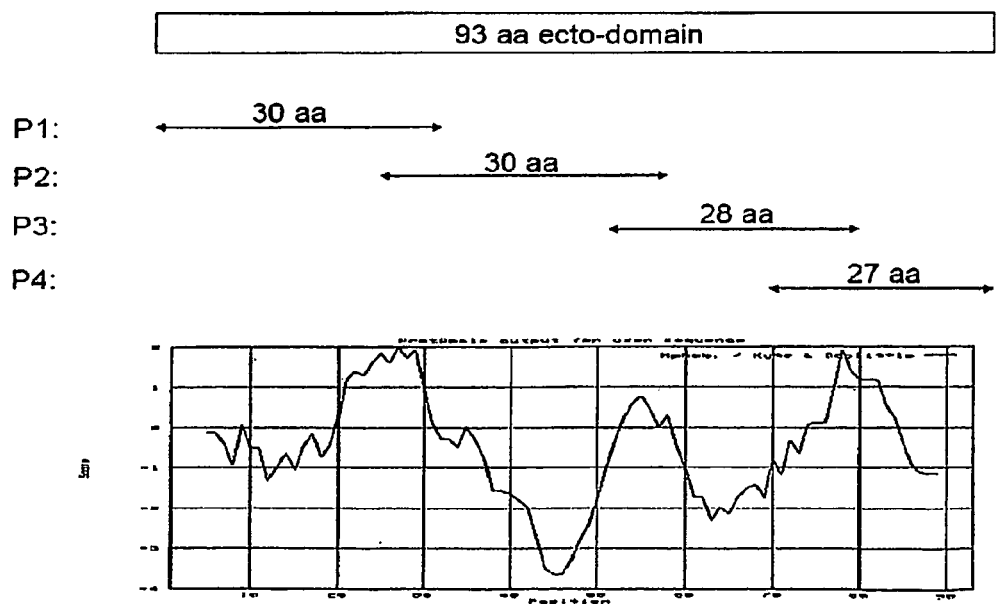
FIG. 30 shows the structure of peptides P1-P4 and a hydropathy plot of the ectodomain of NgBR.
Figure 31:
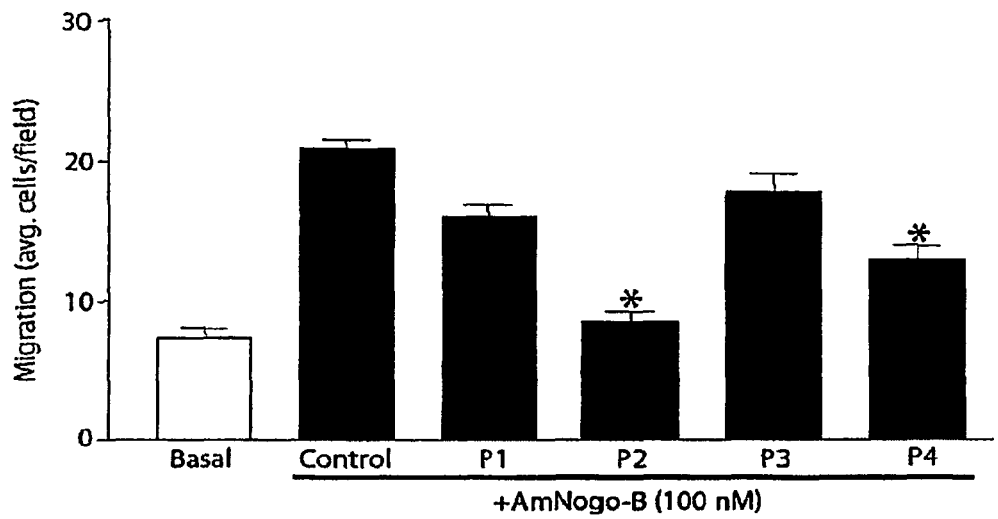
FIG. 31 shows the effect peptides P1-P4 had on migration of endothelial cells.
Figure 32:
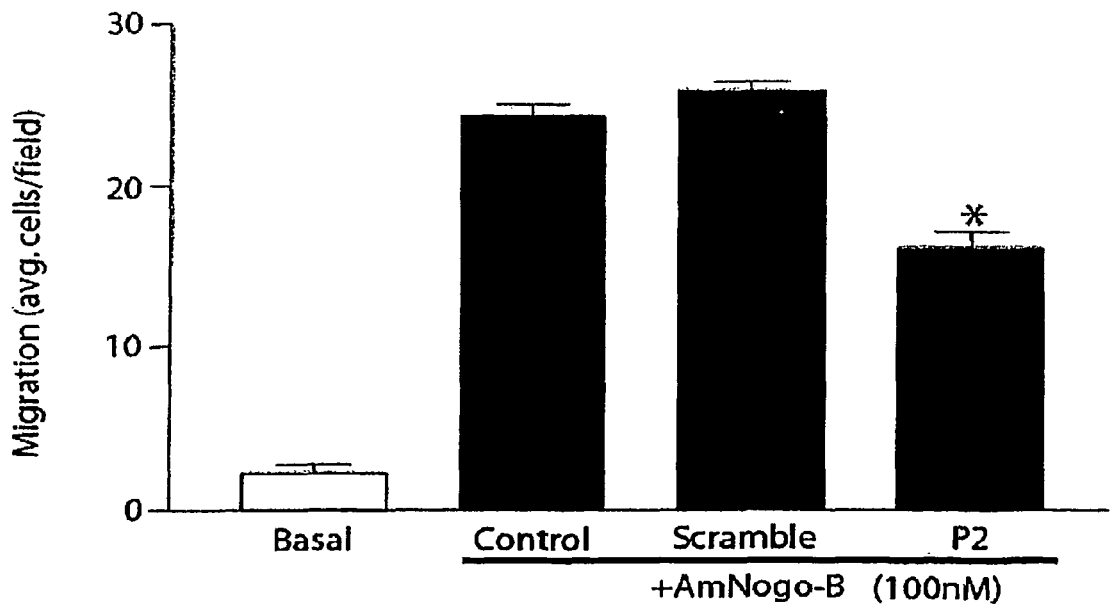
FIG. 32 shows a comparison of the effect P2 and a scrambled version of P2 had on migration of endothelial cells.

FIG. 30 shows a hydropathy plot of amino acid residues in NgBR, along with four overlapping peptides (P1: SWLRVRFGTWNWIWRRCCRAASAAVLAPLG (SEQ ID NO: 13), P2: LAPLGFTLRKPPAVGRNRRHHRHPRGGSCL (SEQ ID NO: 14), P3: GGSCLAAAHHRMRWRADGRSLEKLPVHMGL (SEQ ID NO:15), P4: ADGRSLEKLPVHMGLVITEVEQEPSFSD (SEQ ID NO: 16)) derived from the ectodomain of NgBR. Endothelial cells were incubated with vehicle (control) of one of peptides P1-P4 (200 nM each) in the presence of Am-Nogo-B (100 nM). The P2 peptide, and to a lesser extent the P4 peptide, effectively reduced Am-Nogo-B-induced migration (FIG. 31). In contrast, a scrambled version of P2 (PGRHLKPSRFNARLHGPCRVLRAHGPLTRG, SEQ ID NO: 17) did not block endothelial cell migration (FIG. 32). These results suggest that P2 is a competitive antagonist of Nogo-B function.

An additional peptide prepared was a truncated version of P2, TLRKPPAVGRNRRHHRHPRG (SEQ ID NO: 18), known as PP2. PP2 had activity nearly identical to that of P2.

Example 9

Generation of a Soluble NgBR Receptor Body as a Potential Antagonist

Figure 33:
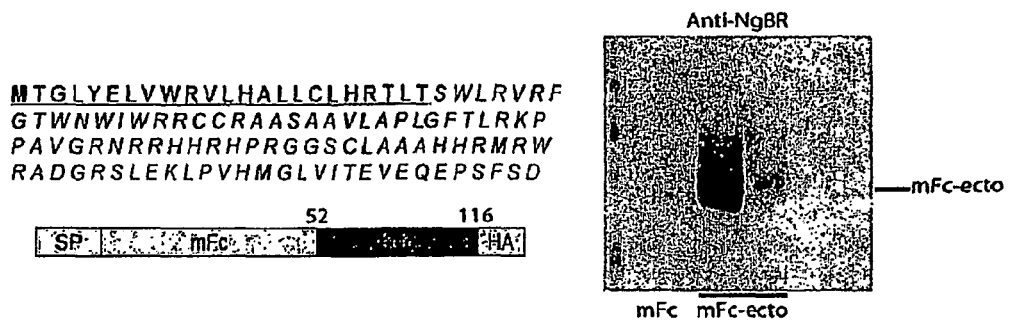
FIG. 33 shows a diagram of a fusion protein that includes the Fc fragment of IgG, amino acids 52-116 of NgBR and HA and binding of the fusion protein to an anti-NgBR antibody.

An Fc fusion of amino acids 52-116 of NgBR (SEQ ID NO:1) was generated and expressed as an HA-, heptahistidine tagged fusion protein (mFc-ecto) in mammalian cells. As shown in FIG. 33, mFc (a control) and mFc-ecto were purified from conditioned media and mFc-ecto was recognized by an anti-NgBR antibody.

Figure 34:
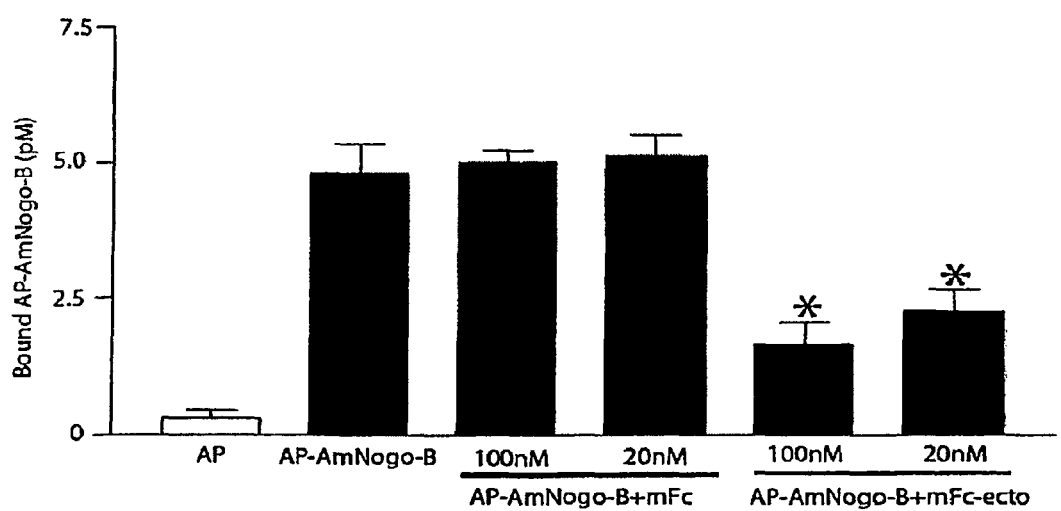
FIG. 34 shows the effect an mFc control and an mFc fusion with the NgBR domain have on the binding of Am-Nogo-B to endothelial cells.

Endothelial cells were incubated with AP-Am-Nogo-B. Binding of AP-Am-Nogo-B to the cells was not blocked by the mFc control, but was blocked by mFc ecto at concentrations of 20 nM and 100 nM (FIG. 34).

Figure 35:
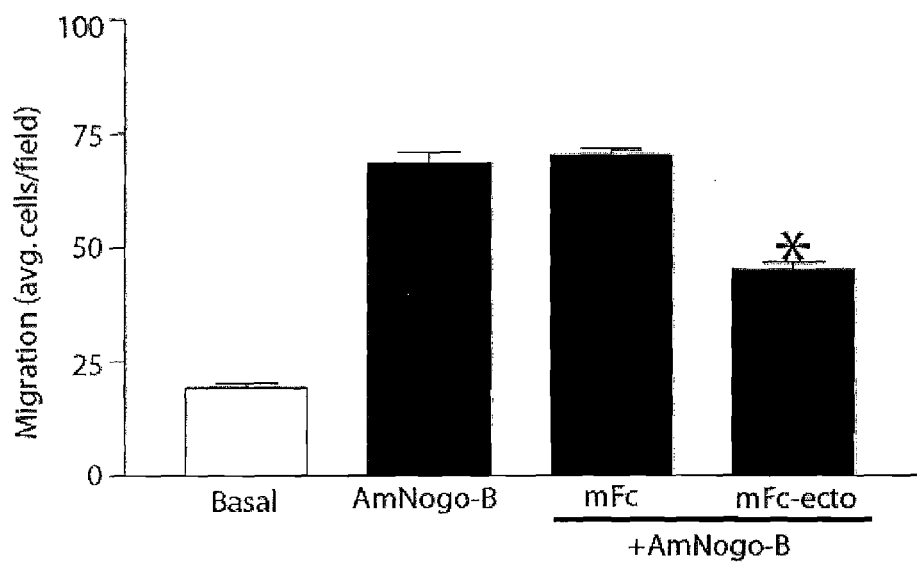
FIG. 35 shows the effect an mFc control and an mFc fusion with the NgBR domain have on the Am-Nogo-B-mediated migration of endothelial cells.

Similarly, treatment of endothelial cells with mFc-ecto, but not mFc, blocked Am-Nogo-B-induced cell migration (FIG. 35).

These results suggest that mFc-ecto is a competitive antagonist for Nogo-B.

Example 10

Figure 36:
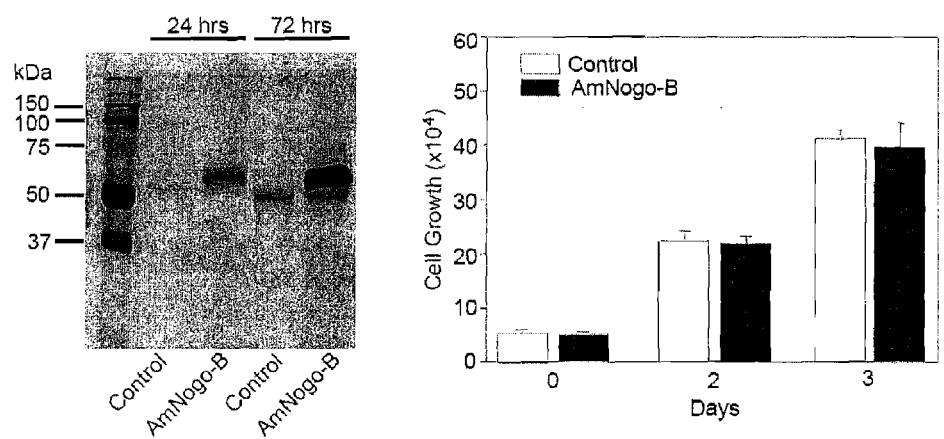
FIG. 36 shows the secretion of Am-Nogo-B in A549 cells engineered to secrete Am-Nogo-B and the effect on cell growth.

Nogo-B Overexpression in Human Tumor Epithelial Cells Increases Tumor Growth and Angiogenesis In Vivo Human A549 cells were stably transfected with vector alone (control) or a vector encoding a secreted form of Am-Nogo-B. The production of Am-Nogo-B and the effects on A549 cell growth in culture were examined. As shown in FIG. 36, A549 cells engineered to secrete Am-Nogo-B showed accumulation of Am-Nogo-B into the media of cells. This secretion of Am-Nogo-B did not effect the basal growth of cells in culture (FIG. 36).

Figure 37:
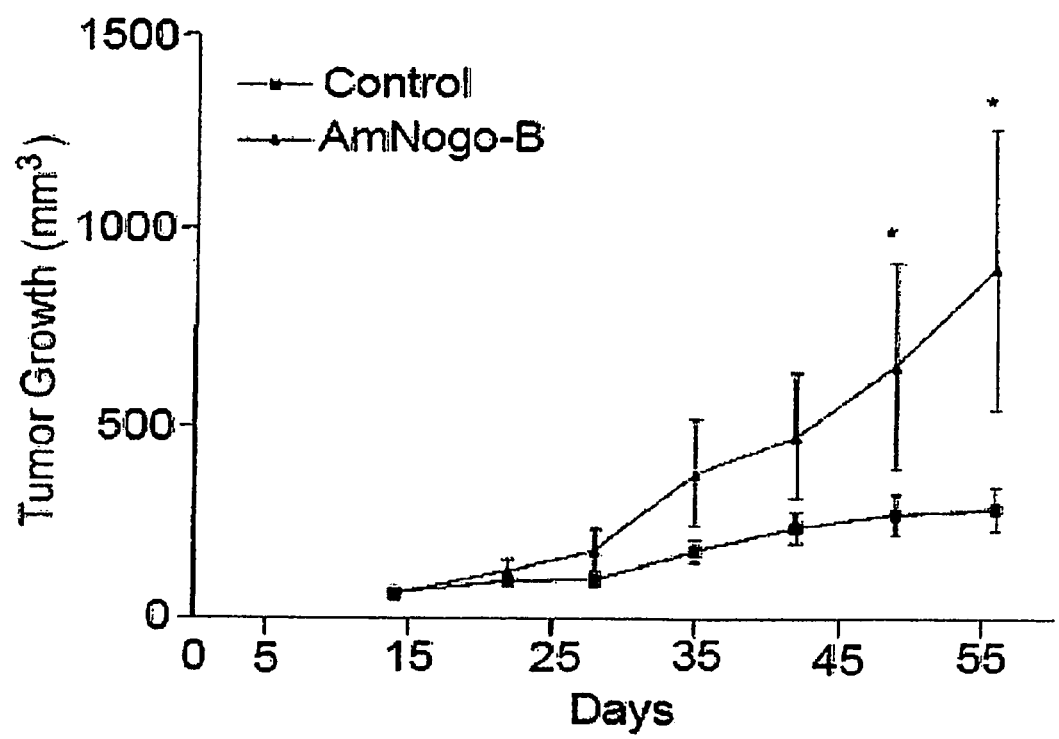
FIG. 37 shows the effect of injecting engineered A549 cells secreting Am-Nogo-B on tumor growth in immunodeficient mice.
Figure 38:
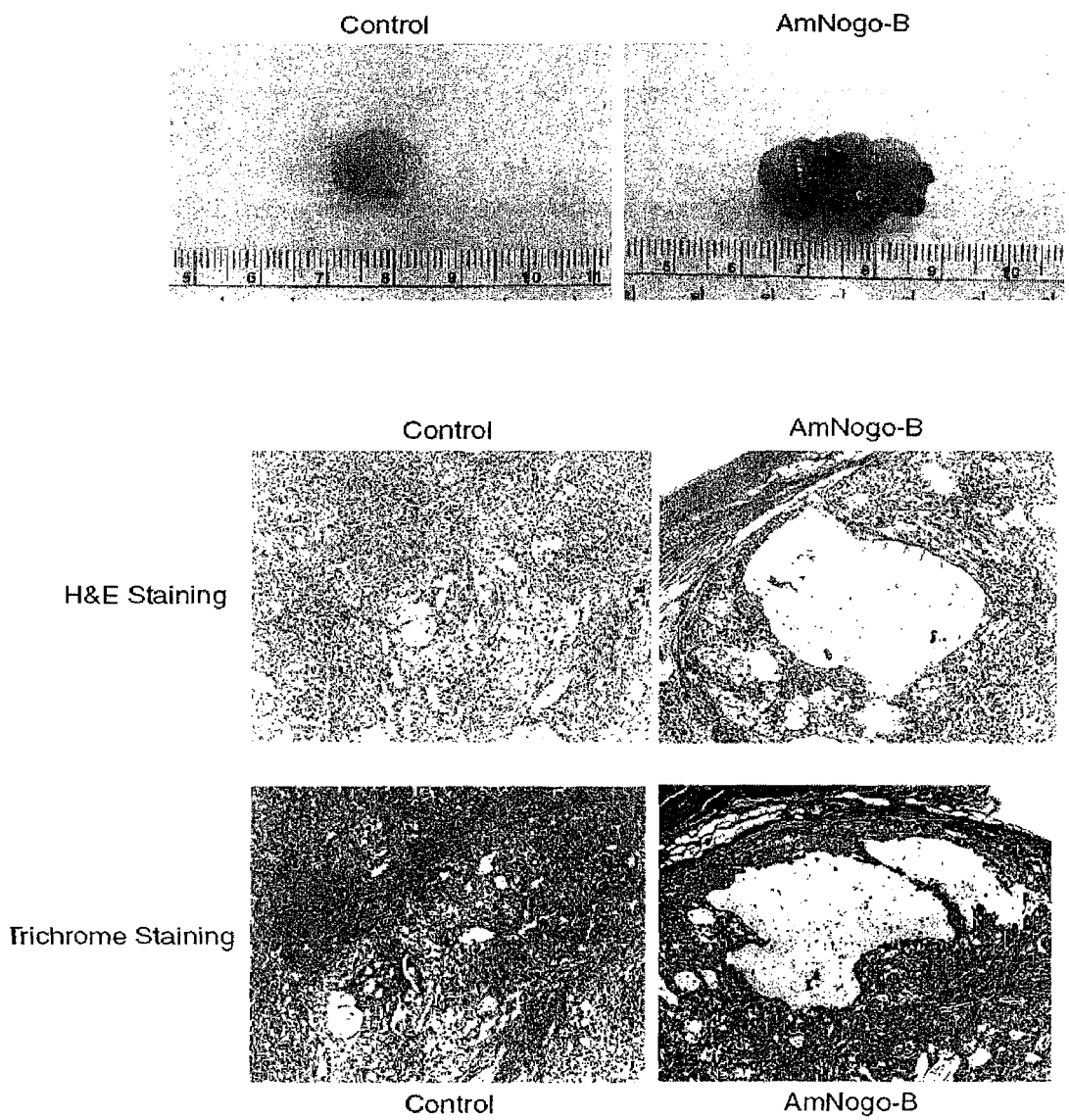
FIG. 38 shows the size of isolated tumors and increases in necrotic zones and changes in the extracellular matrix in tumors of A549 cells engineered to secrete Am-Nogo-B.
Figure 39:
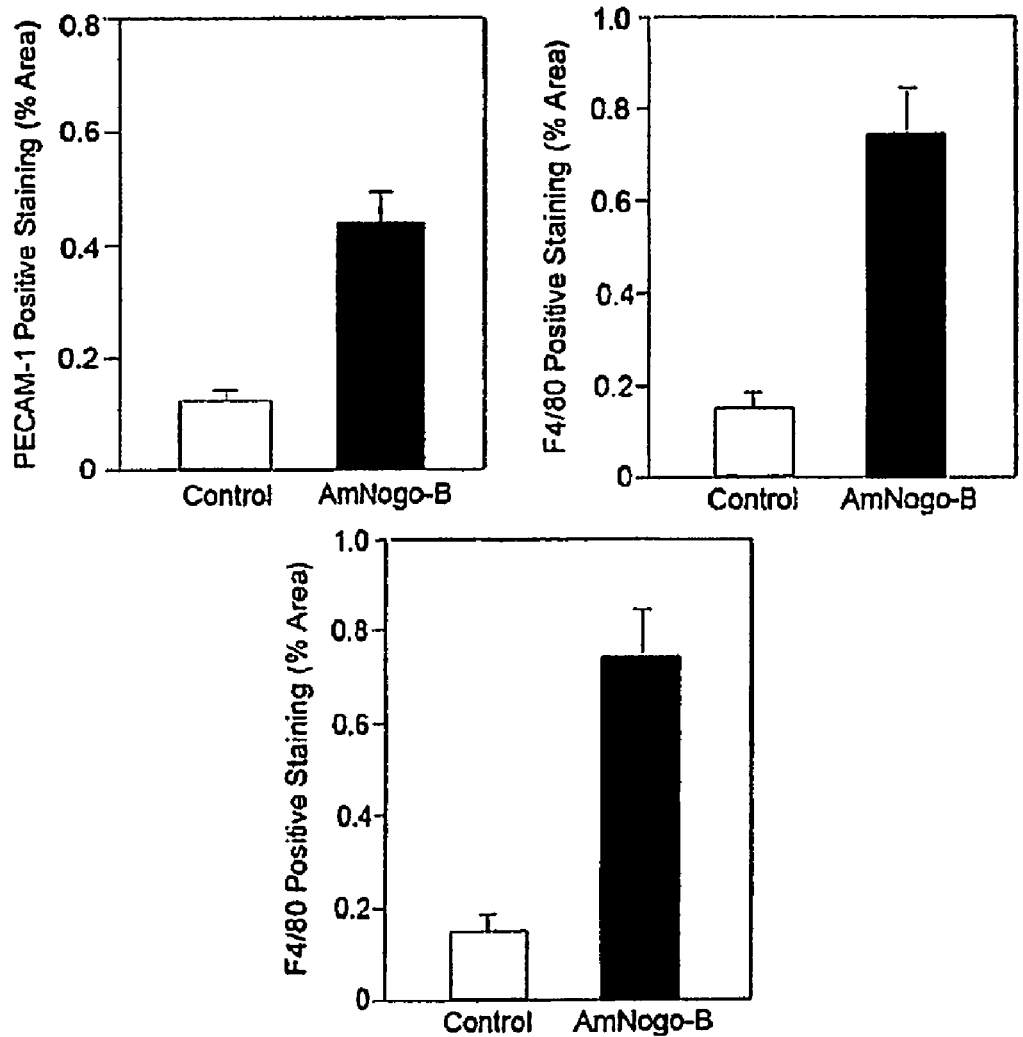
FIG. 39 shows differences in PECAM-1-positive tumor endothelial cells, F4/80 positive cells and LYVE-1-positive staining in control tumor cells and tumors of A549 cells engineered to secrete Am-Nogo-B.

However, injection of the engineered cells into immunodeficient mice increased the growth rate of tumors in vivo and cells expressing Am-Nogo-B produced much larger tumors (FIG. 37). Isolation of the tumors revealed that tumors expressing Am-Nogo-B were larger (FIG. 38, top), had greater necrotic zones according to an H&E stain and changes in the extracellular matrix according to a Trichrome stain (FIG. 38, bottom). The increase in growth of the A549 cells expressing Am-Nogo-B resulted in increased angiogenesis (quantified as PECAM-1-positive tumor cells), increase tumor associated macrophages (F4/80 positive cells) and reduced lymphangiogenesis (LYVE-1 staining) (FIG. 39).

Example 11 mFc-ecto Reduces Tumor Growth In Vivo

Human lung carcinoma cells (A549) (5×10$^6$ cells) in 0.1 mL sterilized RPMI medium were Injected subcutaneously into the dorsa of 6 weeks old, nu/nu male nude mice (Charles River). When the tumors reached a volume of 200 mm$^3$ (typically about 20 days after implantation), an intratumoral injection of 10$^9$ pfu of adenoviruses expressing mFc or mFc-ectodomain residues 52-116 (Ad-mFC or Ad-mFc-NgBR-ectodomain) in PBS was carried out (Li et al., Gene Therapy 5:1105-1113, 1998; Miao et al., Blood 100:3245-52, 2002). Tumor growth was monitored by external measurement of tumors in two dimensions with calipers as previously described (Tsujii et al., Cell 93:705-716, 1998). Tumor volume is determined according to the equation V=[L×W$^2$]×0.5, where V=volume, L=length, and W=width. At the endpoint, mice were anaesthetized and sacrificed. Tumor tissues were collected for histology analysis.

Figure 40:
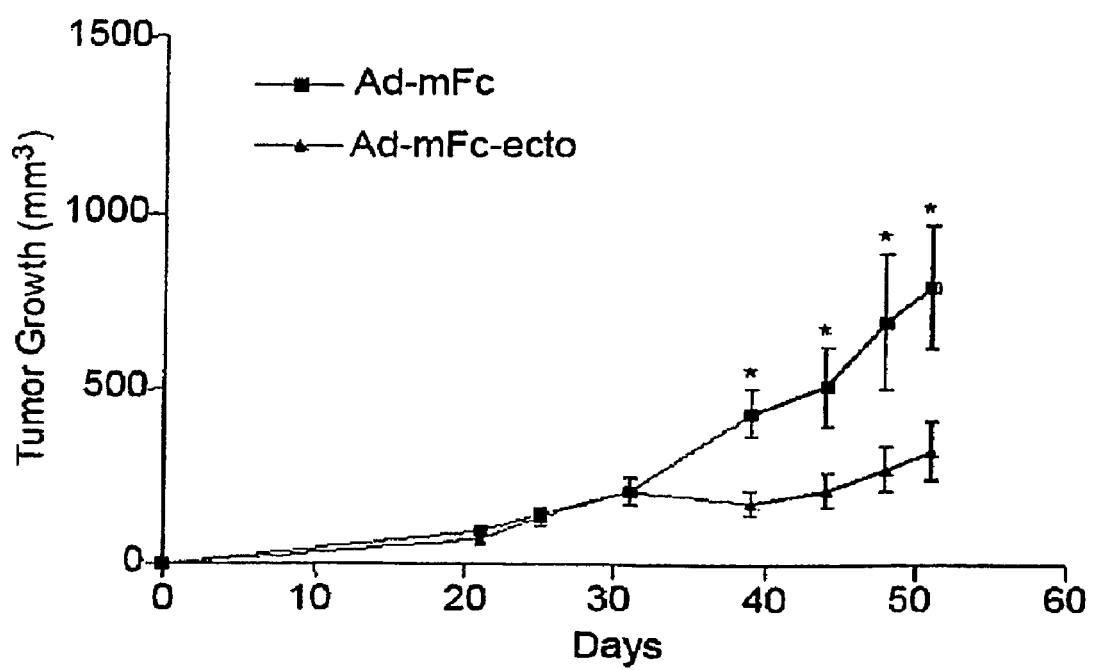
FIG. 40 shows the effect of injecting tumors of Am-Nogo-B-expressing A549 cells with adenoviruses expressing an Fc control (Ad-mFc) or the Fc-NgBR ectodomain fusion (Ad-mFc-ecto).
Figure 41:
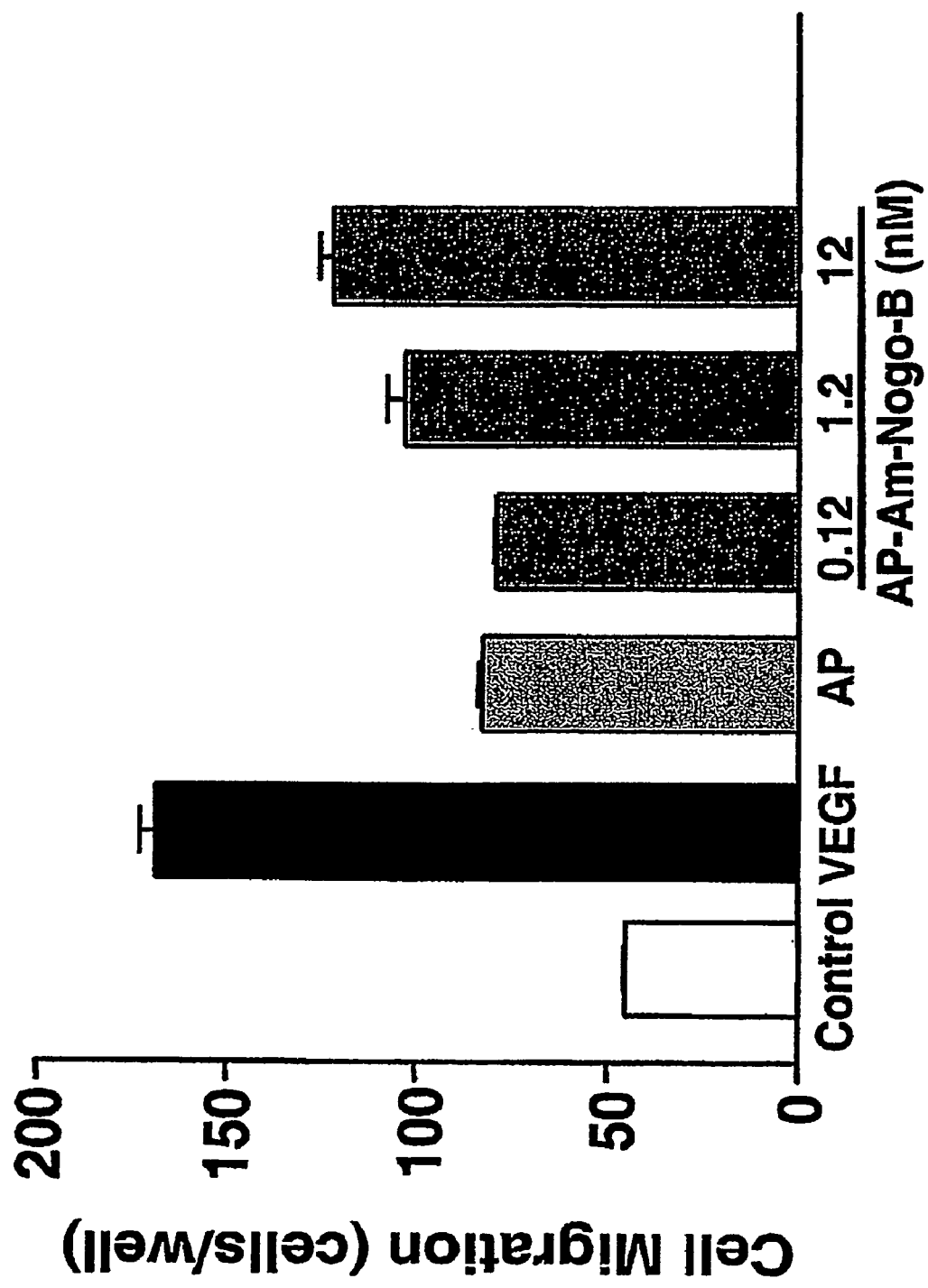
FIG. 41 shows the dose-dependent effects of AP-Am-Nogo-B on the migration of HUVEC.
Figure 42:
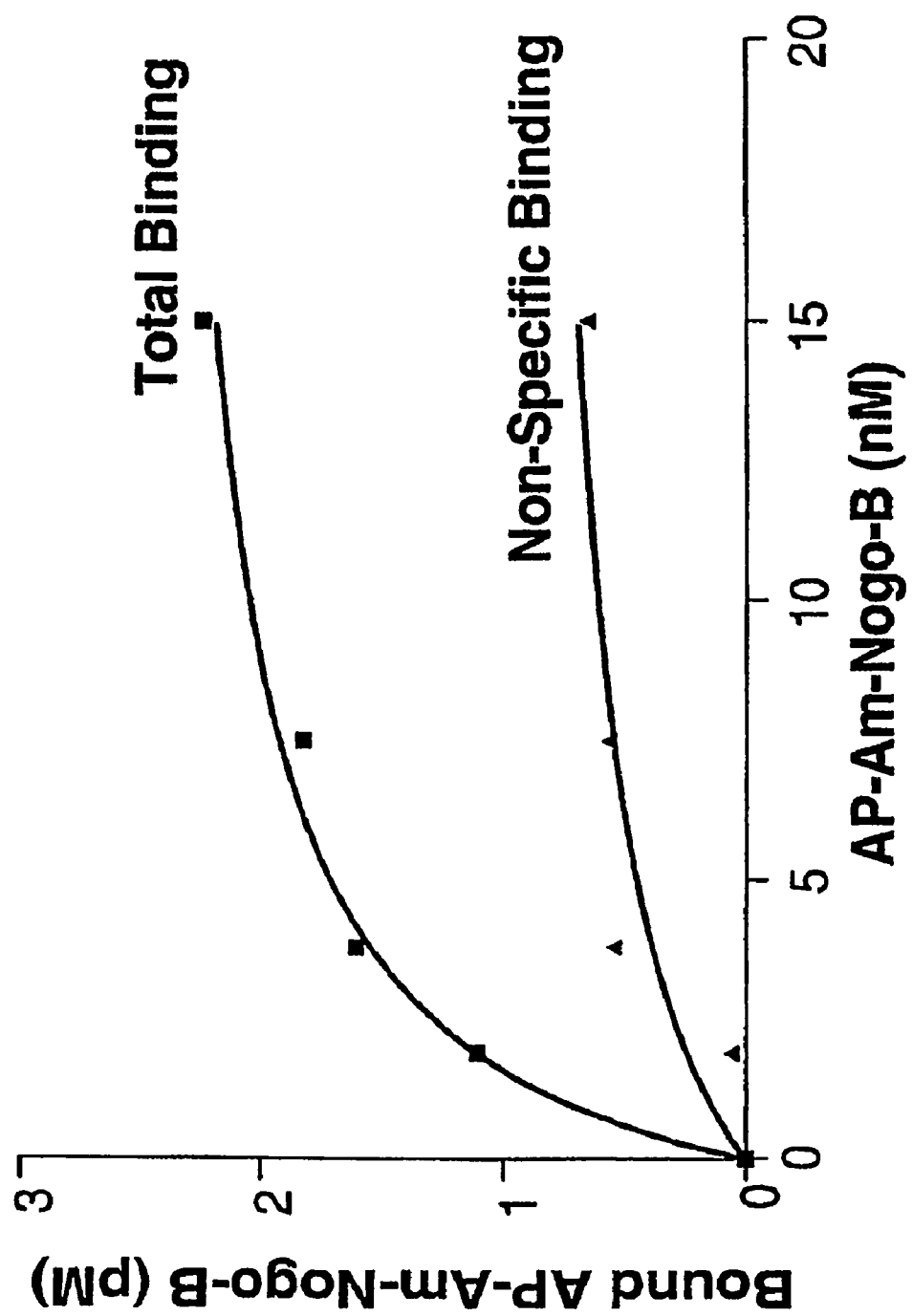
FIG. 42 shows the specific binding of AP-Am-Nogo-B on HUVEC.
Figure 43:
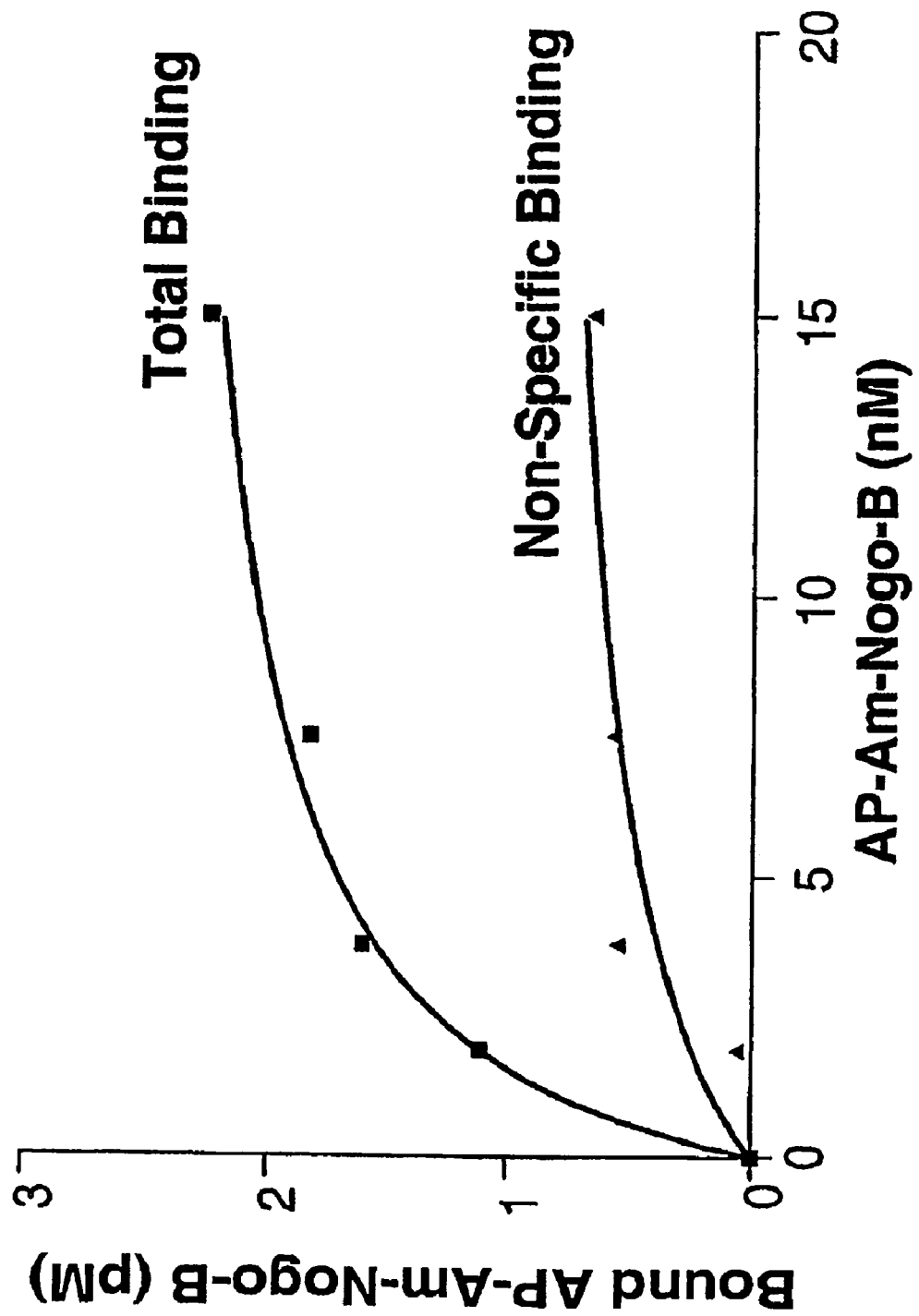
FIG. 43 is a Scatchard plot of AP-Am-Nogo-B binding onto HUVEC.
Figure 44:
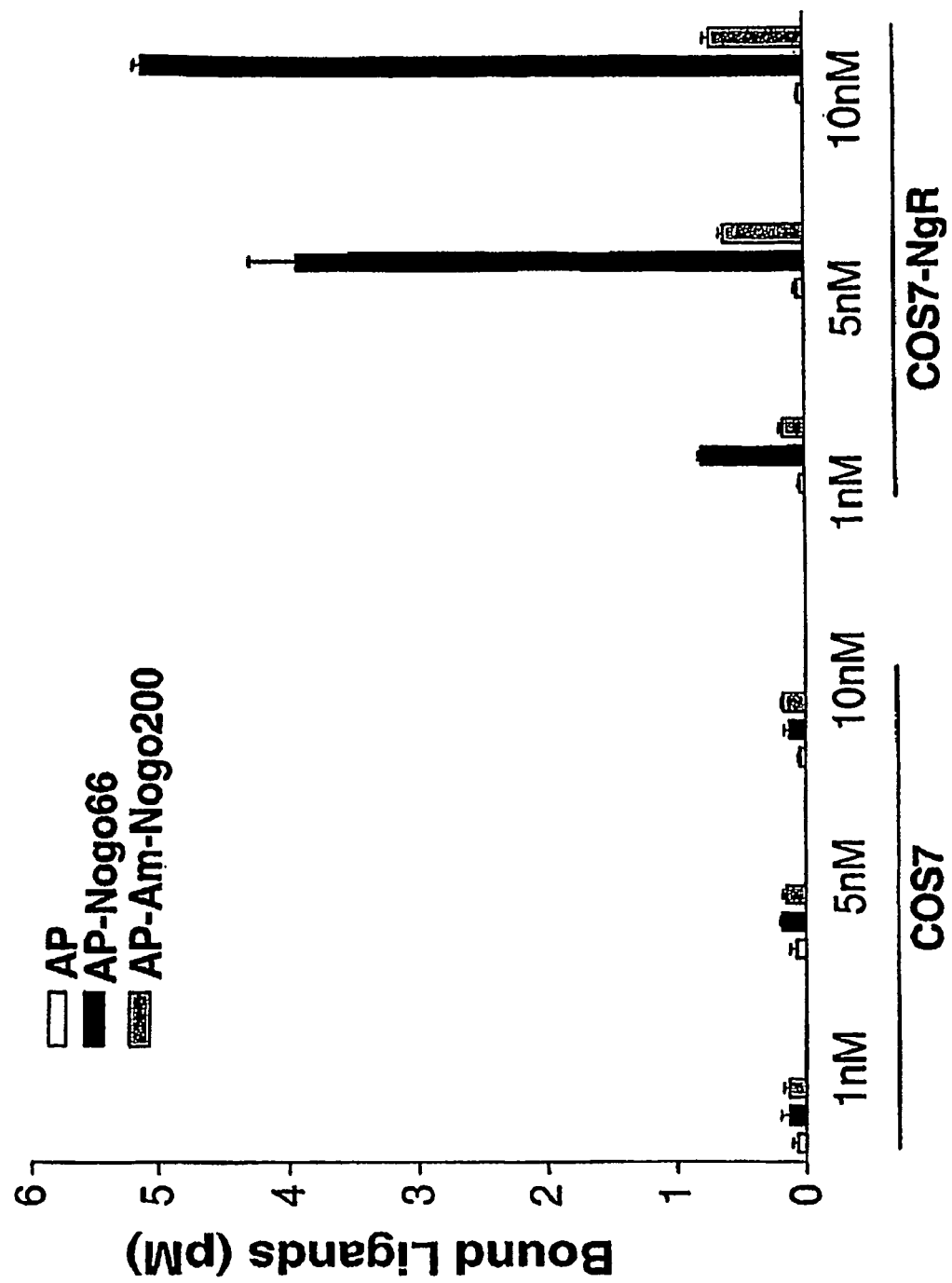
FIG. 44 shows the binding of AP-Nogo-66 and AP-Am-Nogo-B onto COS-7 cells transfected with the cDNA for the Nogo-66 receptor.
Figure 45:
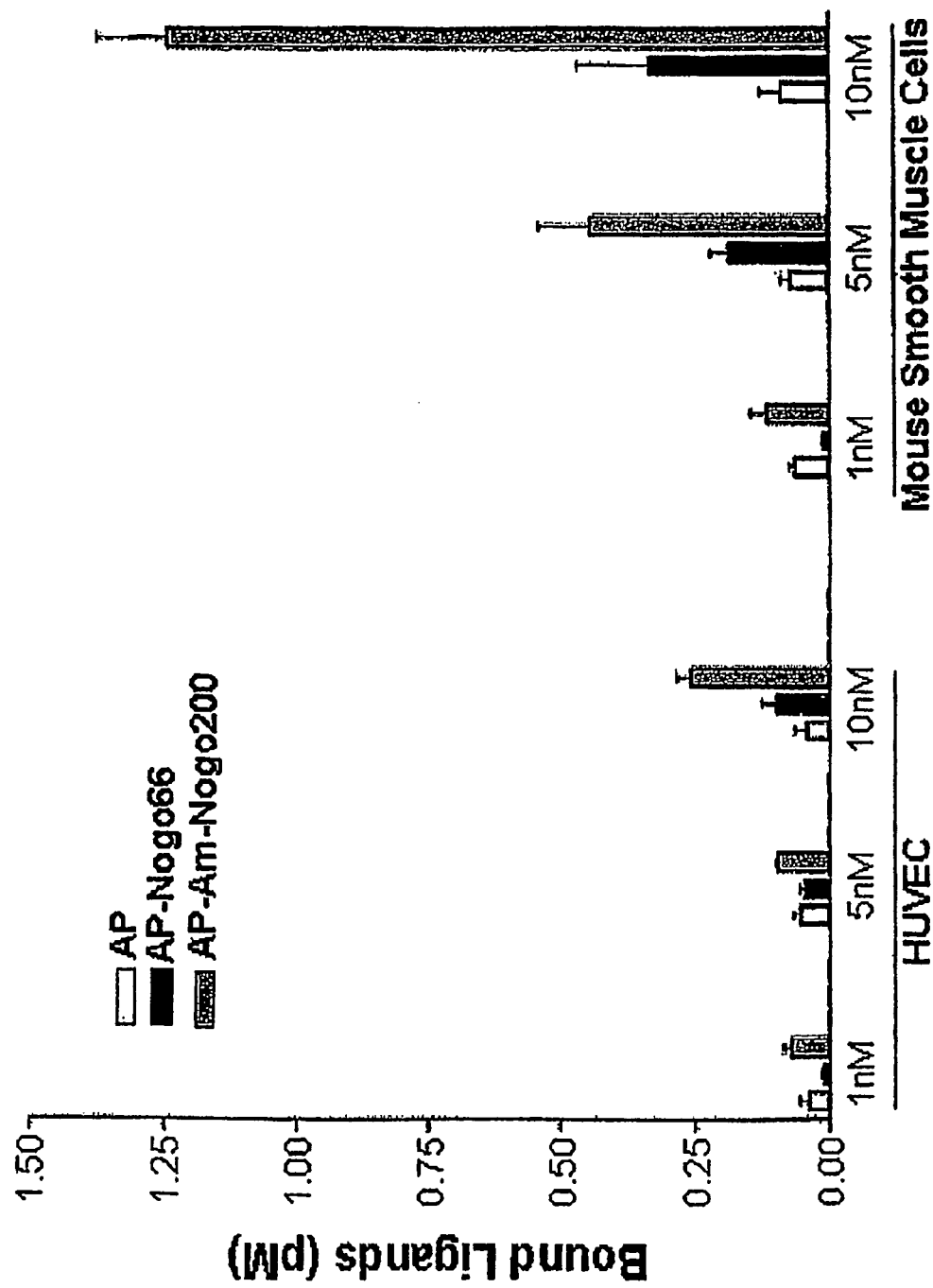
FIG. 45 shows the preferential binding of AP-Am-Nogo-B over AP and AP-Nogo-66 on HUVEC cells and mouse smooth muscle cells.
Figure 46:
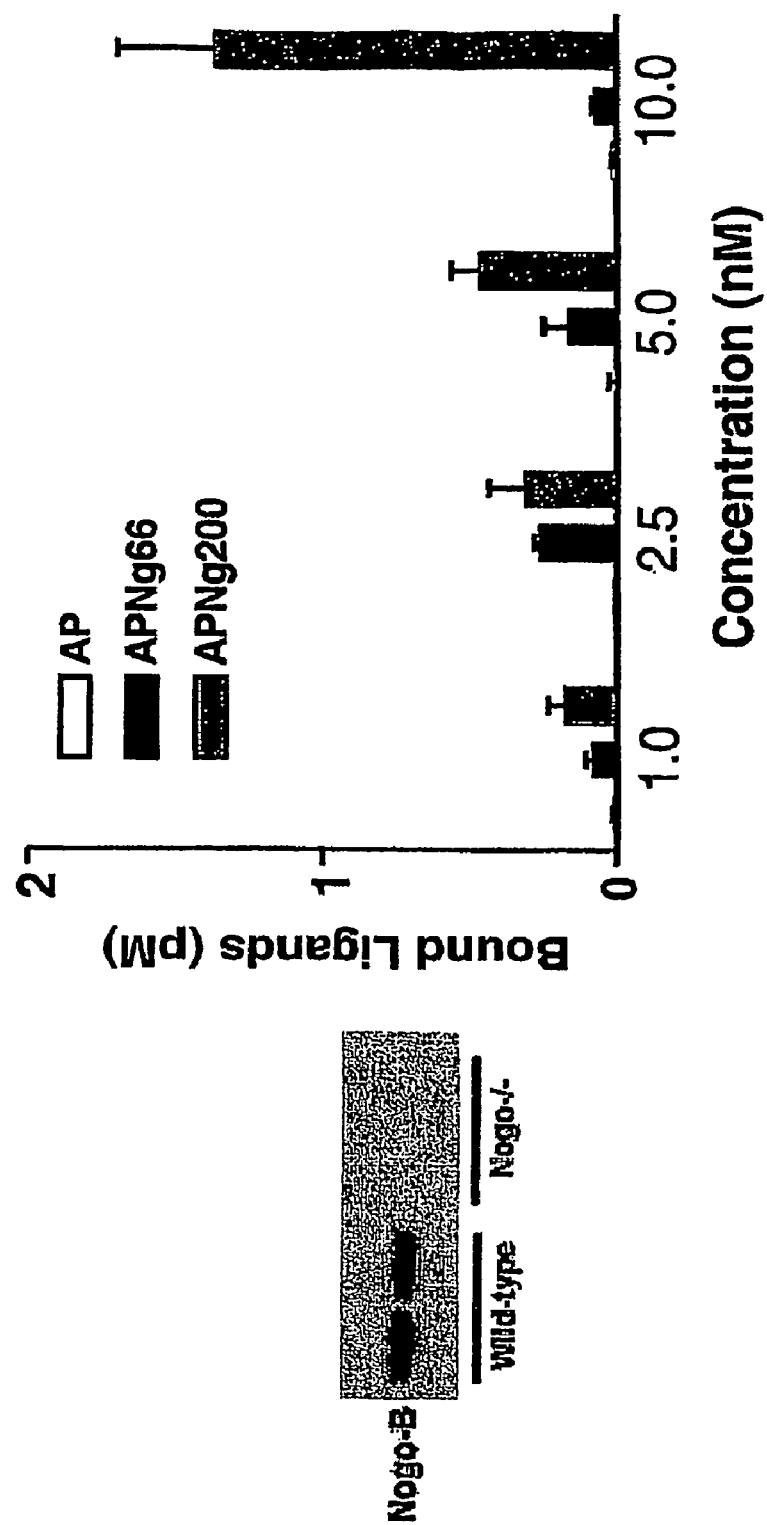
FIG. 46 shows the preferential binding of AP-Am-Nogo-B in mouse smooth muscle cells isolated from Nogo-A/B knockout mice.
Figure 47:
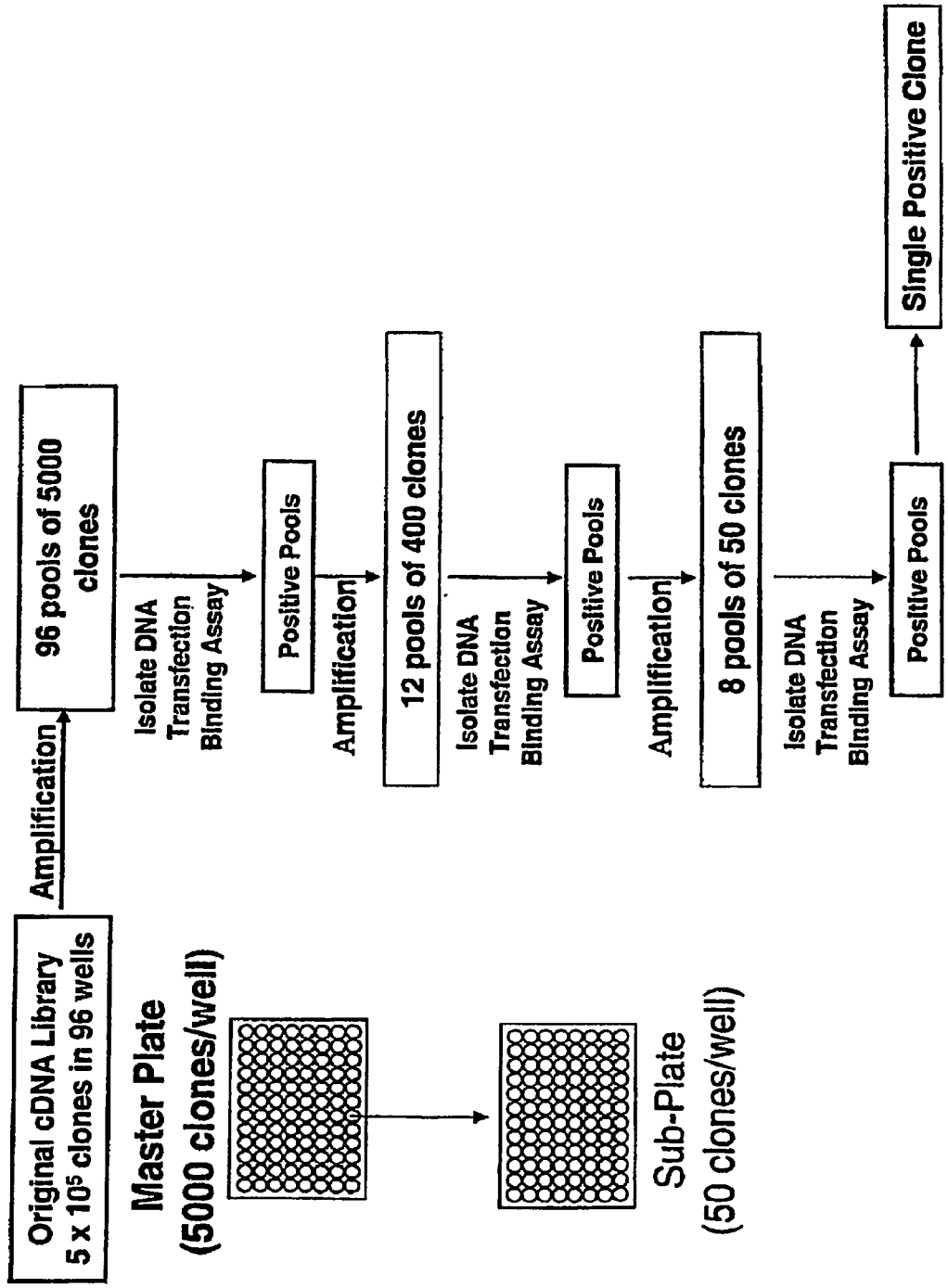
FIG. 47 is a flow chart showing how a clone is isolated from a cDNA library.
Figure 48:
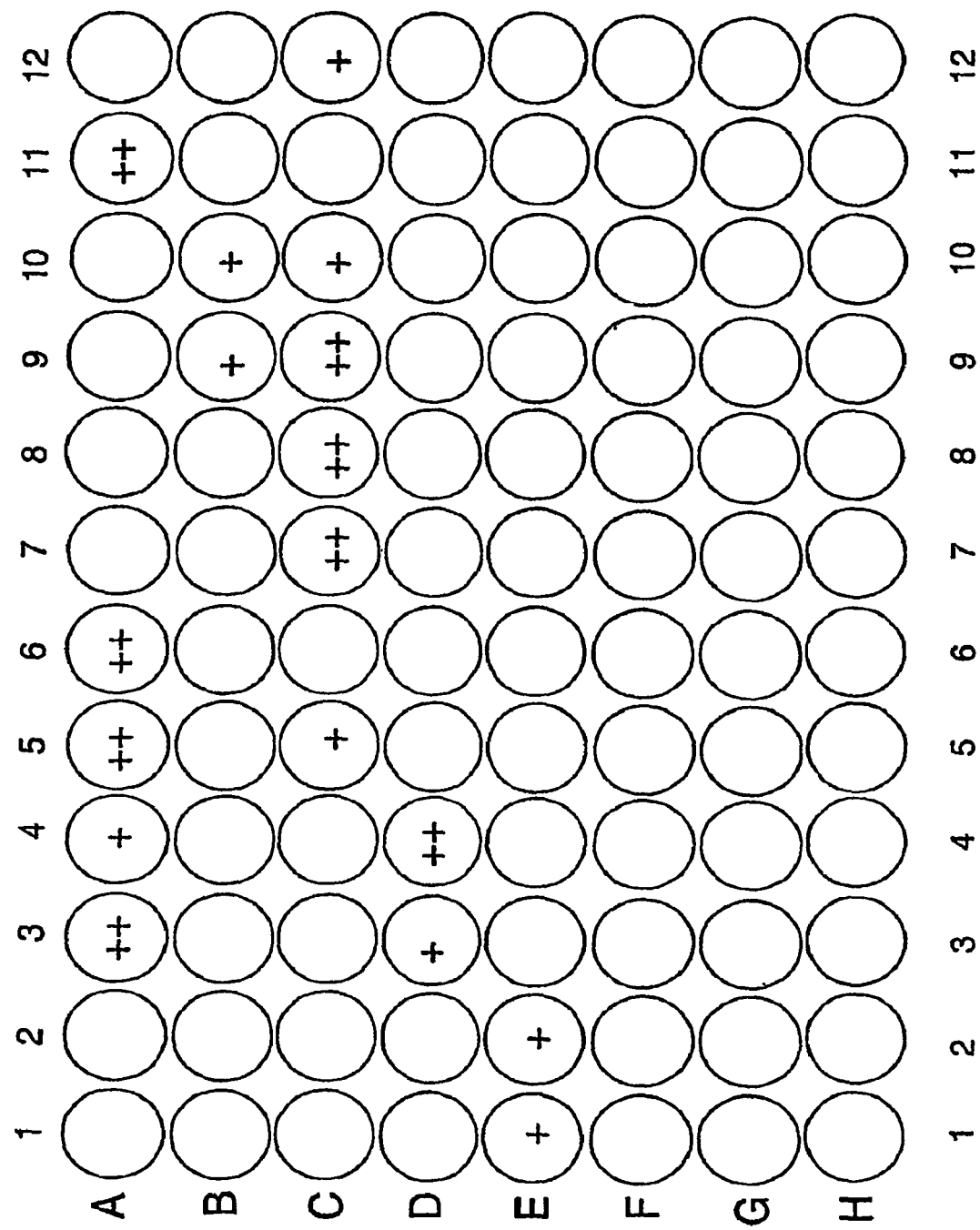
FIG. 48 shows that clones binding AP-Am-Nogo-B were identified in the assay.
Figure 49:
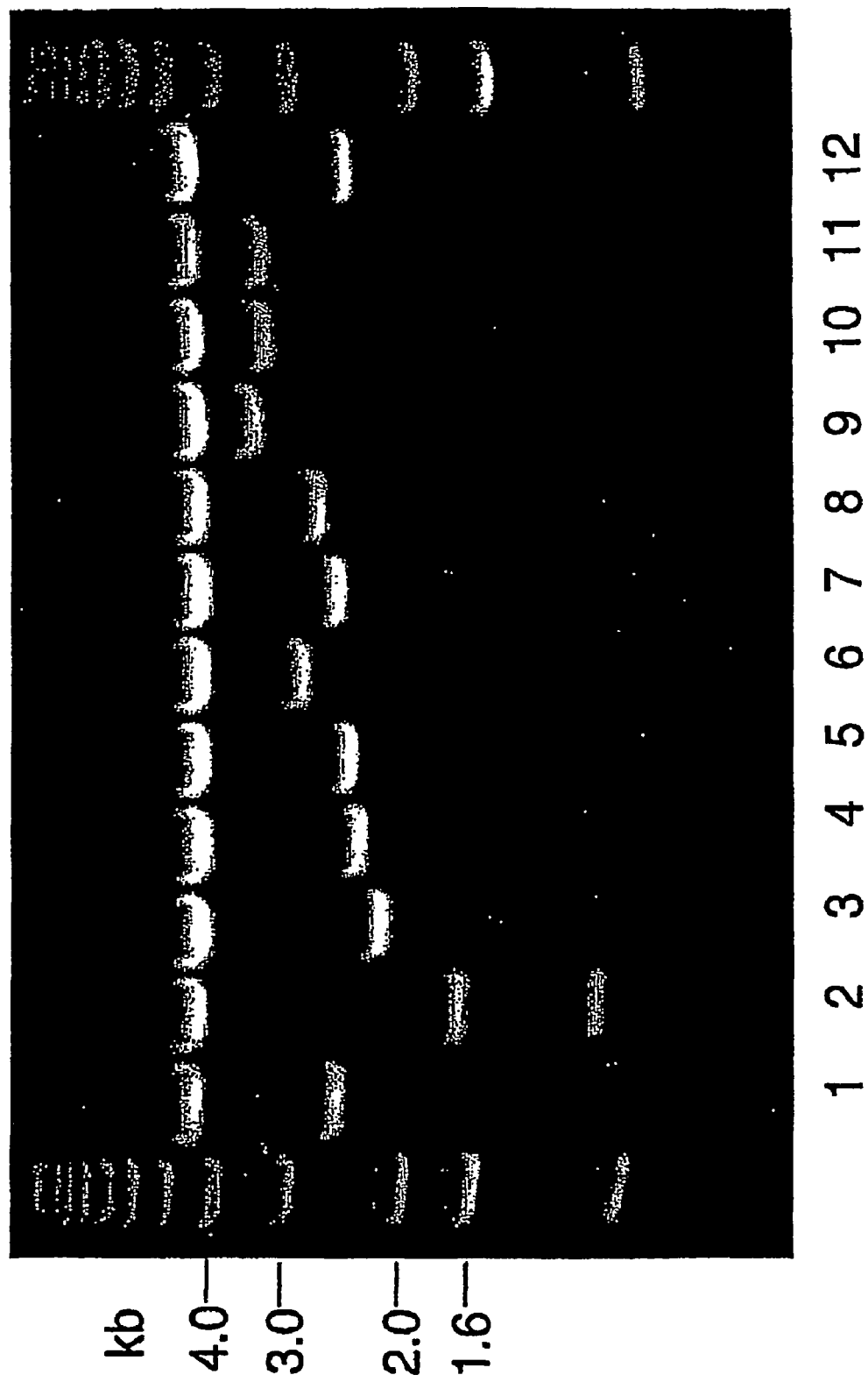
FIG. 49 shows the inserts of 12 clones released by NotI.
Figure 50:
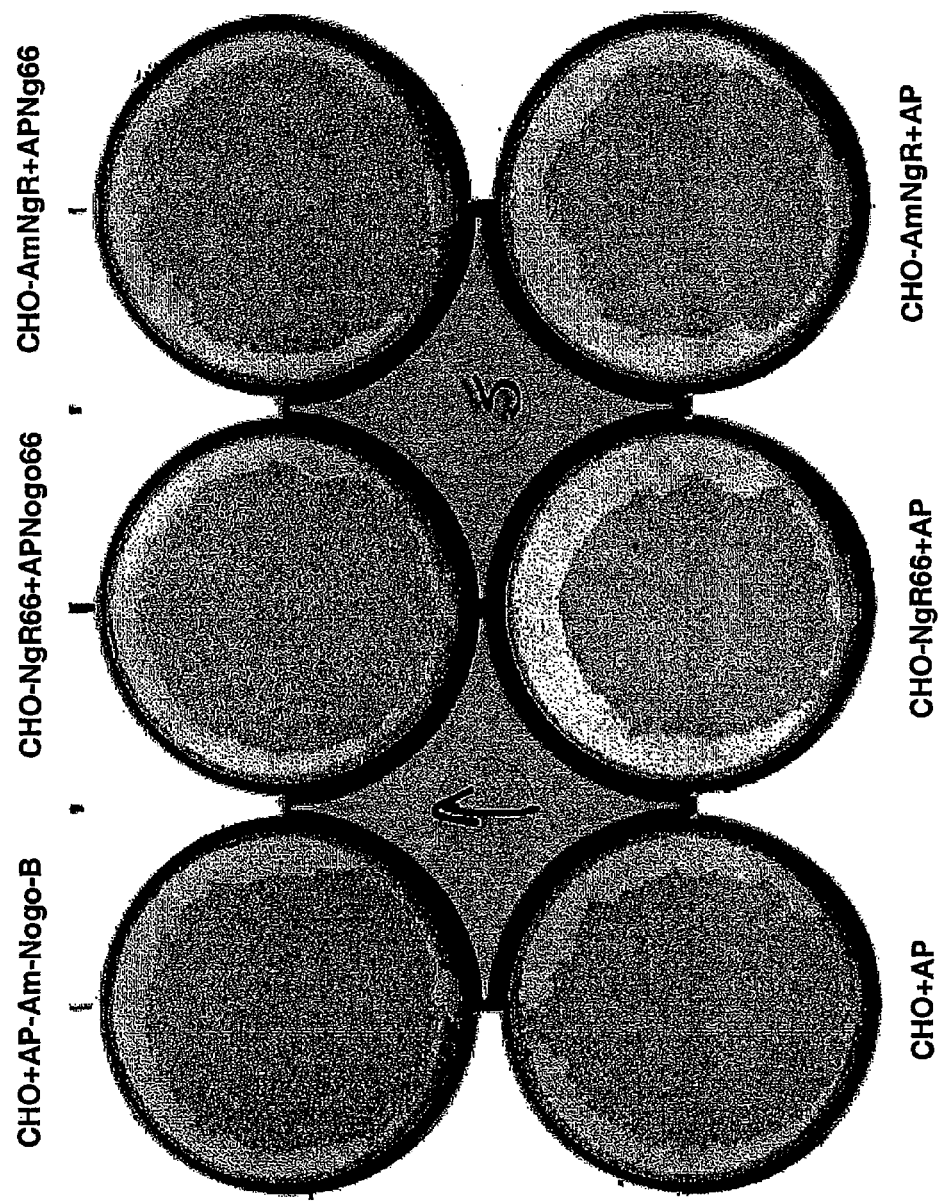
FIG. 50 shows staining of CHO cells transfected with Nogo-66 receptor (CHO-NgR66) or Am-Nogo receptor (CHO-AmNgR) with AP, AP-Am-Nogo-B or AP-Nogo-66 (APNogo66).
Figure 51:
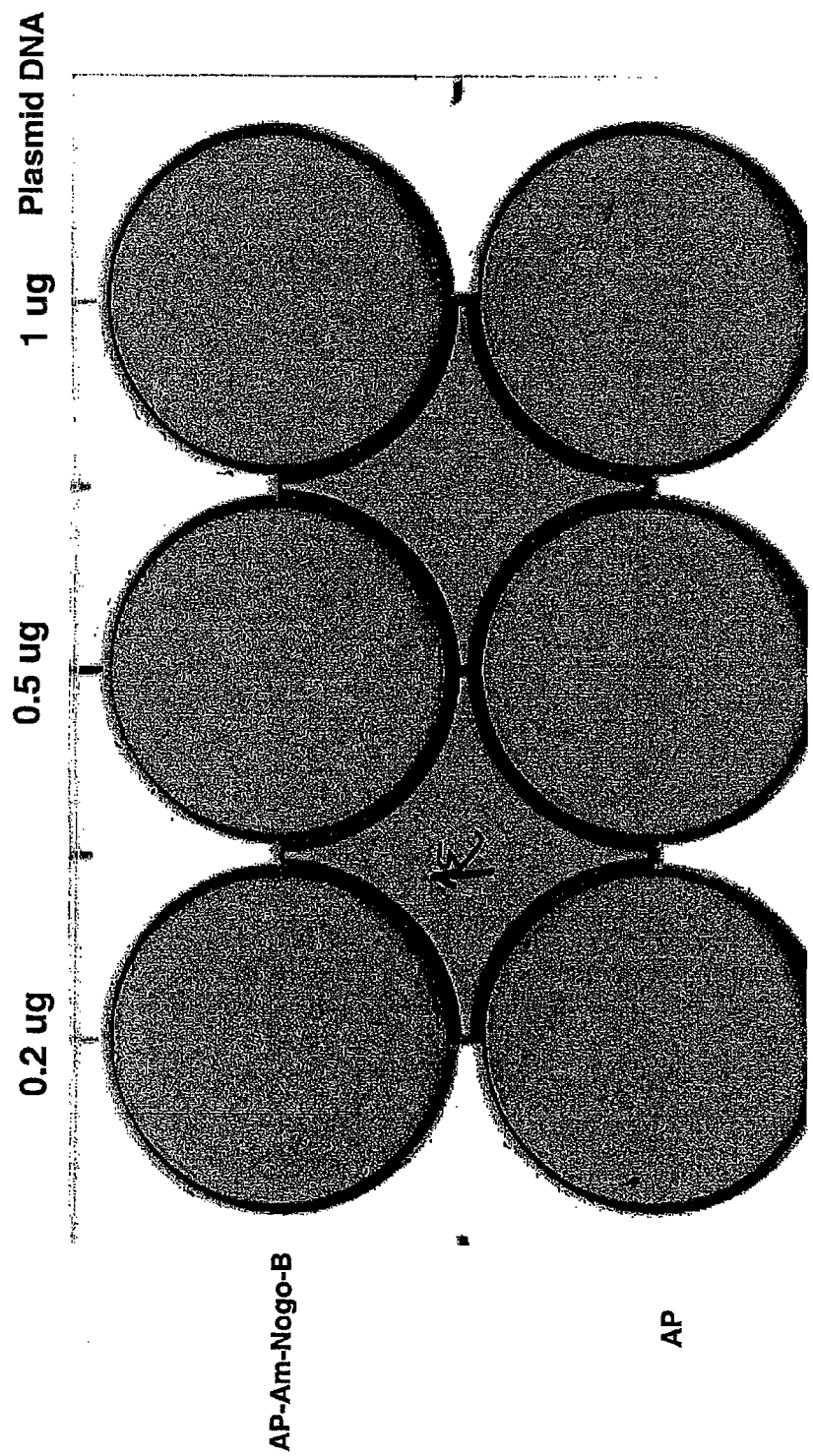
FIG. 51 shows staining of CHO-AmNgR cells stained with AP or AP-Am-Nogo-B.
Figure 52:
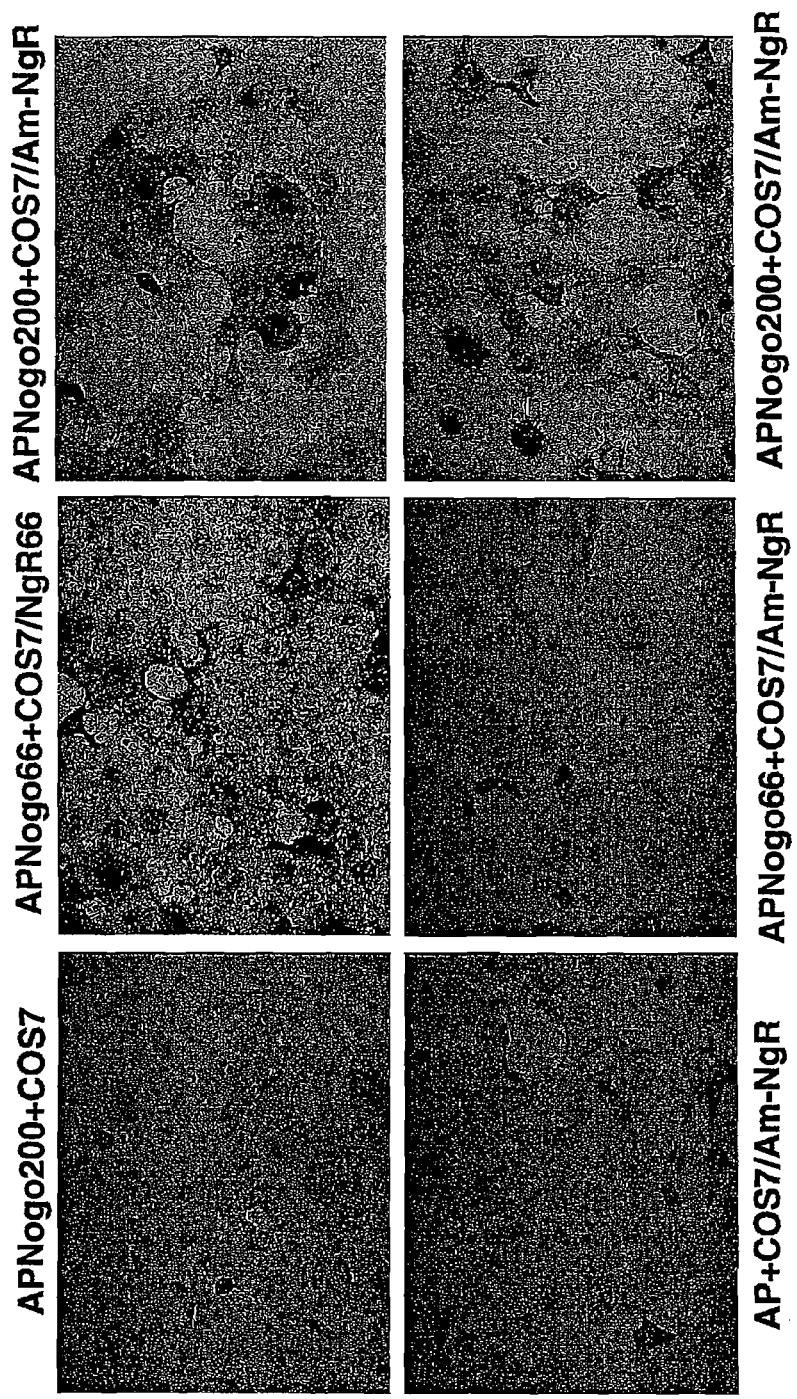
FIG. 52 shows staining of COS-7 cells transfected with NgR66 or Am-NgR with AP, APNogo66 or AP-Am-Nogo-B (APNogo200).
Figure 53:
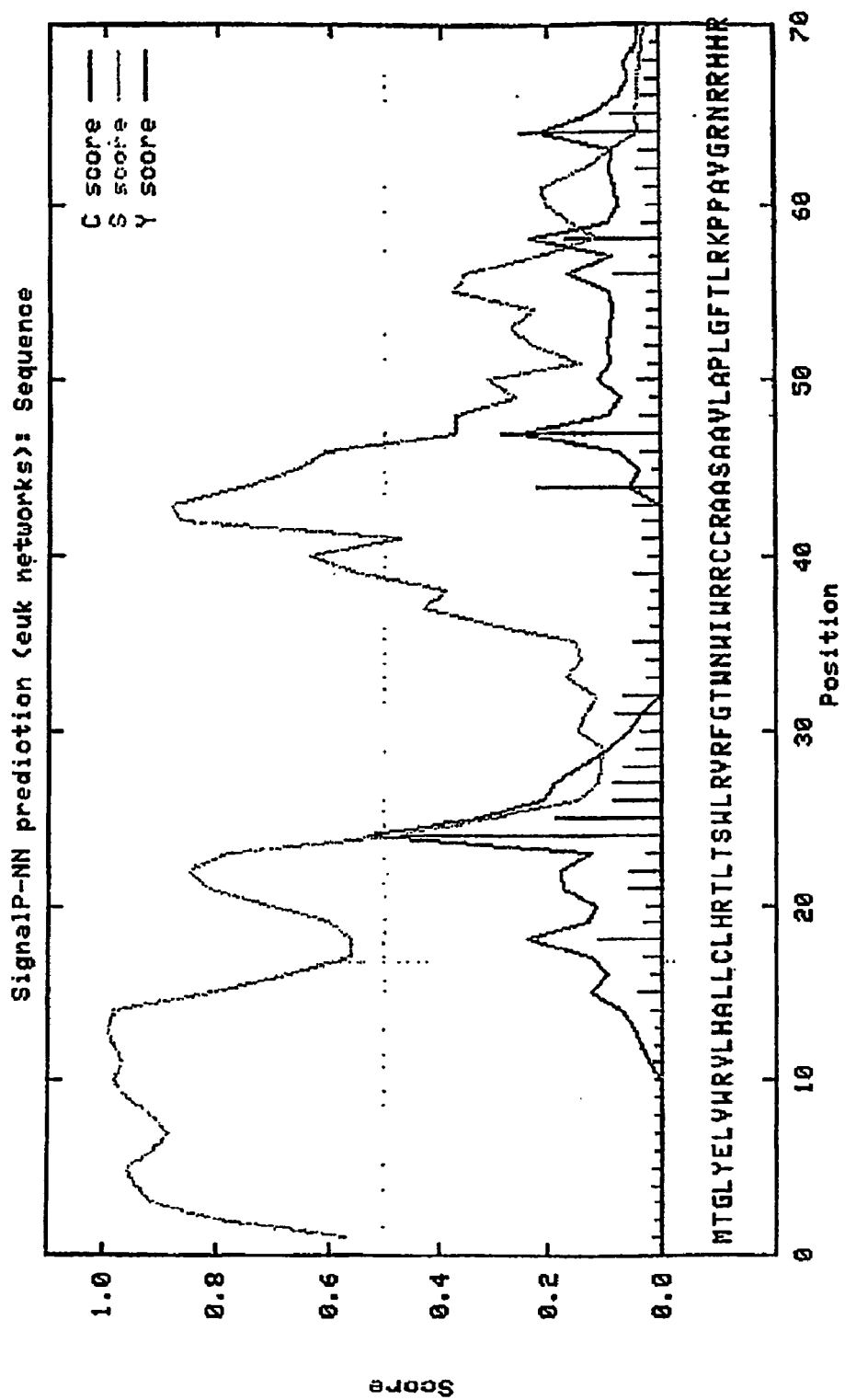
FIG. 53 shows a prediction of the presence and location of signal peptide cleavage sites in human NgBR.
Figure 54:
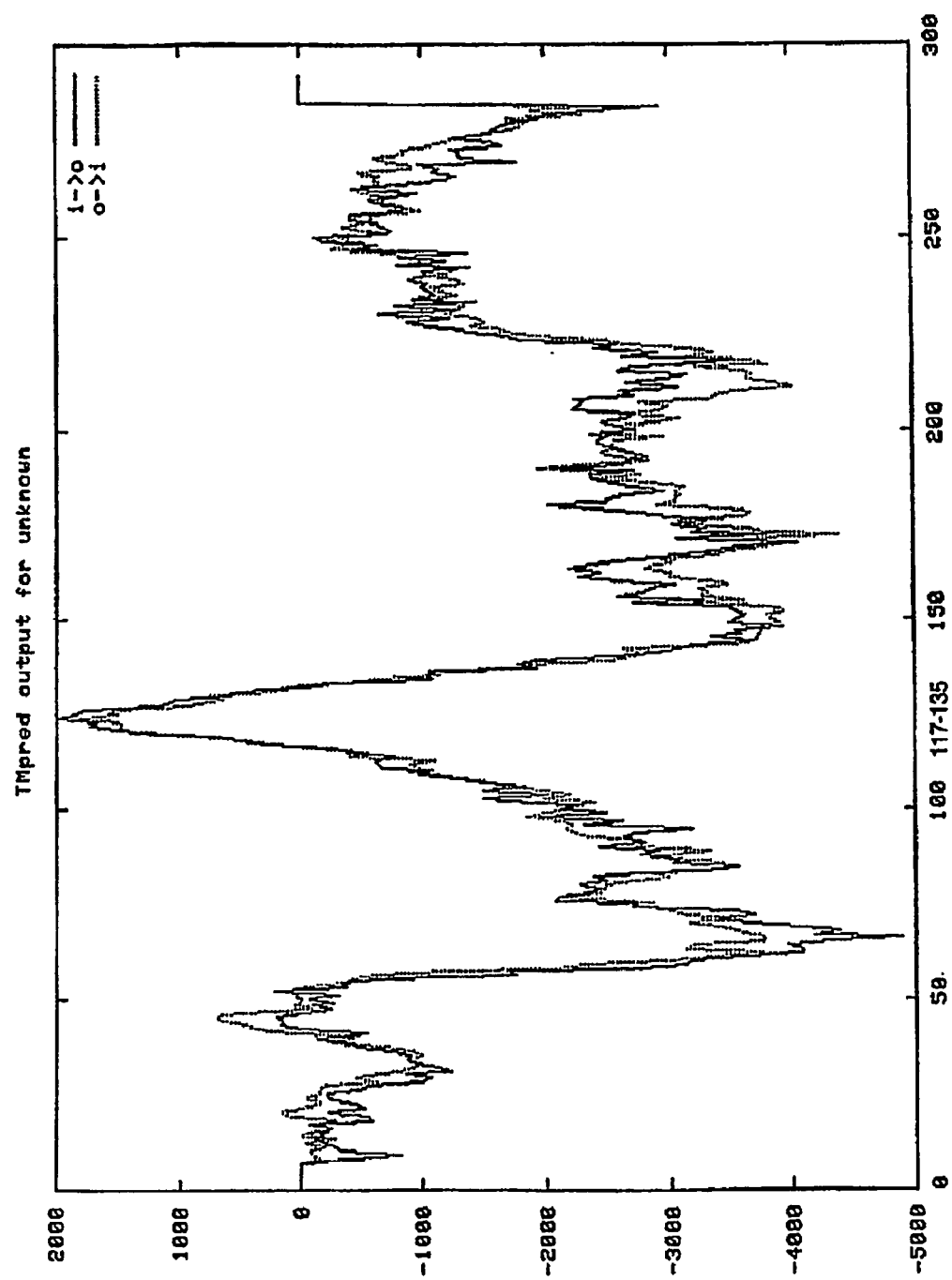
FIG. 54 shows a prediction of the transmembrane regions of human NgBR.
Figure 55:
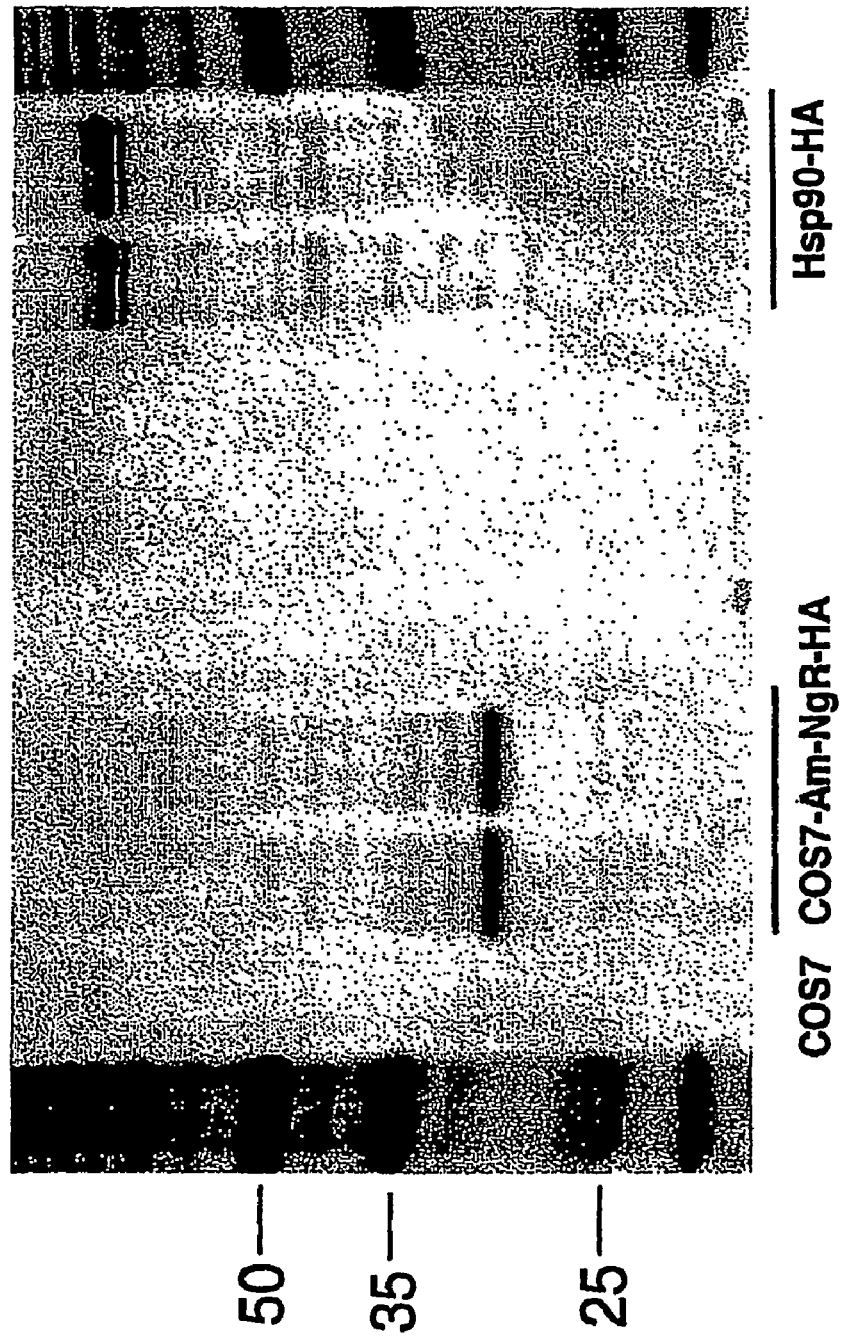
FIG. 55 shows the expression of a Am-NgR-HA fusion protein in COS-7 cells.
Figure 56:
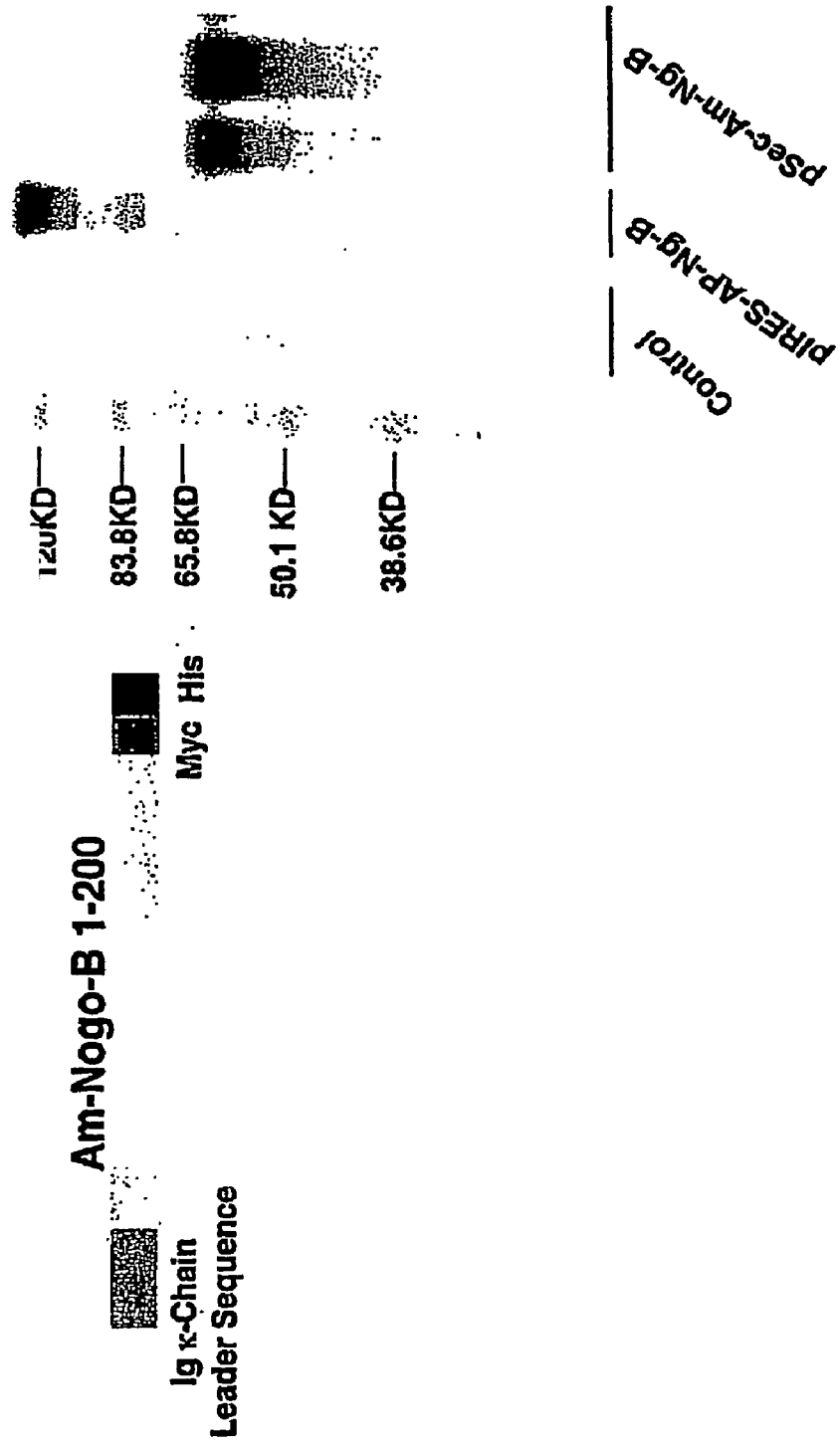
FIG. 56 shows the binding of an anti-Nogo-B antibody (N18) to cells transfected with vectors expressing AP-Nogo-B (pIRES-AP-Ng-B) or AM-Nogo-B (pSec-Am-Ng-B).
Figure 57:
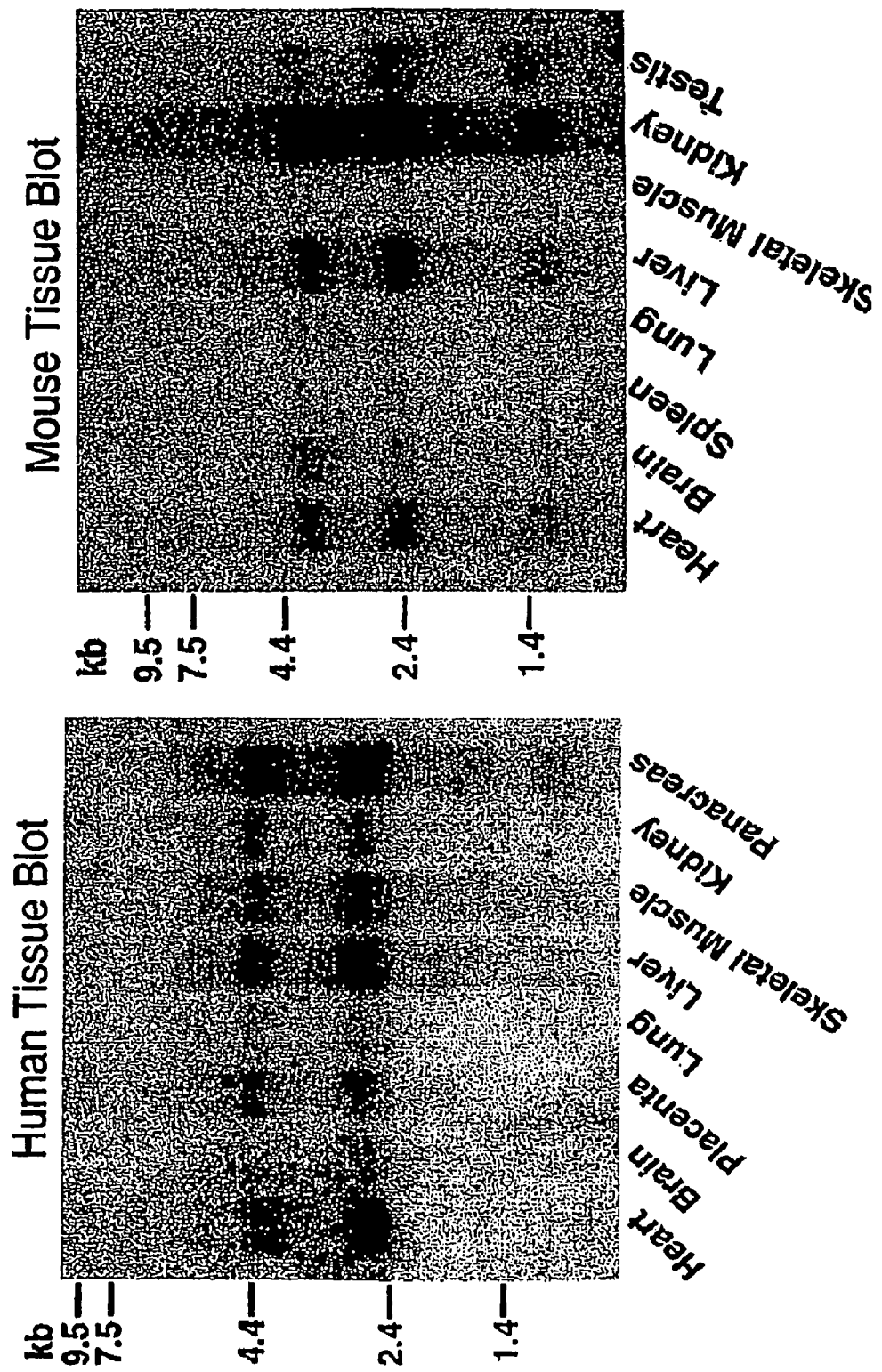
FIG. 57 shows the tissue distribution of NgBR in human and mouse tissues.
Figure 58:
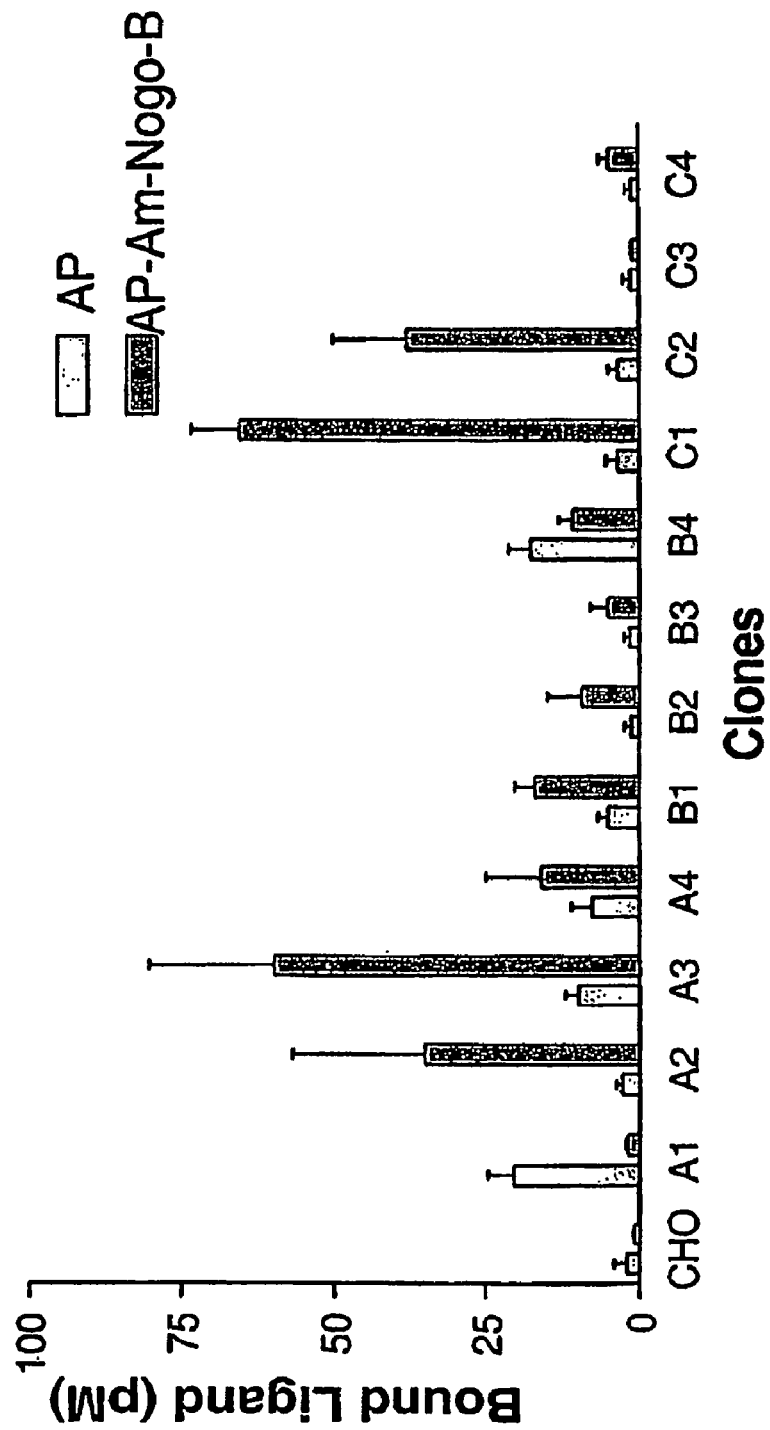
FIG. 58 shows that stable CHO cell lines expressing NgBR were established, as indicated by preferential binding of AP-Am-Nogo-B over AP.
Figure 59:
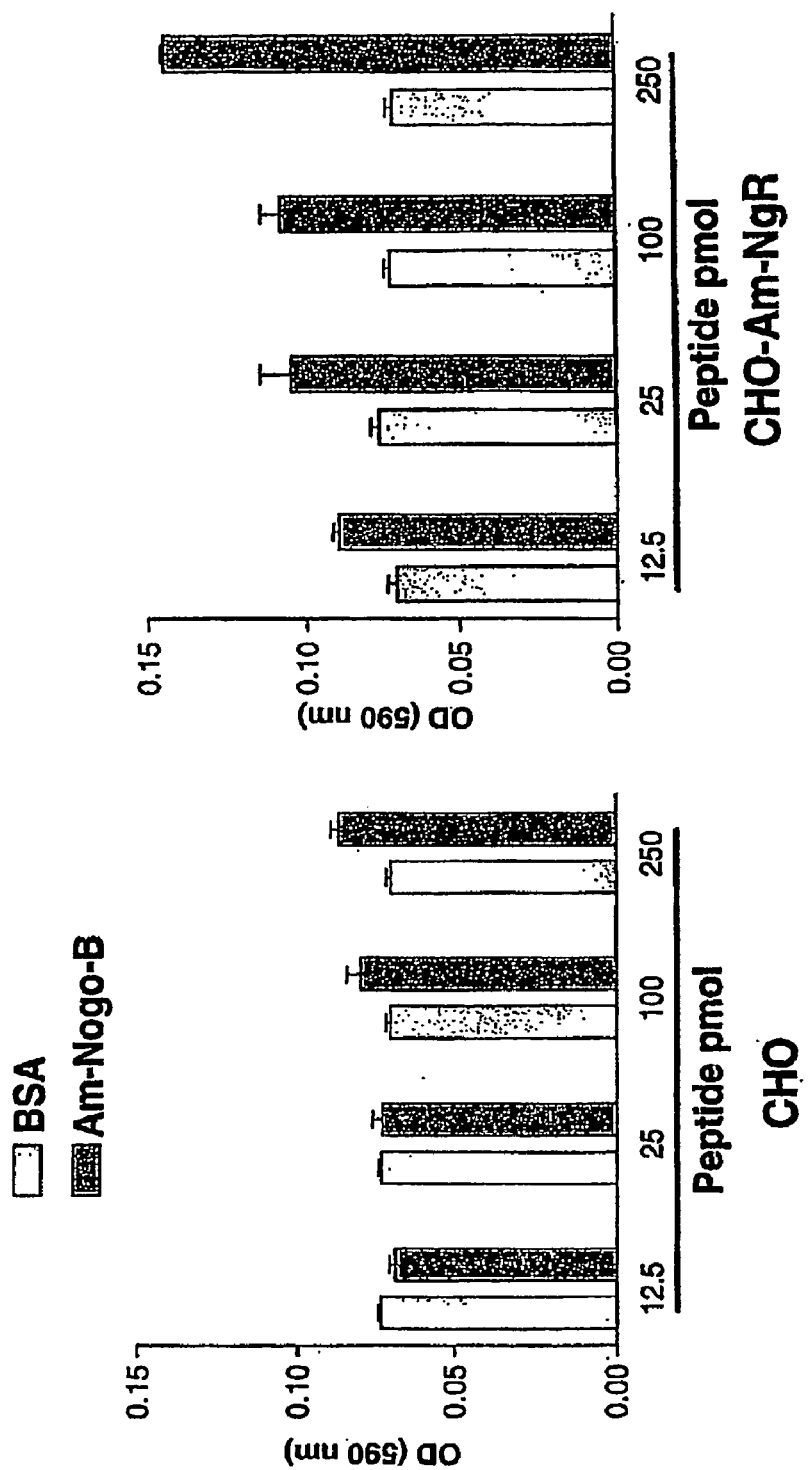
FIG. 59 shows that Am-Nogo-B promotes cell adhesion in CHO cells expressing NgBR (CHO-Am-NgR).
Figure 60:
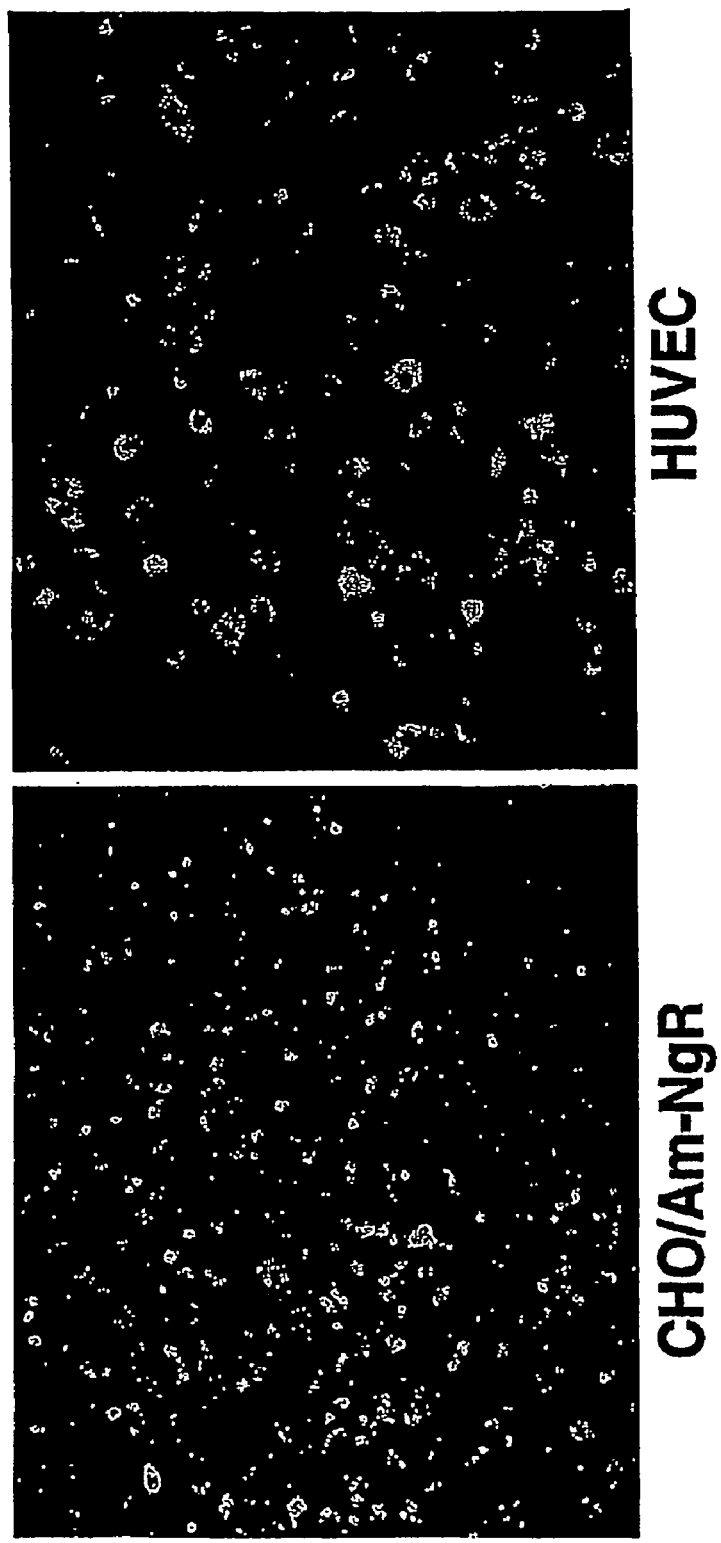
FIG. 60 shows the effect of transfecting RNAi in CHO-AmNgR cells and HUVEC.
Figure 61:
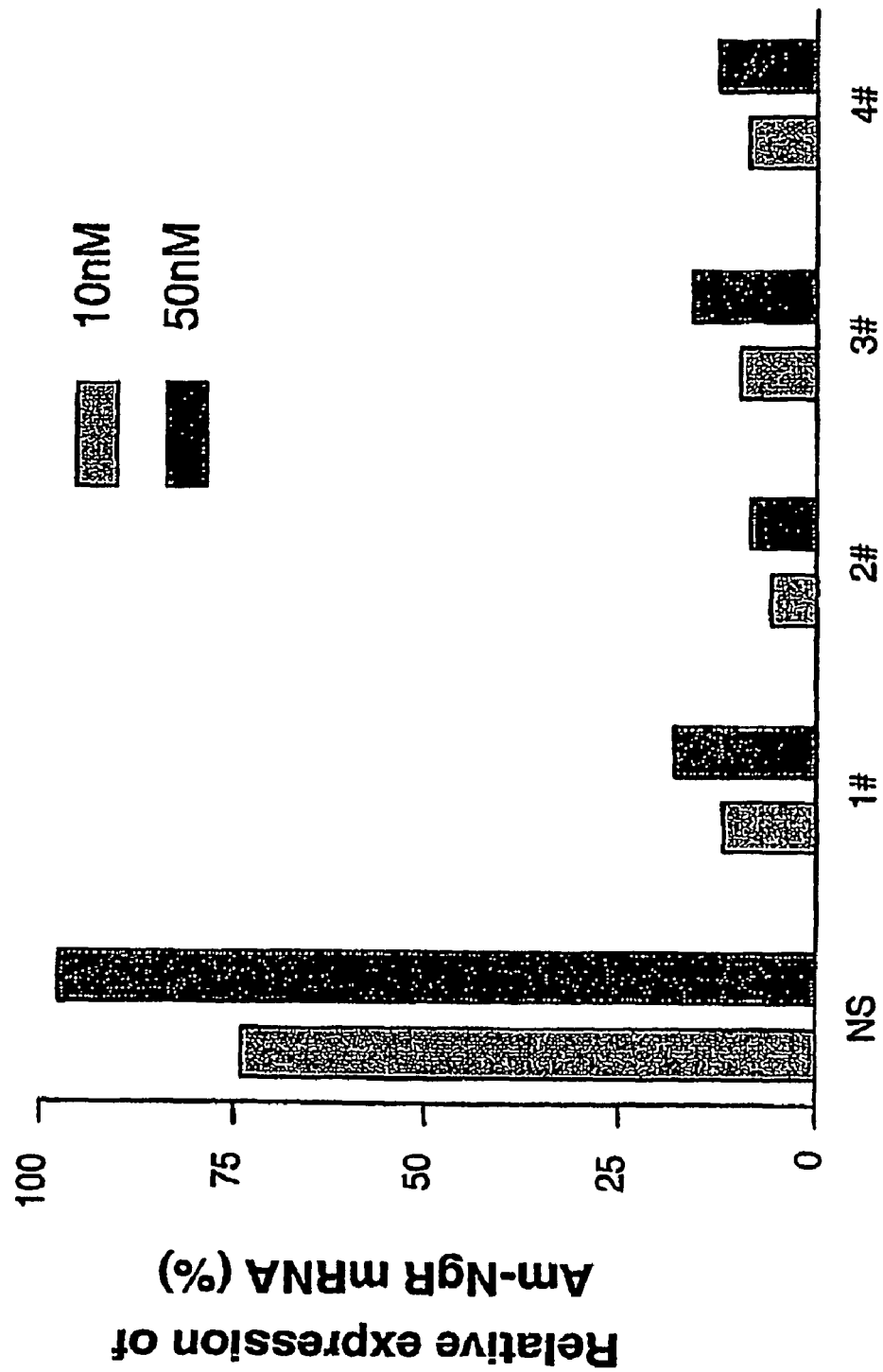
FIG. 61 shows that transfection of various siRNA downregulates NgBR (Am-NgR) mRNA in CHO-AmNgR cells.
Figure 62:
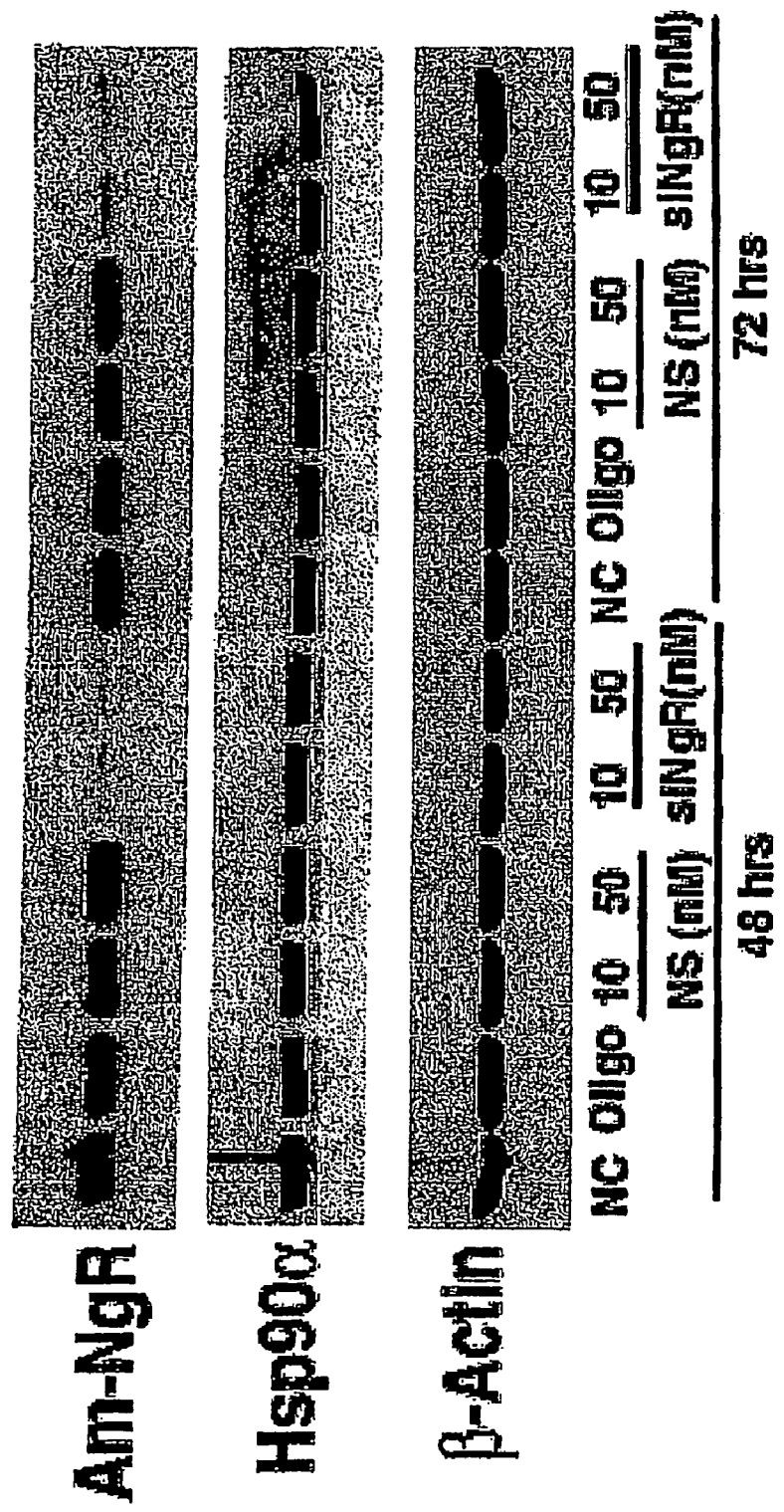
FIG. 62 shows that transfection of siRNA downregulates NgBR (Am-NgR) protein levels in CHO-AmNgR cells.
Figure 63:
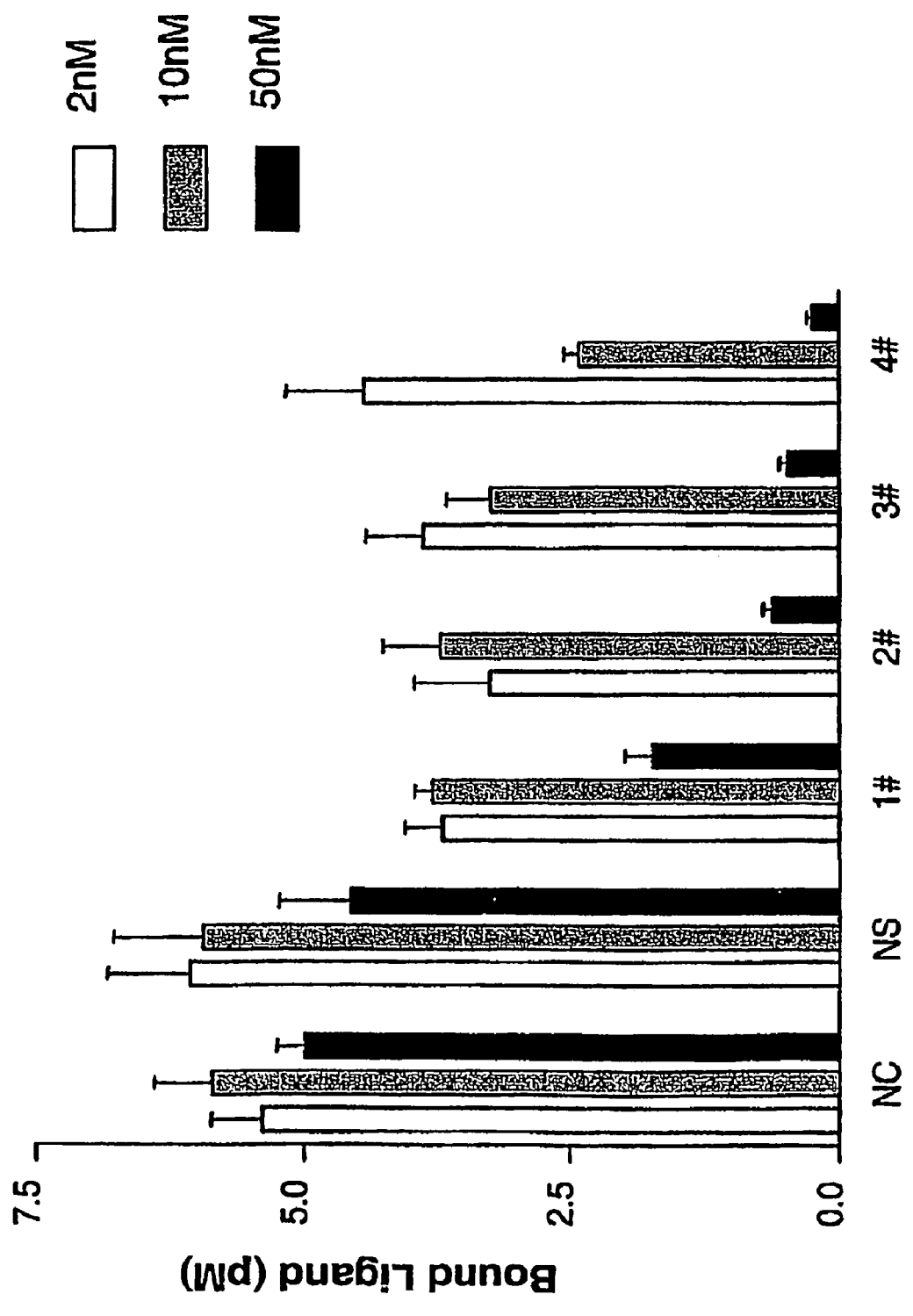
FIG. 63 shows the effects of siRNA transfection on AP-Am-Nogo-B binding on CHO-AmNgR cells.
Figure 64:
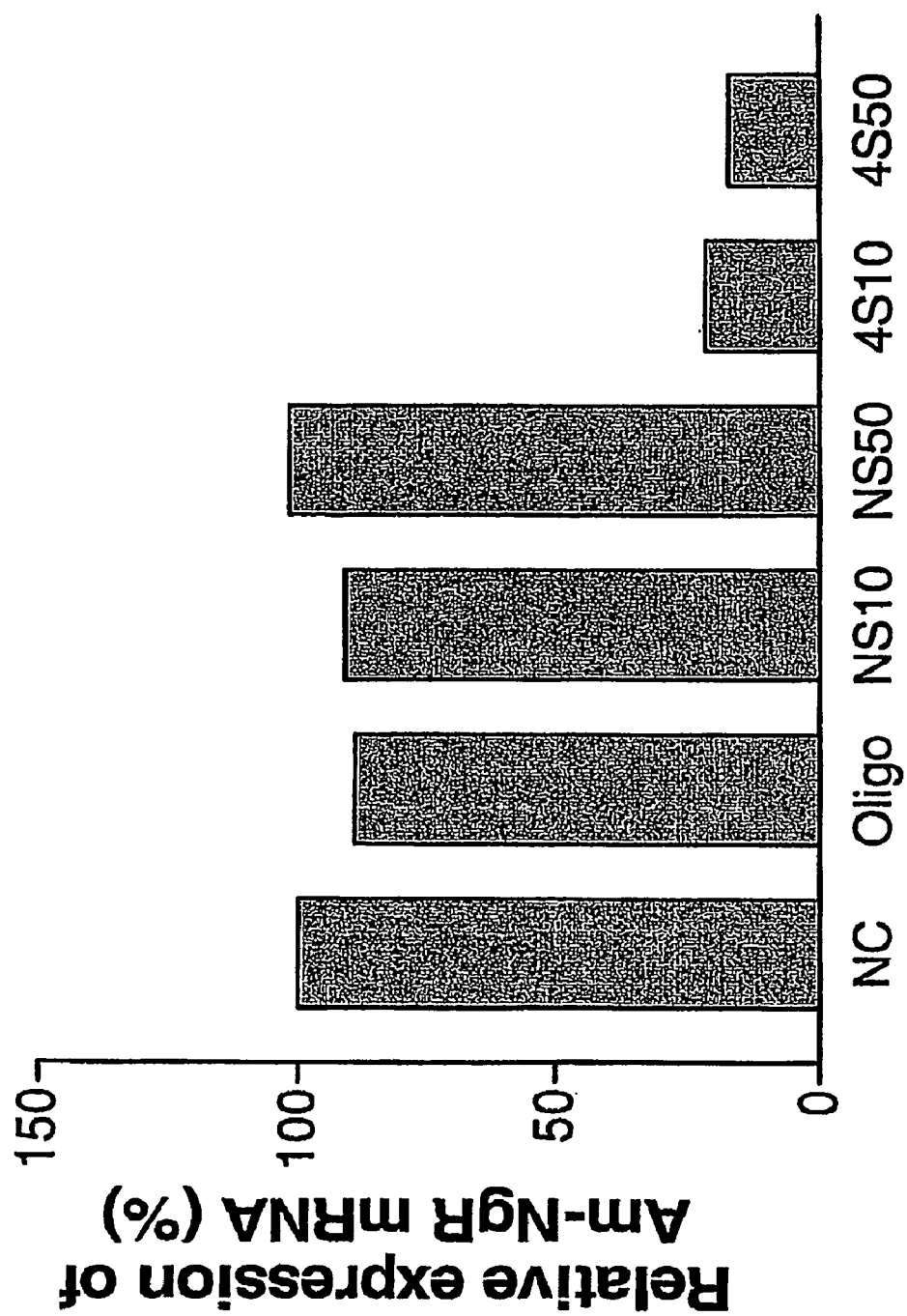
FIG. 64 shows that transfection of various siRNA downregulates NgBR (Am-NgR) mRNA in HUVEC.
Figure 65:
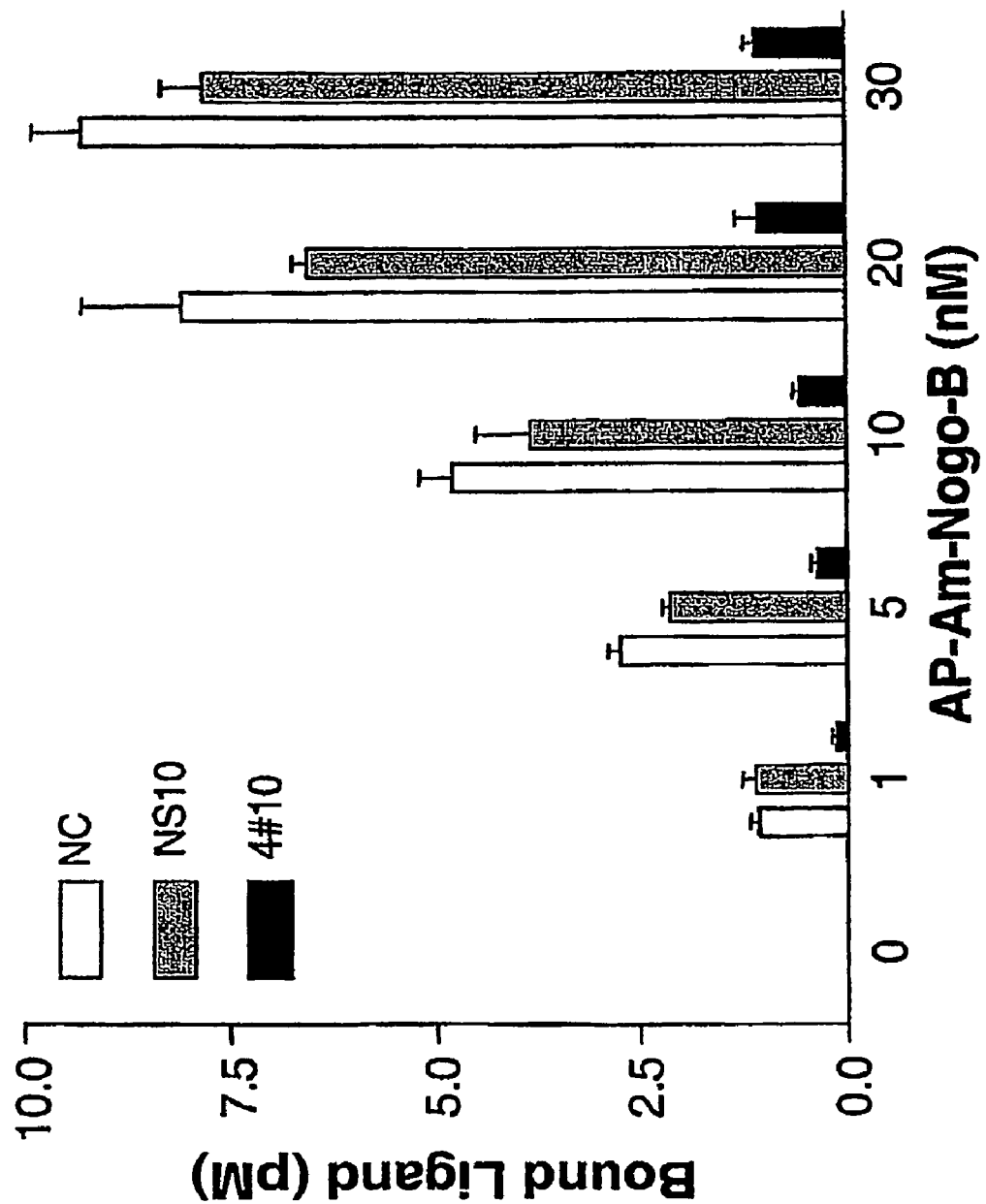
FIG. 65 shows the effects of siRNA transfection on AP-Am-Nogo-B binding on HUVEC.
Figure 66:
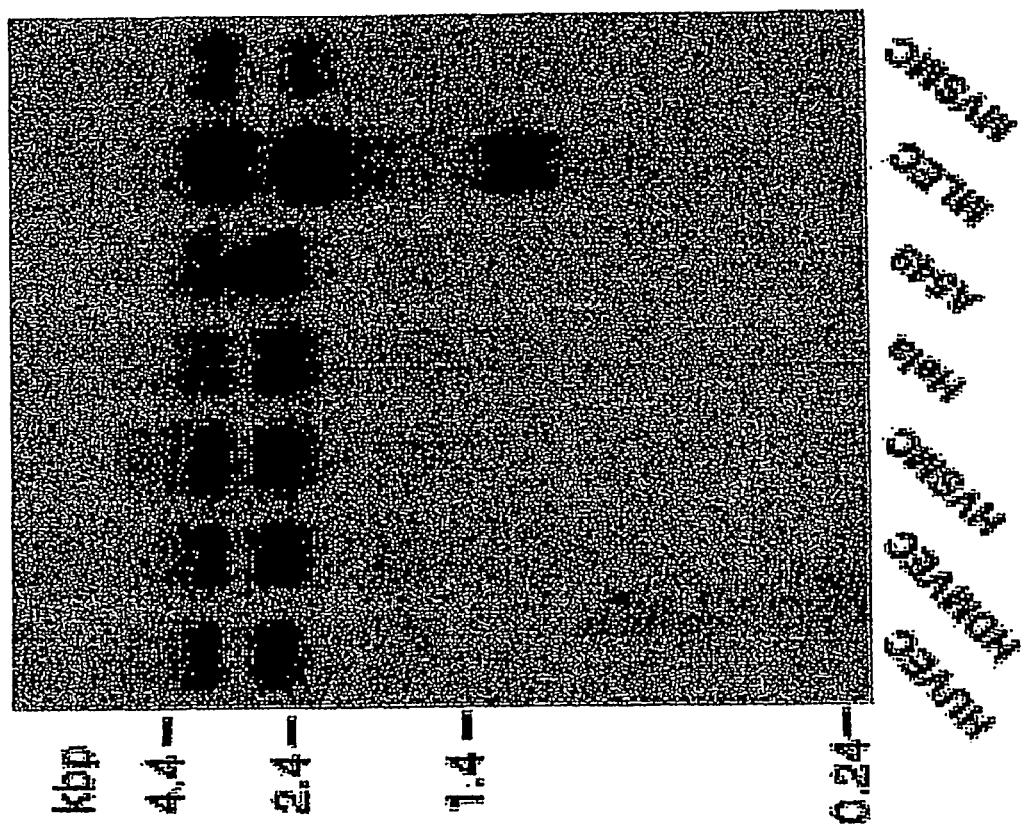
FIG. 66 shows the expression of NgR expression, based upon a Northern analysis.
Figure 67:
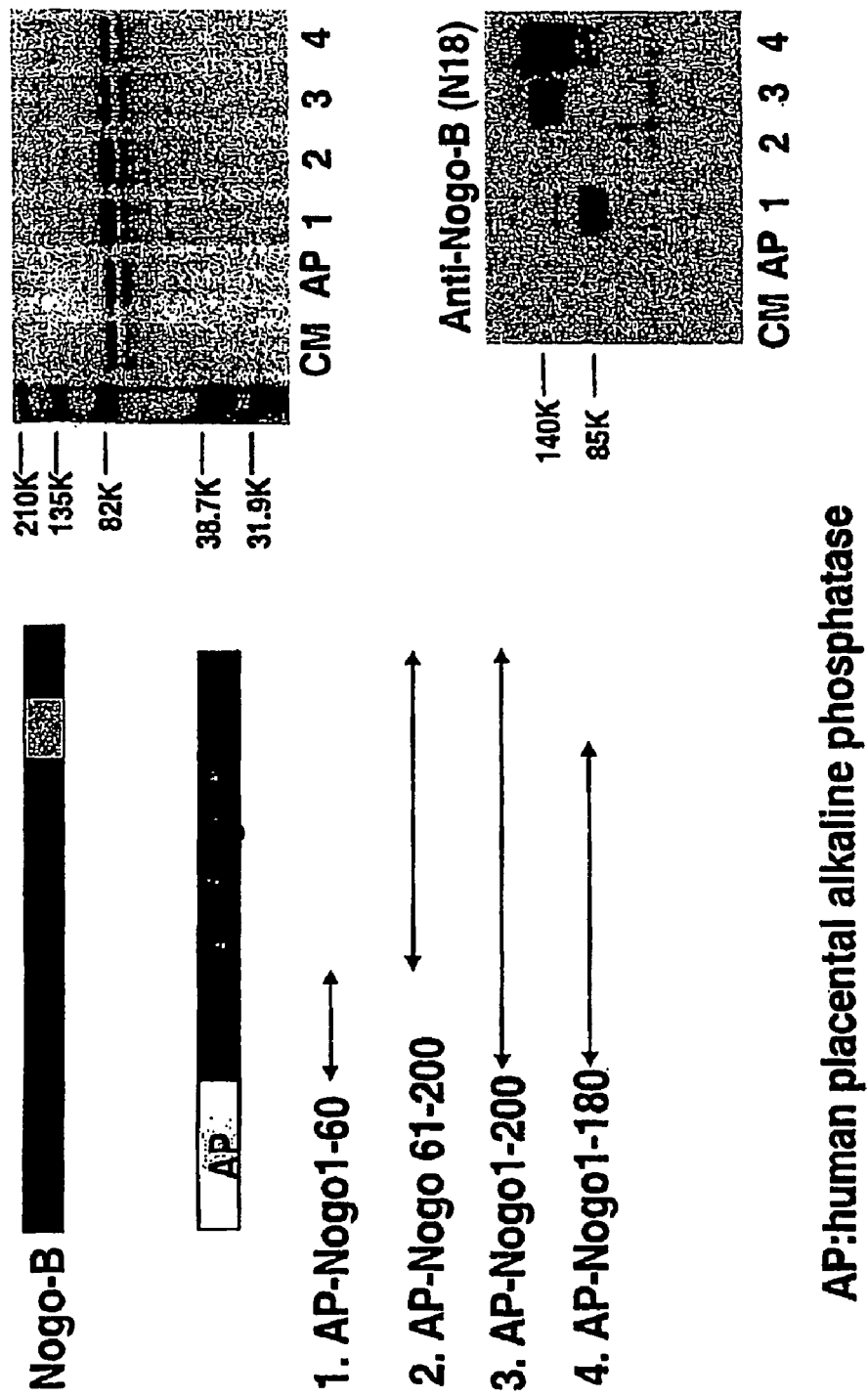
FIG. 67 shows various constructs of AP fused with fragments of Nogo-B.
Figure 68:
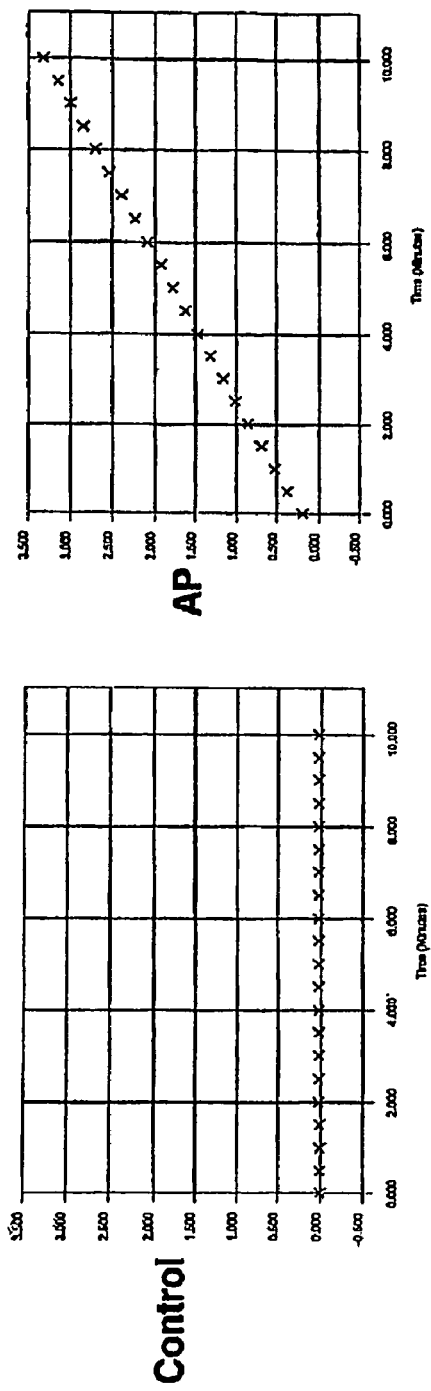
FIG. 68 shows the AP activity in AP fusion proteins is both time- and concentration-dependent.
Figure 68:
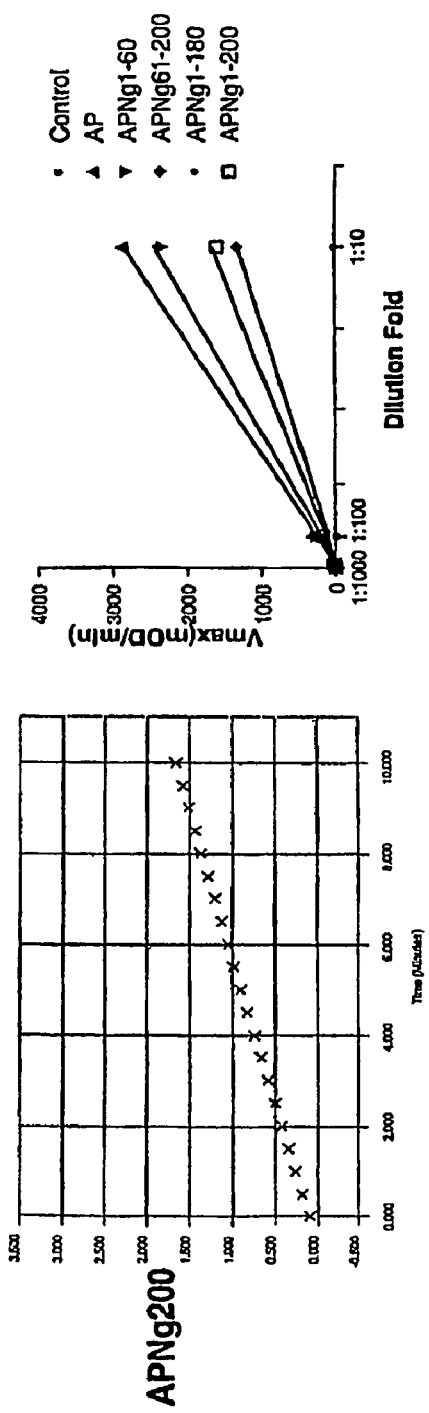

As shown in FIG. 40, injection with adenoviral mFc did not slow the growth of Am-Nogo-B-expressing A549 cells, whereas adenoviral mFc-ecto markedly reduced tumor growth in vivo. These data suggest that the mFc-ectodomain of NgBR is therapeutically active to reduce growth of human tumors in nude mice.

What is claimed is:

1. A composition comprising a fragment of a Nogo-B receptor that inhibits a biological activity of a Nogo-B receptor, wherein said fragment consists of residues 52-116 of SEQ ID NO: 1.

2. A fusion protein comprising a fragment of Nogo-B receptor and a heterologous protein component, wherein said fragment consists of residues 52-116 of SEQ ID NO: 1.

3. A nucleic acid molecule comprising a nucleotide sequence encoding the fusion protein of claim 2.

4. A vector comprising the nucleic acid molecule of claim 3.

5. A host cell comprising the nucleic acid molecule of claim 3 or the vector of claim 4.

6. A method for producing a fusion protein, wherein said fusion protein comprises a fragment of Nogo-B receptor consisting of residues 52-116 of SEQ ID NO: 1, said method comprising culturing the host cell of claim 5 under suitable conditions in media so that the host cell produces the fusion protein and isolating the fusion protein.

7. A composition comprising a fragment of a Nogo-B receptor that inhibits a biological activity of a Nogo-B receptor, wherein said fragment consists of the amino acid sequence of SEQ ID NO: 14, SEQ ID NO: 16, or SEQ ID NO: 18.

8. A fusion protein comprising a fragment of Nogo-B receptor and a heterologous protein component, wherein said fragment consists of the amino acid sequence of SEQ ID NO: 14, SEQ ID NO: 16, or SEQ ID NO: 18.

9. A nucleic acid molecule comprising a nucleotide sequence encoding the fusion protein of claim 8.

10. A vector comprising the nucleic acid molecule of claim 9.

11. A host cell comprising the nucleic acid molecule of claim 9 or the vector of claim 10.

12. A method for producing a fusion protein, wherein said fusion protein comprises a fragment of Nogo-B receptor consisting of the amino acid sequence of SEQ ID NO: 14, SEQ ID NO: 16, or SEQ ID NO: 18, said method comprising culturing the host cell of claim 11 under suitable conditions in media so that the host cell produces the fusion protein and isolating the fusion protein.

* * * * *